US011168119B2

(12) United States Patent
Rothe et al.

(10) Patent No.: US 11,168,119 B2
(45) Date of Patent: Nov. 9, 2021

(54) LIPOCALIN MUTEINS WITH BINDING AFFINITY FOR LAG-3

(71) Applicant: Pieris Pharmaceuticals GmbH, Freising (DE)

(72) Inventors: Christine Rothe, Dachau (DE); Shane Olwill, Freising (DE); Andrea Allersdorfer, Wolnzach (DE); Timo Eichner, Freising (DE); Rachida Siham Bel Aiba, Munich (DE); Marina Pavlidou, Freising (DE)

(73) Assignee: PIERIS PHARMACEUTICALS GMBH, Freising (DE)

( * ) Notice: Subject to any disclaimer, the term of this patent is extended or adjusted under 35 U.S.C. 154(b) by 0 days.

(21) Appl. No.: 16/478,465

(22) PCT Filed: Jan. 18, 2018

(86) PCT No.: PCT/EP2018/051139
§ 371 (c)(1),
(2) Date: Jul. 16, 2019

(87) PCT Pub. No.: WO2018/134274
PCT Pub. Date: Jul. 26, 2018

(65) Prior Publication Data
US 2019/0345207 A1    Nov. 14, 2019

(30) Foreign Application Priority Data
Jan. 18, 2017 (EP) ..................... 17151945

(51) Int. Cl.
*C07K 14/47* (2006.01)
*G01N 33/68* (2006.01)
*A61K 38/00* (2006.01)

(52) U.S. Cl.
CPC ......... *C07K 14/47* (2013.01); *G01N 33/6872* (2013.01); *A61K 38/00* (2013.01); *C07K 2318/20* (2013.01); *G01N 2333/70503* (2013.01)

(58) Field of Classification Search
None
See application file for complete search history.

(56) References Cited

U.S. PATENT DOCUMENTS

| | | | | |
|---|---|---|---|---|
| 7,585,940 | B2 * | 9/2009 | Skerra | C07K 14/47 530/350 |
| 7,893,208 | B2 * | 2/2011 | Skerra | A61P 43/00 530/350 |
| 9,212,208 | B2 | 12/2015 | Matschiner et al. | |
| 9,522,940 | B2 * | 12/2016 | Klaus | C07K 14/435 |
| 10,501,510 | B2 * | 12/2019 | Rothe | A61P 43/00 |
| 10,526,384 | B2 * | 1/2020 | Hinner | C07K 14/54 |
| 2019/0031729 | A1 | 1/2019 | Rothe et al. | |
| 2020/0048317 | A1 | 2/2020 | Rothe et al. | |

FOREIGN PATENT DOCUMENTS

| | | |
|---|---|---|
| JP | 2007-531503 A | 11/2007 |
| WO | WO-2004/078928 A2 | 9/2004 |
| WO | WO-2005/019256 A2 | 3/2005 |
| WO | WO-2007/107563 A2 | 9/2007 |
| WO | WO-2013/087660 A1 | 6/2013 |
| WO | WO-2013/174783 A1 | 11/2013 |
| WO | WO-2014/076321 A1 | 5/2014 |
| WO | WO-2015/104406 A2 | 7/2015 |
| WO | WO-2016/184882 A1 | 11/2016 |
| WO | WO-2017009456 A1 * | 1/2017 ......... G01N 33/6893 |
| WO | WO-2018/134274 A1 | 7/2018 |

OTHER PUBLICATIONS

Altschul et al., Gapped BLAST and PSI-BLAST: a new generation of protein database search programs, Nucleic Acids Res., 25(17):3389-3402 (1997).
Andreae, S. et al., Maturation and Activation of Dendritic Cells Induced by Lymphocyte Activation Gene-3 (CD223), The Journal of Immunology, 168:3874-3880 (2002).
Bruckdorfer, T., et al., From Production of Peptides in Milligram Amounts for Research to Multi-Tons Quantities for Drugs of the Future, Curr. Pharm. Biotechnol., 2004, 5:29-43.
Bruestedt, D. et al., The 1.8-A crystal structure of human tear lipocalin reveals an extended branched cavity with capacity for multiple ligands, J Biol Chem, 280(1):484-93 (2005). . . .
Database Geneseq "TLPC mutant R26T/E27W/E30G/M31I/N32H/L33D/L56D/S58A/R60F/C61L/H106P." XP002762190, retrieved from EBI accession No. GSP:BBG44480 sequence, Jul. 17, 2014.
Database EPO Proteins "Sequence 14 from Patent W02013174783." XP002762189, retrieved from EBI accession No. EPOP:JC106601 sequence, Jan. 27, 2014.

(Continued)

*Primary Examiner* — Christina Bradley
(74) *Attorney, Agent, or Firm* — Neal, Gerber & Eisenberg LLP

(57) ABSTRACT

The present disclosure provides human tear lipocalin muteins that specifically bind to LAG-3, which can be used in pharmaceutical applications, for example, as anti-cancer agents and/or immune modulators for the treatment or prevention of human diseases such as cancer, infectious diseases, and autoimmune diseases. The present disclosure further shows the human lipocalin muteins can inhibit the binding of LAG-3 to MHC class II on cells overexpressing MHC class II. The present disclosure also concerns methods of making LAG-3 binding lipocalin muteins described herein as well as compositions comprising such lipocalin muteins. The present disclosure further relates to nucleic acid molecules encoding such lipocalin muteins and to methods for generation of such lipocalin muteins and nucleic acid molecules. In addition, the application discloses therapeutic and/or diagnostic uses of these lipocalin muteins as well as compositions comprising one or more of such lipocalin muteins.

28 Claims, 10 Drawing Sheets

Figure 2A:
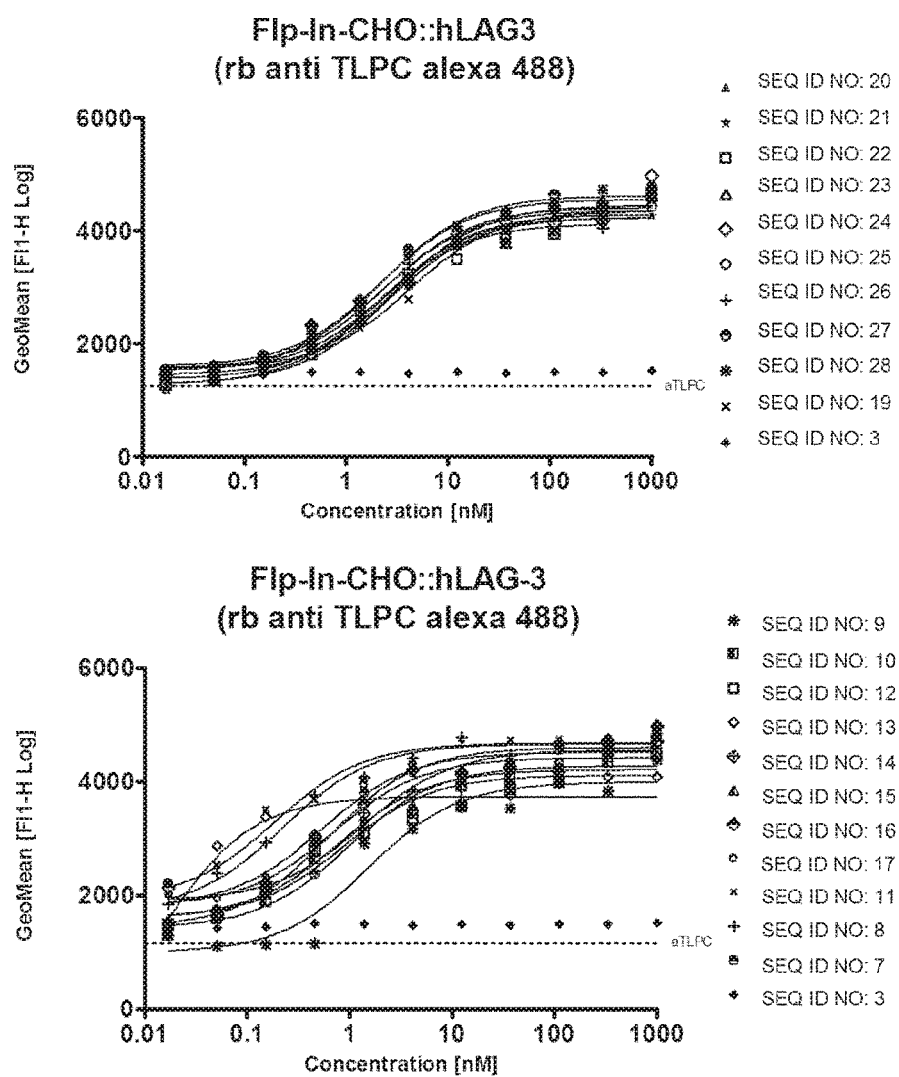

Specification includes a Sequence Listing.

(56) References Cited

OTHER PUBLICATIONS

Database EPO Proteins "Sequence 57 from Patent W02005019256." XP002762188, retrieved from EBI accession No. EPOP:CS048104 sequence, Mar. 22, 2005.
Database Geneseq "Human tear lipocalin (Tlc) mature protein mutant, SEQ ID: 3." XP002762191, retrieved from EBI accession No. GSP:BAP94977 sequence, Aug. 15, 2013.
Database Geneseq "Human tear lipocalin (Tlc) protein mutant" XP002779166, retrieved from EBI accession No. GSP:BDJ69211, Database accession No. BDJ69211, Jan. 12, 2017.
Database Geneseq "Human tear lipocalin (Tlc) protein mutant" XP002779167, retrieved from EBI accession No. GSP:BDJ69216, Database accession No. BDJ69216, Jan. 12, 2017.
Database Geneseq "Human tear lipocallin (Tlc) wild-type protein" XP002780278, retrieved from EBI accession No. GSP:AKT20280, Database accession No. AKT20280 sequence, Jan. 10, 2008.
Database Geneseq "Plasmid pTLpc3 fragment protein" XP002779168, retrieved from EBI accession No. GSP:ADA27294, Database accession No. ADA27294, Nov. 20, 2003.
Database USPTO Proteins "Sequence 52 from patent U.S. Pat. No. 7,893,208" XP002779169, retrieved from EBI accession No. AED49501, Apr. 10, 2011.
Dennis, M. et al., Albumin Binding as a General Strategy for Improving the Pharmacokinetics of Proteins, The Journal of Biological Chemistry, 277(38):35035-35043 (2002).
Flower, D. et al., The lipocalin protein family: structural and sequence overview, Biochimica et Biophys Acta, 1482:9-24 (2000).
Flower, Darren R., The lipocalin protein family: structure and function, Biochem. J., 1996, 318:1-14.
Fuerteges, F. and Abuchowski, A., The Clinical Efficacy of Poly(Ethylene Glycol)-Modified Proteins,: J. Control. Release, 1990, 11:139-148.
Huard, B. et al., Characterization of the major histocompatibility complex class II binding site on LAG-3 protein, Proc. Natl. Acad., Sci. USA, 94:5744-5749 (1997).
International Search Report and Written Opinion for PCT/EP2018/051139, dated May 7, 2018 (14 pages).
International Search Report and Written Opinion issued in corresponding application No. PCT/EP2016/066909 dated Dec. 9, 2016.
Kim, H. et al., High-Affinity Recognition of Lanthanide(III) Chelate Complexes by a Reprogrammed Human Lipocalin 2, J. Am. Chem. Soc., 2009, 131:3565-3576.
Kisielow, M. et al., Expression of lymphocyte activation gene 3 (LAG-3) on B cells is induced by T cells, European Journal of Immunology, 35:2081-2088 (2005).

Konig, T. and Skerra, A., Use of an albumin-binding domain for the selective immobilization of recombinant capture antibody fragments on ELISA plates, J. Immunol. Methods, 1998, 218:73-83.
Kouo et al., Galectin-3 Shapes Antitumor Immune Responses by Suppressing CDS+ T Cells via LAG-3 and Inhibiting Expansion of Plasmacytoid Dendritic Cells, Cancer Immunology Research, vol. 3, No. 4, 2015 pp. 412-423.
Lowman, H.B. Bacteriophage display and discovery of peptides leads for drug development, Annu. Rev. Biophys. Biomol. Struct., 1997, 26:401-424.
Macon-Lemaitre, L. and Triebel, F., The negative regulatory function of the lymphocyte-activation gene-3 co-receptor (CD223) on human T cells, Immunology, 115:170-178 (2005).
Osborn, B. et al., Pharmacokinetic and Pharmacodynamic Studies of a Human Serum Albumin-Interferon—Fusion Protein in Cynomolgus Monkeys, The Journal of Pharmacology and Experimental Therapeutics, 303(2):540-548 (2002).
Pervaiz, et al., Homology and Structure-Function Correlations Between α1-Acid Glycoprotein and Serum Retinol-Binding Protein and Its Relatives, 1987, The FASEB journal 1.3 (1987): 209-214.
Rodi, D. and Makowski, L., Phage-display technology—finding a needle in a vast molecular haystack, Curr. Opin. Biotechnol., 1999, 10:87-93.
Schmidt, T. et al., Molecular Interaction Between the Strep-tag Affinity Peptide and its Cognate Target, Streptavidin, J. Mol. Biol., 1996, 255:753-766.
Skerra, Arne, Lipocalins as a scaffold, Biochimica et Biophysica Acta, 2000, 1482:337-350.
Triebel, F. LAG-3, A Novel Lymphocyte Activation Gene Closely Related to CD4, J. Exp. Med., 171:1393-1405 (1990).
Vajo, Z. and Duckworth, W., Genetically Engineered Insulin Analogs: Diabetes in the New Millennium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Woo, S. et al., Immune Inhibitory Molecules LAG-3 and PD-1 Synergistically Regulate T-cell Function to Promote Tumoral Immune Escape, Cancer Research, 72(4):917-927 (2012).
Workman, C. et al., LAG-3 Regulates Plasmacytoid Dendritic Cell Homeostasis, The Journal of Immunology, 182:1885-1891 (2009).
Buisson, S. and Triebel, F., MHC class II engagement by its ligand LAG-3 (CD223) leads to a distinct pattern of chemokine and chemokine receptor expression by human dendritic cells, Vaccine, 21(9-10):862-8 (2003).
Flower, D. et al., Beyond the superfamily: the lipocalin receptors, Biochim Biophys Acta, 1482:327-336 (2000).

* cited by examiner

Figure 1

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|---|
| SEQ ID NO: 1 (human tear lipocalin) | H | H | L | L | A | S | D | E | E | I | Q | D | V | S | G | T | W | Y | L | K | A | M | T | V | D |
| SEQ ID NO: 3 (negative control lipocalin mutein) |  |  |  |  | A | S | D | E | E | I | Q | D | V | S | G | T | W | Y | L | K | A | M | T | V | D |
| SEQ ID NO: 4 (negative control lipocalin mutein) |  |  |  |  | A | S | D | E | E | I | Q | D | V | P | G | T | W | Y | L | K | A | M | T | V | D |
| SEQ ID NO: 7 |  |  |  |  | A | S | D | E | E | I | Q | D | V | S | G | T | W | Y | L | K | A | M | T | V | D |
| SEQ ID NO: 8 |  |  |  |  | T | S | D | Q | E | I | Q | D | V | S | G | T | W | Y | L | K | A | M | T | V | D |
| SEQ ID NO: 9 |  |  |  |  | T | S | D | E | E | I | Q | D | V | S | G | T | W | Y | L | K | A | M | T | V | D |
| SEQ ID NO: 10 |  |  |  |  | A | S | Q | E | E | I | Q | D | V | S | G | T | W | Y | L | K | A | M | T | V | D |
| SEQ ID NO: 11 |  |  |  |  | T | S | D | E | E | I | Q | D | V | S | G | T | W | Y | L | K | A | M | T | V | D |
| SEQ ID NO: 12 |  |  |  |  | A | S | D | E | E | I | Q | D | V | S | G | T | W | Y | L | K | A | M | T | V | D |
| SEQ ID NO: 13 |  |  |  |  | A | S | D | E | E | I | Q | D | V | S | G | M | W | Y | L | K | A | M | T | V | D |
| SEQ ID NO: 14 |  |  |  |  | A | S | D | E | E | I | Q | D | V | S | G | T | W | Y | L | K | A | M | T | V | D |
| SEQ ID NO: 15 |  |  |  |  | A | S | D | E | E | I | Q | D | V | S | G | T | W | Y | L | K | A | M | T | V | D |
| SEQ ID NO: 16 |  |  |  |  | T | S | D | E | E | I | Q | D | V | S | G | T | W | Y | L | K | A | M | T | V | D |
| SEQ ID NO: 17 |  |  |  |  | A | S | D | E | E | F | Q | D | V | S | G | T | W | Y | L | K | A | M | T | V | D |
| SEQ ID NO: 18 |  |  |  |  | T | S | D | Q | E | I | Q | D | V | S | G | T | W | Y | L | K | A | M | T | V | D |
| SEQ ID NO: 19 |  |  |  |  | A | S | D | E | E | I | Q | D | V | P | G | T | W | Y | L | K | A | M | T | V | S |
| SEQ ID NO: 20 |  |  |  |  | A | S | D | E | E | I | Q | D | V | P | G | T | W | Y | L | K | A | M | T | V | S |
| SEQ ID NO: 21 |  |  |  |  | A | S | D | E | E | I | Q | D | V | P | G | T | W | Y | L | K | A | M | T | V | S |
| SEQ ID NO: 22 |  |  |  |  | A | S | D | E | E | I | Q | D | V | P | G | T | W | Y | L | K | A | M | T | V | S |
| SEQ ID NO: 23 |  |  |  |  | A | S | D | E | E | I | Q | D | V | P | G | T | W | Y | L | K | A | M | T | V | S |
| SEQ ID NO: 24 |  |  |  |  | A | S | D | E | E | I | Q | D | V | P | G | T | W | Y | L | K | A | M | T | V | S |
| SEQ ID NO: 25 |  |  |  |  | A | S | D | E | E | I | Q | D | V | P | G | T | W | Y | L | K | A | M | T | V | S |
| SEQ ID NO: 26 |  |  |  |  | A | S | D | E | E | I | Q | D | V | P | G | T | W | Y | L | K | A | M | T | V | S |
| SEQ ID NO: 27 |  |  |  |  | A | S | D | E | E | I | Q | D | V | P | G | T | W | Y | L | K | A | M | T | V | S |
| SEQ ID NO: 28 |  |  |  |  | A | S | D | E | E | I | Q | D | V | P | G | T | W | Y | L | K | A | M | T | V | S |
| SEQ ID NO: 57 |  |  |  |  | T | S | D | Q | E | I | Q | D | V | S | G | T | W | Y | L | K | A | M | T | V | D |
| SEQ ID NO: 58 |  |  |  |  | T | S | R | D | Q | I | Q | R | V | S | G | T | W | Y | L | K | A | M | T | V | D |
| SEQ ID NO: 59 |  |  |  |  | T | S | R | D | R | I | Q | R | V | S | G | T | W | Y | L | K | A | M | T | V | D |
| SEQ ID NO: 60 |  |  |  |  | T | S | R | D | Q | I | Q | R | V | S | G | T | W | Y | L | K | A | M | T | V | D |
| SEQ ID NO: 61 |  |  |  |  | T | S | R | D | Q | I | Q | R | V | S | G | T | W | Y | L | K | A | M | T | V | D |
| SEQ ID NO: 62 |  |  |  |  | T | S | R | D | Q | I | Q | R | V | S | G | T | W | Y | L | K | A | M | T | V | D |
| SEQ ID NO: 63 |  |  |  |  | A | S | D | E | E | I | Q | D | V | S | G | T | W | Y | L | K | A | M | T | V | D |
| SEQ ID NO: 64 |  |  |  |  | A | S | D | E | E | I | Q | D | V | S | G | T | W | Y | L | K | A | M | T | V | D |
| SEQ ID NO: 65 |  |  |  |  | T | S | D | E | E | I | Q | D | V | S | G | T | W | Y | L | K | A | M | T | V | D |
| SEQ ID NO: 66 |  |  |  |  | A | S | D | E | E | I | Q | D | V | S | G | T | W | Y | L | K | A | M | T | V | D |
| SEQ ID NO: 67 |  |  |  |  | A | S | D | E | E | I | Q | D | V | S | G | T | W | Y | L | K | A | M | T | V | D |
| SEQ ID NO: 68 |  |  |  |  | T | S | D | E | E | I | Q | D | V | S | G | T | W | Y | L | K | A | M | T | V | D |
| SEQ ID NO: 69 |  |  |  |  | A | S | D | E | E | I | Q | R | V | S | G | T | W | Y | L | K | A | M | T | V | D |
| SEQ ID NO: 70 |  |  |  |  | A | S | D | E | E | I | Q | R | V | S | G | T | W | Y | L | K | A | M | T | V | D |

Figure 1 (cont.)

| | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 |
|---|---|---|---|---|---|---|---|---|---|---|---|---|---|---|---|---|---|---|---|---|---|---|---|---|---|---|---|---|---|---|
| SEQ ID NO: 1 | R | E | F | P | E | M | N | L | E | S | V | T | P | M | T | L | T | T | L | E | G | G | N | L | E | A | K | V | T | M |
| SEQ ID NO: 3 | R | E | C | P | E | M | N | L | E | S | V | T | P | M | T | L | T | T | L | E | G | G | N | L | E | A | K | V | T | M |
| SEQ ID NO: 4 | R | E | F | P | E | M | N | L | E | S | V | T | P | M | T | L | T | T | L | E | G | G | N | L | E | A | K | V | T | M |
| SEQ ID NO: 7 | S | D | C | F | W | M | D | D | V | S | V | T | P | M | T | L | T | T | L | E | G | G | N | L | E | A | K | V | T | M |
| SEQ ID NO: 8 | S | D | C | F | W | M | D | D | V | S | V | T | P | M | T | L | T | T | L | E | G | G | N | L | E | A | K | V | T | M |
| SEQ ID NO: 9 | S | D | C | F | W | M | D | D | V | S | V | T | P | M | T | L | T | T | L | E | D | G | N | L | E | A | K | V | T | M |
| SEQ ID NO: 10 | S | D | C | F | W | M | D | D | V | S | V | T | P | M | T | L | T | T | L | E | G | G | N | L | E | A | K | V | T | M |
| SEQ ID NO: 11 | S | D | C | F | W | M | D | D | V | S | V | T | P | M | T | L | T | T | L | E | G | G | N | L | E | A | K | A | T | M |
| SEQ ID NO: 12 | S | D | C | F | W | M | D | D | V | S | V | T | P | M | T | L | T | T | L | E | G | G | N | L | E | A | K | V | T | M |
| SEQ ID NO: 13 | S | D | C | F | W | M | D | D | V | S | V | T | P | M | T | L | T | T | H | E | G | G | N | L | E | A | K | V | T | M |
| SEQ ID NO: 14 | S | D | C | F | W | M | D | D | V | S | V | T | P | M | T | L | T | T | L | E | G | G | N | L | E | A | K | V | T | M |
| SEQ ID NO: 15 | S | D | C | F | W | M | D | D | V | S | V | T | P | M | T | L | T | T | L | E | G | G | N | L | E | A | K | V | T | M |
| SEQ ID NO: 16 | S | D | C | F | W | M | D | D | V | S | V | T | P | M | T | L | T | T | L | E | G | G | N | L | E | A | K | V | T | M |
| SEQ ID NO: 17 | S | D | C | F | W | M | D | D | V | S | V | T | P | M | T | L | T | T | L | E | G | G | N | L | E | A | K | V | T | M |
| SEQ ID NO: 18 | S | D | C | F | W | M | D | D | V | S | V | T | P | M | T | L | T | T | L | E | G | G | N | L | E | A | K | V | T | M |
| SEQ ID NO: 19 | S | E | D | P | E | M | M | L | E | S | V | T | P | M | T | L | T | T | L | E | G | G | N | L | E | A | R | V | T | V |
| SEQ ID NO: 20 | D | E | D | P | E | M | T | L | E | S | V | T | P | M | T | L | T | T | L | E | G | G | N | L | E | A | R | V | T | V |
| SEQ ID NO: 21 | E | E | D | P | E | L | T | L | E | S | V | T | P | M | T | L | T | T | L | E | G | G | N | L | E | A | R | V | T | V |
| SEQ ID NO: 22 | E | E | D | P | E | M | T | L | E | S | V | T | P | M | T | L | T | T | L | E | G | G | N | L | E | A | R | V | T | V |
| SEQ ID NO: 23 | D | E | D | P | E | M | T | L | E | S | V | T | P | M | T | L | T | T | L | E | G | G | N | L | E | A | R | V | T | V |
| SEQ ID NO: 24 | S | E | D | P | E | M | T | L | E | S | V | T | P | M | T | L | T | T | L | E | G | G | N | L | E | A | R | V | T | V |
| SEQ ID NO: 25 | A | E | D | P | E | M | T | L | E | S | V | T | P | M | T | L | T | T | L | E | G | G | N | L | E | A | R | V | T | V |
| SEQ ID NO: 26 | R | E | D | P | E | M | T | L | E | S | V | T | P | M | T | L | T | T | L | E | G | G | N | L | E | A | R | V | T | V |
| SEQ ID NO: 27 | S | E | D | P | E | L | T | L | E | S | V | T | P | M | T | L | T | T | L | E | G | G | N | L | E | A | R | V | T | V |
| SEQ ID NO: 28 | D | E | D | P | E | M | T | L | E | S | V | T | P | M | T | L | T | T | L | E | G | G | N | L | E | A | R | V | T | V |
| SEQ ID NO: 57 | S | D | C | F | W | M | D | D | V | S | V | T | P | M | T | L | T | T | L | R | G | G | N | L | E | A | K | V | T | M |
| SEQ ID NO: 58 | S | D | C | F | W | M | D | D | V | S | V | T | P | M | T | L | T | T | L | R | G | G | N | L | E | A | K | V | T | M |
| SEQ ID NO: 59 | S | D | C | F | W | M | D | D | V | S | V | T | P | M | T | L | T | T | L | R | G | G | N | L | E | A | K | V | T | M |
| SEQ ID NO: 60 | S | D | C | F | W | M | D | D | V | S | V | T | P | M | T | L | T | T | L | R | G | G | N | L | E | A | K | V | T | M |
| SEQ ID NO: 61 | S | D | C | F | W | M | D | D | V | S | V | T | P | M | T | L | T | T | L | R | G | G | N | L | E | A | K | V | T | M |
| SEQ ID NO: 62 | S | D | C | F | W | M | D | D | V | S | V | T | P | M | T | L | T | T | L | R | G | G | N | L | E | A | K | V | T | M |
| SEQ ID NO: 63 | S | D | C | F | W | M | D | D | V | S | V | T | P | M | T | L | T | T | L | R | G | G | N | L | E | A | K | V | T | M |
| SEQ ID NO: 64 | S | D | C | F | W | M | D | D | V | S | V | T | P | M | T | L | T | T | L | E | G | G | N | L | E | A | K | V | T | M |
| SEQ ID NO: 65 | S | D | C | F | W | M | D | D | V | S | V | T | P | M | T | L | T | T | L | E | G | G | N | L | E | A | K | V | T | M |
| SEQ ID NO: 66 | S | D | C | F | W | M | D | D | V | S | V | T | P | M | T | L | T | T | L | R | G | G | N | L | E | A | K | V | T | M |
| SEQ ID NO: 67 | S | D | C | F | W | M | D | D | V | S | V | T | P | M | T | L | T | T | L | E | G | G | N | L | E | A | K | V | T | M |
| SEQ ID NO: 68 | S | D | C | F | W | M | D | D | V | S | V | T | P | M | T | L | T | T | L | E | G | G | N | L | E | A | K | V | T | M |
| SEQ ID NO: 69 | S | D | C | F | W | M | D | D | V | S | V | T | P | M | T | L | T | T | L | E | G | G | N | L | E | A | K | V | T | M |
| SEQ ID NO: 70 | S | D | C | F | W | M | D | D | V | S | V | T | P | M | T | L | T | T | L | E | G | G | N | L | E | A | K | V | T | M |

Figure 1 (cont.)

| | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|---|---|---|---|---|---|
| SEQ ID NO: 1 | L | I | S | G | R | C | Q | E | V | K | A | V | L | E | K | T | D | E | P | G | K | Y | T | A | D | G | G | K | H | V |
| SEQ ID NO: 3 | L | I | S | G | R | S | Q | E | V | K | A | V | L | E | K | T | D | E | P | G | K | Y | T | A | D | G | G | K | H | V |
| SEQ ID NO: 4 | L | I | S | G | R | C | Q | E | V | K | A | V | L | E | K | T | D | E | P | G | K | Y | T | A | D | G | G | K | H | V |
| SEQ ID NO: 7 | D | I | F | G | F | W | Q | E | V | K | A | V | L | E | K | T | D | E | P | G | K | Y | T | A | D | G | G | K | H | V |
| SEQ ID NO: 8 | D | I | F | G | F | W | Q | E | V | E | A | V | L | S | K | T | D | E | P | G | K | Y | T | A | D | G | G | K | H | A |
| SEQ ID NO: 9 | D | I | F | G | F | W | Q | E | V | E | A | V | L | E | K | T | D | E | P | G | K | Y | T | A | D | G | G | K | H | A |
| SEQ ID NO: 10 | D | I | F | G | F | W | Q | E | V | K | A | V | L | E | K | T | D | E | P | G | K | Y | T | A | D | G | G | K | H | D |
| SEQ ID NO: 11 | D | I | F | G | F | W | Q | E | V | E | A | V | L | E | K | T | D | E | P | G | K | Y | T | T | D | G | G | K | H | V |
| SEQ ID NO: 12 | D | I | F | G | F | W | Q | D | V | K | A | V | L | E | K | T | D | E | P | G | K | Y | T | A | D | G | G | K | H | D |
| SEQ ID NO: 13 | D | I | F | G | F | W | Q | E | V | E | A | V | L | E | K | T | D | E | P | G | K | Y | T | A | D | G | G | K | H | V |
| SEQ ID NO: 14 | D | I | F | G | F | W | Q | D | V | E | A | V | L | E | K | T | D | E | P | G | K | Y | T | A | D | G | G | K | H | V |
| SEQ ID NO: 15 | D | I | F | G | F | W | Q | E | V | E | A | V | L | E | R | T | D | E | P | G | K | Y | T | A | D | G | G | K | H | V |
| SEQ ID NO: 16 | D | I | F | G | F | W | Q | E | V | E | A | V | L | E | K | T | D | E | P | G | K | Y | T | A | G | G | G | K | H | V |
| SEQ ID NO: 17 | D | I | F | G | F | W | Q | E | V | E | A | V | L | E | K | T | D | A | P | G | K | Y | T | A | D | G | G | K | H | V |
| SEQ ID NO: 18 | D | I | F | G | F | W | Q | E | V | A | V | L | S | K | T | D | E | P | G | K | Y | T | A | D | G | G | K | H | A | |
| SEQ ID NO: 19 | L | I | D | G | R | C | Q | E | V | K | E | V | L | E | K | T | D | E | P | G | K | Y | T | E | D | G | G | K | H | V |
| SEQ ID NO: 20 | L | I | D | G | R | C | Q | E | V | K | E | V | L | E | K | T | D | E | P | G | K | Y | T | E | D | G | G | K | Y | V |
| SEQ ID NO: 21 | L | I | D | G | R | C | Q | E | V | K | E | V | L | E | K | T | D | E | P | G | K | Y | T | E | D | G | G | K | V | V |
| SEQ ID NO: 22 | L | I | D | G | R | C | Q | E | V | K | E | V | L | E | K | T | D | E | P | G | K | Y | T | E | D | G | G | K | V | V |
| SEQ ID NO: 23 | L | I | D | G | R | C | Q | E | V | K | E | V | L | E | K | T | D | E | P | G | K | Y | T | E | D | G | G | K | Y | V |
| SEQ ID NO: 24 | L | I | D | G | R | C | Q | E | V | K | E | V | L | E | K | T | D | E | P | G | K | Y | T | E | D | G | G | K | Y | V |
| SEQ ID NO: 25 | L | I | D | G | R | C | Q | E | V | K | E | V | L | E | K | T | D | E | P | G | K | Y | T | E | D | G | G | K | Y | V |
| SEQ ID NO: 26 | L | I | D | G | R | C | Q | E | V | K | E | V | L | E | K | T | D | E | P | G | K | Y | T | E | D | G | G | K | H | V |
| SEQ ID NO: 27 | L | I | D | G | R | C | Q | E | V | K | E | V | L | E | K | T | D | E | P | G | K | Y | T | E | D | G | G | K | Y | V |
| SEQ ID NO: 28 | L | I | D | G | R | C | Q | E | V | K | E | V | L | E | K | T | D | E | P | G | K | Y | T | E | D | G | G | K | V | V |
| SEQ ID NO: 57 | D | I | F | G | F | W | Q | E | V | E | A | V | L | E | K | T | D | R | P | G | K | Y | T | A | G | G | G | K | H | A |
| SEQ ID NO: 58 | D | I | F | G | F | W | Q | E | V | E | A | V | L | E | K | T | R | R | P | G | K | Y | T | A | G | G | G | K | H | A |
| SEQ ID NO: 59 | D | I | F | G | F | W | Q | E | V | E | A | V | L | E | K | T | R | R | P | G | K | Y | T | A | G | G | G | K | H | A |
| SEQ ID NO: 60 | D | I | F | G | F | W | Q | E | V | E | A | V | L | E | K | T | R | R | P | G | K | Y | T | A | G | G | G | K | H | A |
| SEQ ID NO: 61 | D | I | F | G | F | W | Q | E | V | E | A | V | L | E | K | T | D | R | P | G | K | Y | T | A | G | G | G | K | H | A |
| SEQ ID NO: 62 | D | I | F | G | F | W | Q | E | V | E | A | V | L | E | K | T | R | R | P | G | K | Y | T | A | G | G | G | K | H | A |
| SEQ ID NO: 63 | D | I | F | G | F | W | Q | E | V | E | A | V | L | E | R | T | D | R | P | G | K | Y | T | A | G | G | G | K | H | V |
| SEQ ID NO: 64 | D | I | F | G | F | C | Q | E | V | E | A | V | L | E | R | T | D | E | P | G | K | Y | T | A | D | G | G | K | H | V |
| SEQ ID NO: 65 | D | I | F | G | F | W | Q | E | V | E | A | V | L | E | R | T | D | E | P | G | K | Y | T | A | D | G | G | K | H | V |
| SEQ ID NO: 66 | D | I | F | G | F | W | Q | D | V | E | A | V | L | E | K | T | D | R | P | G | K | Y | T | A | G | G | G | K | H | V |
| SEQ ID NO: 67 | D | I | F | G | F | C | Q | D | V | E | A | V | L | E | K | T | D | E | P | G | K | Y | T | A | D | G | G | K | H | V |
| SEQ ID NO: 68 | D | I | F | G | F | W | Q | D | V | E | A | V | L | E | K | T | D | E | P | G | K | Y | T | A | D | G | G | K | H | V |
| SEQ ID NO: 69 | D | I | F | G | F | W | Q | D | V | E | A | V | L | E | K | T | D | E | P | G | K | Y | T | A | D | G | G | K | H | V |
| SEQ ID NO: 70 | D | I | F | G | F | C | Q | D | V | E | A | V | L | E | K | T | D | E | P | G | K | Y | T | A | D | G | G | K | H | V |

Figure 1 (cont.)

| | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 |
|---|---|---|---|---|---|---|---|---|---|---|---|---|---|---|---|---|---|---|---|---|---|---|---|---|---|---|---|---|---|---|
| SEQ ID NO: 1  | A | Y | I | I | R | S | H | V | K | D | H | Y | I | F | Y | C | E | G | E | L | H | G | K | P | V | R | G | V | K | L |
| SEQ ID NO: 3  | A | Y | I | I | R | S | H | V | K | D | H | Y | I | F | Y | S | E | G | E | C | H | G | K | P | V | P | G | V | W | L |
| SEQ ID NO: 4  | A | Y | I | I | R | S | H | V | K | D | H | Y | I | F | Y | S | E | G | E | L | H | G | K | P | V | R | G | V | K | L |
| SEQ ID NO: 7  | A | Y | I | I | R | S | H | V | K | D | H | Y | I | F | Y | S | E | G | E | C | A | G | Y | P | V | P | G | V | W | L |
| SEQ ID NO: 8  | A | Y | I | I | R | S | H | V | K | D | H | Y | I | F | Y | S | E | G | E | C | A | G | Y | P | V | P | G | V | W | L |
| SEQ ID NO: 9  | A | Y | I | I | R | S | H | V | K | D | H | Y | I | F | Y | S | E | G | E | C | A | G | Y | P | V | P | G | V | W | L |
| SEQ ID NO: 10 | A | Y | I | I | R | S | H | V | K | D | H | Y | I | F | Y | S | E | G | E | C | A | G | Y | P | V | P | G | V | W | L |
| SEQ ID NO: 11 | A | Y | I | I | R | S | H | V | K | D | H | R | I | F | Y | S | E | G | E | C | A | G | Y | P | V | P | G | V | W | L |
| SEQ ID NO: 12 | A | Y | I | I | S | S | H | V | K | D | H | Y | I | F | Y | S | E | G | E | C | A | G | Y | P | V | P | G | V | W | L |
| SEQ ID NO: 13 | A | Y | I | S | R | S | H | V | K | D | H | Y | I | F | Y | S | E | G | E | C | A | G | Y | P | V | P | G | V | W | L |
| SEQ ID NO: 14 | A | Y | I | I | R | S | H | V | K | D | H | Y | I | F | Y | S | E | G | E | C | A | G | Y | P | V | P | G | V | W | L |
| SEQ ID NO: 15 | A | Y | I | I | R | S | H | V | K | D | H | Y | I | F | Y | S | E | G | E | C | A | G | Y | P | V | P | G | V | W | L |
| SEQ ID NO: 16 | A | Y | I | I | R | S | H | V | K | D | H | Y | V | F | Y | S | E | G | E | C | A | G | Y | P | V | P | G | V | W | L |
| SEQ ID NO: 17 | A | Y | I | I | R | S | H | E | K | D | H | Y | I | F | Y | S | E | G | E | C | A | G | Y | P | V | P | G | V | W | L |
| SEQ ID NO: 18 | A | Y | I | I | R | S | H | V | K | D | H | Y | I | F | Y | S | E | G | E | C | A | G | Y | P | V | P | G | V | W | L |
| SEQ ID NO: 19 | D | Y | I | I | R | S | H | V | K | D | H | Y | I | F | Y | F | E | G | E | C | Q | G | T | P | R | R | M | V | A | L |
| SEQ ID NO: 20 | D | Y | I | I | R | S | H | V | K | D | H | Y | I | F | Y | F | E | G | E | C | H | G | T | P | R | R | M | V | A | L |
| SEQ ID NO: 21 | D | Y | I | I | R | S | H | V | K | D | H | Y | I | F | Y | F | E | G | E | C | Q | G | T | P | R | R | M | V | A | L |
| SEQ ID NO: 22 | D | Y | I | I | R | S | H | V | K | D | H | Y | I | F | Y | F | E | G | E | C | E | G | T | P | R | R | V | V | A | L |
| SEQ ID NO: 23 | D | Y | I | I | R | S | H | V | K | D | H | Y | I | F | Y | F | E | G | E | C | Q | G | T | P | R | R | V | V | A | L |
| SEQ ID NO: 24 | D | Y | I | I | R | S | H | V | K | D | H | Y | I | F | Y | F | E | G | E | C | Q | G | T | P | R | R | M | V | A | L |
| SEQ ID NO: 25 | D | Y | I | I | R | S | H | V | K | D | H | Y | I | F | Y | F | E | G | E | C | R | G | T | P | R | R | M | V | A | L |
| SEQ ID NO: 26 | D | Y | I | I | R | S | H | V | K | D | H | Y | I | F | Y | F | E | G | E | C | Q | G | T | P | R | R | M | A | A | L |
| SEQ ID NO: 27 | D | Y | I | I | R | S | H | V | K | D | H | Y | I | F | Y | F | E | G | E | C | P | G | T | P | R | R | M | V | A | L |
| SEQ ID NO: 28 | D | Y | I | I | R | S | H | V | K | D | H | Y | I | F | Y | F | E | G | E | C | Q | G | T | P | R | R | M | I | A | L |
| SEQ ID NO: 57 | A | Y | I | I | R | S | H | V | K | D | H | Y | I | F | Y | S | E | G | E | C | A | G | Y | P | V | P | G | V | W | L |
| SEQ ID NO: 58 | A | Y | I | I | R | S | H | V | K | D | H | Y | I | F | Y | S | E | G | E | C | A | G | Y | P | V | P | G | V | W | L |
| SEQ ID NO: 59 | A | Y | I | I | R | S | H | V | K | R | H | Y | I | F | Y | S | E | G | E | C | A | G | Y | P | V | P | G | V | W | L |
| SEQ ID NO: 60 | A | Y | I | I | R | S | H | V | K | D | H | Y | I | F | Y | S | E | G | E | C | A | G | Y | P | V | P | G | V | W | L |
| SEQ ID NO: 61 | A | Y | I | I | R | S | H | V | K | D | H | Y | I | F | Y | S | E | G | E | C | A | G | Y | P | V | P | G | V | W | L |
| SEQ ID NO: 62 | A | Y | I | I | R | S | H | V | K | D | H | Y | I | F | Y | S | E | G | E | C | A | G | Y | P | V | P | G | V | W | L |
| SEQ ID NO: 63 | A | Y | I | I | R | S | H | V | K | D | H | Y | I | F | Y | S | E | G | E | C | A | G | Y | P | V | P | G | V | W | L |
| SEQ ID NO: 64 | A | Y | I | I | R | S | H | V | K | D | H | Y | I | F | Y | S | E | G | E | C | A | G | Y | P | V | P | G | V | W | L |
| SEQ ID NO: 65 | A | Y | I | I | R | S | H | V | K | D | H | Y | I | F | Y | S | E | G | E | C | A | G | Y | P | V | P | G | V | W | L |
| SEQ ID NO: 66 | A | Y | I | I | R | S | H | V | K | D | H | Y | I | F | Y | S | E | G | E | C | A | G | Y | P | V | P | G | V | W | L |
| SEQ ID NO: 67 | A | Y | I | I | R | S | H | V | K | D | H | Y | I | F | Y | S | E | G | E | C | A | G | Y | P | V | P | G | V | W | L |
| SEQ ID NO: 68 | A | Y | I | I | R | S | H | V | K | D | H | Y | I | F | Y | S | E | G | E | C | A | G | Y | P | V | P | G | V | W | L |
| SEQ ID NO: 69 | A | Y | I | I | R | S | H | V | K | D | H | Y | I | F | Y | S | E | G | E | C | A | G | Y | P | V | P | G | V | W | L |
| SEQ ID NO: 70 | A | Y | I | I | R | S | H | V | K | D | H | Y | I | F | Y | S | E | G | E | C | A | G | Y | P | V | P | G | V | W | L |

Figure 1 (Cont.)

| | 116 | 117 | 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 |
|---|---|---|---|---|---|---|---|---|---|---|---|---|---|---|---|---|---|---|---|---|---|---|---|---|---|---|---|---|---|---|
| SEQ ID NO: 1 | V | G | R | D | P | K | N | N | L | E | A | L | E | D | F | E | K | A | A | G | A | R | G | L | S | T | E | S | I | L |
| SEQ ID NO: 3 | V | G | R | D | P | K | N | N | L | E | A | L | E | D | F | E | K | A | A | G | A | R | G | L | S | T | E | S | I | L |
| SEQ ID NO: 4 | V | G | R | D | P | T | N | N | L | E | A | L | E | D | F | E | K | A | A | G | A | R | G | L | S | T | E | S | I | L |
| SEQ ID NO: 7 | V | G | R | D | P | K | N | N | L | E | A | L | E | D | F | E | K | A | A | G | A | R | G | L | S | T | E | S | I | L |
| SEQ ID NO: 8 | V | G | R | D | P | K | N | N | L | E | A | L | E | D | F | E | K | A | A | G | A | R | G | L | S | T | E | S | I | L |
| SEQ ID NO: 9 | V | G | R | D | P | K | N | N | L | E | A | L | E | D | F | E | K | A | A | G | A | R | G | L | S | T | E | S | I | L |
| SEQ ID NO: 10 | V | G | R | D | P | K | N | N | L | E | A | L | E | D | F | E | K | A | A | G | A | R | G | L | S | T | E | S | I | L |
| SEQ ID NO: 11 | V | G | R | D | P | K | N | N | L | E | A | L | E | D | F | E | K | A | A | G | A | R | G | L | S | T | E | S | I | L |
| SEQ ID NO: 12 | V | G | R | D | P | K | N | N | S | E | A | L | E | D | F | E | K | A | A | G | A | R | G | L | S | T | E | S | I | L |
| SEQ ID NO: 13 | V | G | R | D | P | K | N | N | L | E | A | L | E | D | F | E | K | A | A | G | A | R | G | L | S | T | E | S | I | L |
| SEQ ID NO: 14 | V | G | R | D | P | K | N | N | L | E | A | L | E | D | F | E | K | A | A | G | A | R | G | L | S | T | E | S | I | L |
| SEQ ID NO: 15 | V | G | R | D | P | K | N | N | L | E | A | L | E | D | F | E | K | A | A | G | A | R | G | L | S | T | E | S | I | L |
| SEQ ID NO: 16 | V | G | R | D | P | K | N | N | L | E | A | L | E | D | F | E | K | A | A | G | A | R | G | L | S | T | E | S | I | L |
| SEQ ID NO: 17 | V | G | R | D | P | K | N | N | L | E | A | L | E | D | F | E | K | A | A | G | A | R | G | L | S | T | E | S | I | L |
| SEQ ID NO: 18 | V | G | R | D | P | K | N | N | L | E | A | L | E | D | F | E | K | A | A | G | A | R | G | L | S | T | E | S | I | L |
| SEQ ID NO: 19 | V | G | R | D | P | T | N | N | L | E | A | L | E | D | F | E | K | A | A | G | A | R | G | L | S | T | E | S | I | L |
| SEQ ID NO: 20 | V | G | R | D | P | T | N | N | L | E | A | L | E | D | F | E | K | A | A | G | A | R | G | L | S | T | E | S | I | L |
| SEQ ID NO: 21 | V | G | R | D | P | T | N | N | L | E | A | L | E | D | F | E | K | A | A | G | A | R | G | L | S | T | E | S | I | L |
| SEQ ID NO: 22 | V | G | R | D | P | T | N | N | L | E | A | L | E | D | F | E | K | A | A | G | A | R | G | L | S | T | E | S | I | L |
| SEQ ID NO: 23 | V | G | R | D | P | T | N | N | L | E | A | L | E | D | F | E | K | A | A | G | A | R | G | L | S | T | E | S | I | L |
| SEQ ID NO: 24 | V | G | R | D | P | T | N | N | L | E | A | L | E | D | F | E | K | A | A | G | A | R | G | L | S | T | E | S | I | L |
| SEQ ID NO: 25 | V | G | R | D | P | T | N | N | L | E | A | L | E | D | F | E | K | A | A | G | A | R | G | L | S | T | E | S | I | L |
| SEQ ID NO: 26 | V | G | R | D | P | T | N | N | L | E | A | L | E | D | F | E | K | A | A | G | A | R | G | L | S | T | E | S | I | L |
| SEQ ID NO: 27 | V | G | R | D | P | T | N | N | L | E | A | L | E | D | F | E | K | A | A | G | A | R | G | L | S | T | E | S | I | L |
| SEQ ID NO: 28 | V | G | R | D | P | T | N | N | L | E | A | L | E | D | F | E | K | A | A | G | A | R | G | L | S | T | E | S | I | L |
| SEQ ID NO: 57 | V | G | R | D | P | K | N | N | L | E | A | L | E | D | F | E | K | A | A | G | A | R | G | L | S | T | E | S | I | L |
| SEQ ID NO: 58 | V | G | R | D | P | K | N | N | L | E | A | L | E | D | F | E | K | A | A | G | A | R | G | L | S | T | E | S | I | L |
| SEQ ID NO: 59 | V | G | R | D | P | K | N | N | L | E | A | L | E | D | F | E | K | A | A | G | A | R | G | L | S | T | E | S | I | L |
| SEQ ID NO: 60 | V | G | R | D | P | K | N | N | L | E | A | L | E | D | F | E | K | A | A | G | A | R | G | L | S | T | E | S | I | L |
| SEQ ID NO: 61 | V | G | R | D | P | K | N | N | L | E | A | L | E | D | F | E | K | A | A | G | A | R | G | L | S | T | E | S | I | L |
| SEQ ID NO: 62 | V | G | R | D | P | K | N | N | L | E | A | L | E | D | F | E | K | A | A | G | A | R | G | L | S | T | E | S | I | L |
| SEQ ID NO: 63 | V | G | R | D | P | K | N | N | L | E | A | L | E | D | F | E | K | A | A | G | A | R | G | L | S | T | E | S | I | L |
| SEQ ID NO: 64 | V | G | R | D | P | K | N | N | L | E | A | L | E | D | F | E | K | A | A | G | A | R | G | L | S | T | E | S | I | L |
| SEQ ID NO: 65 | V | G | R | D | P | K | N | N | L | E | A | L | E | D | F | E | K | A | A | G | A | R | G | L | S | T | E | S | I | L |
| SEQ ID NO: 66 | V | G | R | D | P | K | N | N | L | E | A | L | E | D | F | E | K | A | A | G | A | R | G | L | S | T | E | S | I | L |
| SEQ ID NO: 67 | V | G | R | D | P | K | N | N | L | E | A | L | E | D | F | E | K | A | A | G | A | R | G | L | S | T | E | S | I | L |
| SEQ ID NO: 68 | V | G | R | D | P | K | N | N | L | E | A | L | E | D | F | E | K | A | A | G | A | R | G | L | S | T | E | S | I | L |
| SEQ ID NO: 69 | V | G | R | D | P | K | N | N | L | E | A | L | E | D | F | E | K | A | A | G | A | R | G | L | S | T | E | S | I | L |
| SEQ ID NO: 70 | V | G | R | D | P | K | N | N | L | E | A | L | E | D | F | E | K | A | A | G | A | R | G | L | S | T | E | S | I | L |

| | 146 | 147 | 148 | 149 | 150 | 151 | 152 | 153 | 154 | 155 | 156 | 157 | 158 |
|---|---|---|---|---|---|---|---|---|---|---|---|---|---|
| SEQ ID NO: 1 | I | P | R | Q | S | E | T | C | S | P | G | S | D |
| SEQ ID NO: 3 | I | P | R | Q | S | E | T | S | S | P | G | | |
| SEQ ID NO: 4 | I | P | R | Q | S | E | T | C | S | P | G | | |
| SEQ ID NO: 7 | I | P | R | Q | S | E | T | G | S | P | G | | |
| SEQ ID NO: 8 | I | P | R | Q | S | E | T | S | A | P | G | | |
| SEQ ID NO: 9 | I | P | R | Q | N | E | T | S | S | P | G | | |
| SEQ ID NO: 10 | I | P | W | Q | S | E | P | S | S | P | G | | |
| SEQ ID NO: 11 | I | P | R | Q | S | E | T | S | S | P | G | | |
| SEQ ID NO: 12 | I | P | R | Q | S | E | T | S | S | P | G | | |
| SEQ ID NO: 13 | I | P | R | Q | S | E | T | S | S | P | G | | |
| SEQ ID NO: 14 | I | P | R | N | S | E | T | S | S | P | G | | |
| SEQ ID NO: 15 | I | P | R | Q | S | E | T | S | S | P | G | | |
| SEQ ID NO: 16 | I | P | R | Q | S | E | T | S | S | P | G | | |
| SEQ ID NO: 17 | I | P | R | Q | S | E | T | S | S | P | G | | |
| SEQ ID NO: 18 | I | P | R | Q | S | E | T | S | A | P | G | | |
| SEQ ID NO: 19 | I | P | R | Q | S | E | T | C | S | P | G | | |
| SEQ ID NO: 20 | I | P | R | Q | S | E | T | C | S | P | G | | |
| SEQ ID NO: 21 | I | P | R | Q | S | E | T | C | S | P | G | | |
| SEQ ID NO: 22 | I | P | R | Q | S | E | T | C | S | P | G | | |
| SEQ ID NO: 23 | I | P | R | Q | S | E | T | C | S | P | G | | |
| SEQ ID NO: 24 | I | P | R | Q | S | E | T | C | S | P | G | | |
| SEQ ID NO: 25 | I | P | R | Q | S | E | T | C | S | P | G | | |
| SEQ ID NO: 26 | I | P | R | Q | S | E | T | C | S | P | G | | |
| SEQ ID NO: 27 | I | P | R | Q | S | E | T | C | S | P | G | | |
| SEQ ID NO: 28 | I | P | R | Q | S | E | T | C | S | P | G | | |
| SEQ ID NO: 57 | I | P | R | Q | S | E | T | S | A | P | G | | |
| SEQ ID NO: 58 | I | P | R | Q | S | E | T | S | A | P | G | | |
| SEQ ID NO: 59 | I | P | R | Q | S | E | T | S | A | P | G | | |
| SEQ ID NO: 60 | I | P | R | Q | S | E | T | S | A | P | G | | |
| SEQ ID NO: 61 | I | P | R | Q | S | E | T | S | A | P | G | | |
| SEQ ID NO: 62 | I | P | R | Q | S | E | T | S | A | P | G | | |
| SEQ ID NO: 63 | I | P | R | Q | S | E | T | S | S | P | G | | |
| SEQ ID NO: 64 | I | P | R | Q | S | E | T | C | S | P | G | | |
| SEQ ID NO: 65 | I | P | R | Q | S | E | T | S | S | P | G | | |
| SEQ ID NO: 66 | I | P | R | N | S | E | T | S | S | P | G | | |
| SEQ ID NO: 67 | I | P | R | N | S | E | T | C | S | P | G | | |
| SEQ ID NO: 68 | I | P | R | N | S | E | T | S | S | P | G | | |
| SEQ ID NO: 69 | I | P | R | N | S | E | T | S | S | P | G | | |
| SEQ ID NO: 70 | I | P | R | N | S | E | T | C | S | P | G | | |

Figure 2A:
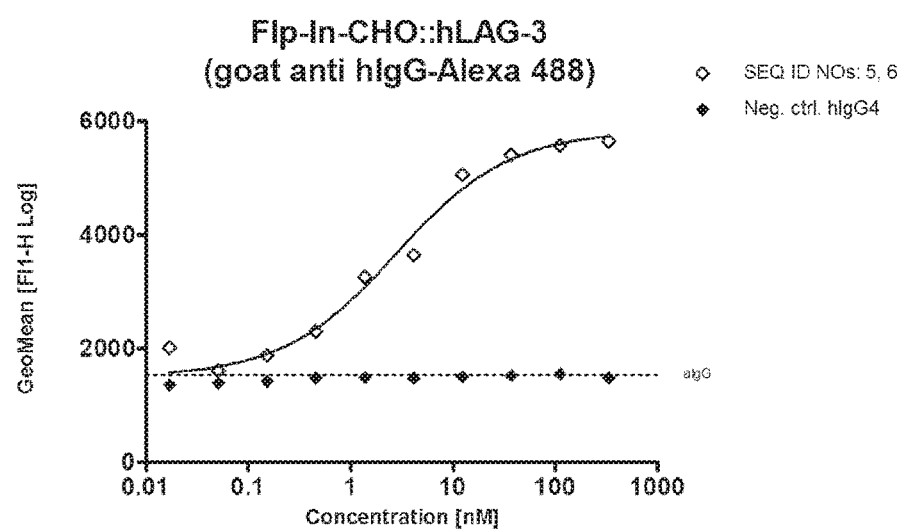
Figure 2B:
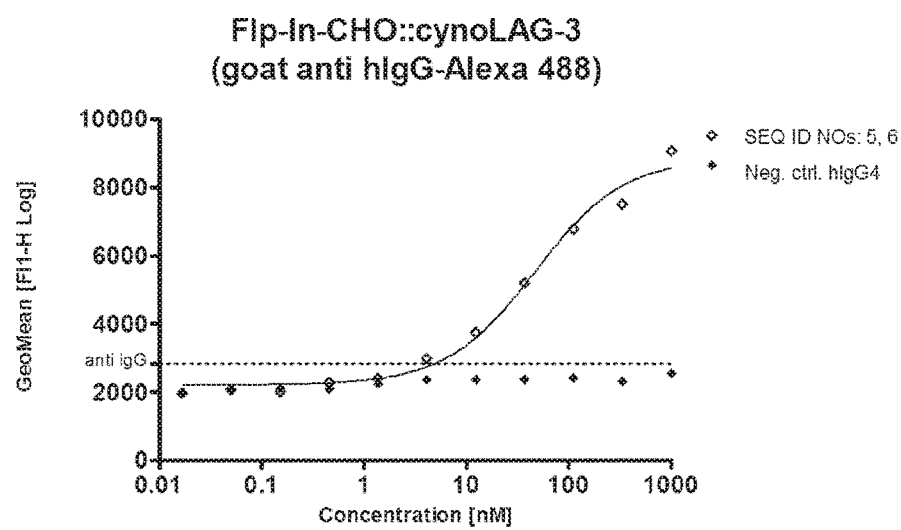

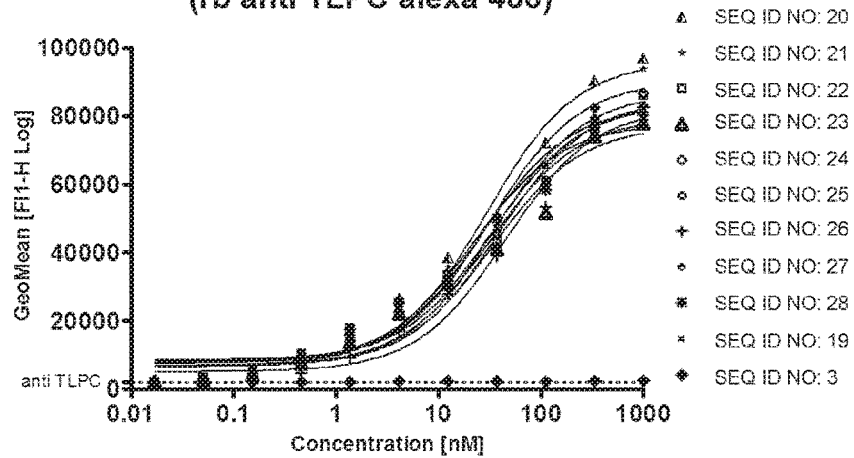
Figure 2B
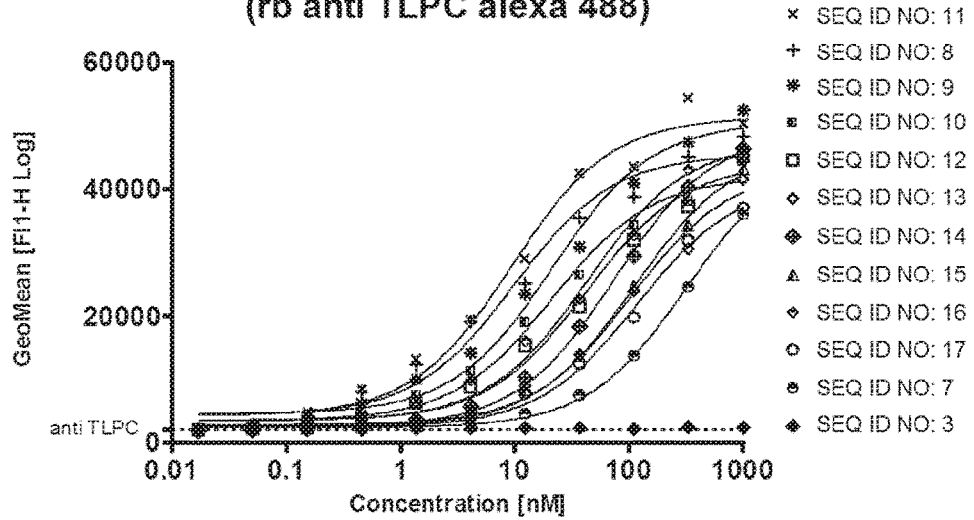

LIPOCALIN MUTEINS WITH BINDING AFFINITY FOR LAG-3

CROSS-REFERENCE TO RELATED APPLICATIONS

This application is a National Stage application of PCT/EP2018/051139, filed Jan. 18, 2018, which claims priority from European Application No. 17151945.7, filed Jan. 18, 2017, each of which are hereby incorporated by reference in their entireties.

SEQUENCE LISTING

The instant application contains a Sequence Listing, which has been submitted in ASCII format via EFS-WEB and is hereby incorporated by reference in its entirety. Said ASCII copy, created on Jul. 11, 2019, is named "Sequence_Listing.txt" and is 120 KB in size.

I. BACKGROUND

Lymphocyte Activation Gene-3, or LAG-3 (also known as Cluster of Differentiation 223 or CD223) is a membrane protein of the immunoglobulin supergene family. LAG-3 is structurally and genetically related to CD4, with its encoding gene located on the distal part of the short arm of chromosome 12, near the CD4 gene, suggesting that the LAG-3 gene may have evolved through gene duplication (Triebel et al., J Exp Med, 1990). LAG-3 is not expressed on resting peripheral blood lymphocytes but is expressed on activated T cells and natural killer (NK) cells (Triebel et al., J Exp Med, 1990), and has been reported to also be expressed on activated B cells (Kisielow et al., Eur J Immunol, 2005) and plasmacytoid dendritic cells (Workman et al., J Immunol, 2009).

Like CD4, LAG-3 binds to major histocompatibility complex (MHC) class II molecules, but with a higher affinity and at a different binding site (Huard et al., Proc Natl Acad Sci USA, 1997). MHC class II engagement on dendritic cells by LAG-3 leads to changes in the cytokine and chemokine profiles of dendritic cells (Buisson and Triebel, Vaccine, 2003). Further, LAG-3 has been reported to cause maturation of dendritic cells, as demonstrated by the production of IL-12 and TNF-alpha by these cells and increases in the capacity of dendritic cells to stimulate the proliferation and IFN-gamma response by allogeneic T-cells (Andreae et al., J Immunol, 2002). LAG-3 signaling and MHC class II cross-linking has been reported to inhibit early events in primary activation of human $CD4^+$ and $CD8^+$ T-cells (Macon-Lemaitre and Triebel, Immunology, 2005). It negatively regulates the cellular proliferation, activation, and homeostasis of T cells.

Like CTLA-4 and PD-1, LAG-3 is an inhibitory immune receptor. LAG-3's prominent role as a negative regulator of T cell responses has been impressively demonstrated in particular in conjunction with PD-1 in a study based on both knockout mice and target-specific antibodies (Woo et al., Cancer Res, 2012). In this study, dual anti-LAG-3/anti-PD-1 antibody treatment cured most mice of established tumors that were largely resistant to single antibody treatment. Further, LAG-3/PD-1 double knock-out mice showed markedly increased survival from and clearance of multiple transplantable tumors. Further strong experimental support for the powerful combined role of PD-1 and LAG-3 as immune checkpoints was provided by the fact that the double knock-out mice were highly prone to lethal autoinflammation.

Consequently, there exists an unmet need in the art for compounds that modulate responses of $LAG-3^+$ lymphocytes, such as T-cells, NK cells, B cells, and plasmacytoid dendritic cells, which may have important uses in the treatment or prevention of cancer, organ transplant rejection, or treatment of autoimmune or autoinflammatory diseases. It is further desirable to have lipocalin muteins that are capable of binding LAG-3 with high affinity, that have enhanced biostability, and that can be used in pharmaceutical and/or diagnostic applications. In this regard, it is an object of the present disclosure to provide such lipocalin muteins. No such lipocalin muteins having these high binding affinities and enhanced biostability features have been previously described.

In addition, it has been regarded as natural that monkey metabolism is the most similar to that of humans, and, accordingly, cynomolgus monkeys have been widely used in pharmacokinetic or drug-safety studies in the development of new therapies, including new biologics. Such studies may further be necessary prerequisites to regulatory approval. Thus, it is also desirable to have lipocalin muteins that are cross-reactive with both human and cynomolgus LAG-3, with comparable binding pattern, including comparable or similar binding affinity. No such lipocalin muteins having these cross-reactivity features have been previously described.

The recitation of any reference in this application is not an admission that the reference is prior art to this application.

In this regard, the present disclosure provides a group of novel compounds specifically binding to the LAG-3 of both humans and cynomolgus monkeys with high affinity and with enhanced biostability features, thereby, modulating the immune response. Such compounds are muteins derived from lipocalins and may be used in pharmaceutical, diagnostic or other applications. Muteins of lipocalins are a rapidly expanding class of therapeutics and can be constructed to exhibit high affinity and specificity against desired targets (see, e.g., International Patent Publication Nos. WO 99/16873, WO 00/75398, WO 03/029471, and WO 05/19256).

II. DEFINITIONS

The following list defines terms, phrases, and abbreviations used throughout the instant specification. All terms listed and defined herein are intended to encompass all grammatical forms.

As used herein, unless otherwise specified, "LAG-3" means human LAG-3 (huLAG-3) and includes variants, isoforms and species homologs of human LAG-3. LAG-3 is also known as "lymphocyte-activation gene 3", "cluster of differentiation 223" or "CD223", which are used interchangeably. Human LAG-3 means a full-length protein defined by UniProt P18627 (version 5 of 7 Jul. 2009), a fragment thereof, or a variant thereof. Cynomolgus LAG-3 (cyLAG-3) refers to the LAG-3 of cynomolgus monkeys. CyLAG-3 may also be used to refer to the extracellular domain of cyLAG-3 as set forth in position 1-428 of SEQ ID NO: 56.

As used herein, "detectable affinity" means the ability to bind to a selected target with an affinity, generally measured by $K_d$ or $EC_{50}$, of at most about $10^{-5}$ M or below (a lower $K_d$ or $EC_{50}$ value reflects better binding activity). Lower affinities are generally no longer measurable with common methods such as ELISA (enzyme-linked immunosorbent assay) and therefore of secondary importance.

As used herein, "binding affinity" of a protein of the disclosure (e.g., a mutein of a lipocalin) or a fusion polypeptide thereof to a selected target (in the present case, LAG-3), can be measured (and thereby $K_d$ values of a mutein-ligand complex can be determined) by a multitude of methods known to those skilled in the art. Such methods include, but are not limited to, fluorescence titration, competitive ELISA, calorimetric methods, such as isothermal titration calorimetry (ITC), and surface plasmon resonance (SPR). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_d$ (for example fluorescence titration, competition ELISA or surface plasmon resonance, just to name a few) or even the mathematical algorithm which is used for evaluation of the experimental data.

Therefore, it is also clear to the skilled person that the $K_d$ values (dissociation constant of the complex formed between the respective binder and its target/ligand) may vary within a certain experimental range, depending on the method and experimental setup that is used for determining the affinity of a particular lipocalin mutein for a given ligand. This means that there may be a slight deviation in the measured $K_d$ values or a tolerance range depending, for example, on whether the $K_d$ value was determined by surface plasmon resonance (SPR), by competitive ELISA, or by direct ELISA.

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. Said term also includes fragments of a mutein and variants as described herein. Lipocalin muteins of the present invention, fragments or variants thereof preferably have the function of binding to LAG-3 as described herein.

The term "fragment" as used herein in connection with the muteins of the disclosure relates to proteins or peptides derived from full-length mature human tear lipocalin (hTlc or hTLPC) that is N-terminally and/or C-terminally shortened, i.e., lacking at least one of the N-terminal and/or C-terminal amino acids. Such a fragment may lack up to 2, up to 3, up to 4, up to 5, up to 10, up to 15, up to 20, up to 25, or up to 30 (including all numbers in between) of the N-terminal and/or C-terminal amino acids. As an illustrative example, such a fragment may lack 4 N-terminal and 2 C-terminal amino acids. It is understood that the fragment is preferably a functional fragment of the full-length tear lipocalin (mutein), which means that it preferably comprises the binding pocket of the full-length tear lipocalin (mutein) it is derived from. As an illustrative example, such a functional fragment may comprise at least amino acids 5-156 of the linear polypeptide sequence of native mature human tear lipocalin. Such fragments may include at least 10, more such as 20 or 30 or more consecutive amino acids of the primary sequence of mature tear lipocalin and are usually detectable in an immunoassay of the mature lipocalin.

In general, the term "fragment," as used herein with respect to the corresponding protein ligand LAG-3 of a lipocalin mutein of the disclosure or of the combination according to the disclosure or of a fusion protein described herein, relates to N-terminally and/or C-terminally shortened protein or peptide ligands, which retain the capability of the full-length ligand to be recognized and/or bound by a mutein according to the disclosure.

The term "mutagenesis" as used herein means that the experimental conditions are chosen such that the amino acid naturally occurring at a given sequence position of the mature lipocalin can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild-type protein. Such an insertion or deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. International Patent Publication No. WO 2005/019256 which is incorporated by reference its entirety herein).

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin muteins of the disclosure).

The percentage of sequence homology or sequence identity can, for example, be determined herein using the program BLASTP, version blastp 2.2.5 (Nov. 16, 2002) (cf. Altschul et al., Nucleic Acids Res, 1997). In this embodiment, the percentage of homology is based on the alignment of the entire polypeptide sequence (matrix: BLOSUM 62; gap costs: 11.1; cut-off value set to $10^{-3}$) including the propeptide sequences, preferably using the wild-type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a lipocalin (mutein) is different from a wild-type lipocalin corresponding to a certain position in the amino acid sequence of a wild-type lipocalin, a skilled artisan can use means and methods well-known in the art, e.g., alignments, either manually or by using computer programs such as BLAST 2.0, which stands for Basic Local Alignment Search Tool, or ClustalW, or any other suitable program which is suitable to generate sequence alignments. Accordingly, a wild-type sequence of lipocalin can serve as "subject sequence" or "reference sequence," while the amino acid sequence of a lipocalin different from the wild-type lipocalin described herein serves as "query sequence." The terms "wild-type sequence" and "reference sequence" and "subject sequence" are used interchangeably herein. A preferred wild-type sequence of lipocalin is the sequence of hTlc as shown in SEQ ID NO: 1.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example BLAST (Altschul, et al. (1997) *Nucleic Acids Res.* 25, 3389-3402), Blast2 (Altschul, et al. (1990) *J. Mol. Biol.* 215, 403-410), and Smith-Waterman (Smith, et al. (1981) *J. Mol. Bol.* 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e., an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. The term "variant," as used herein with respect to the corresponding protein target LAG-3 of a lipocalin mutein of the disclosure or of a combination and/or a fusion protein according to the disclosure, relates to LAG-3 or fragment thereof, that has one or more such as 1, 2, 3, 4, 5, 6, 7, 8, 9, 10, 12, 14, 16, 18, 20, 22, 24, 26, 28, 30, 40, 50, 60, 70, 80 or more amino acid substitutions, deletions and/or insertions in comparison to a wild-type LAG-3 protein, such as a LAG-3 reference protein as deposited with UniProt as described herein. A LAG-3 variant has preferably an amino acid identity of at least 50%, 60%, 70%, 80%, 85%, 90% or 95% with a wild-type LAG-3, such as a human LAG-3 reference protein as deposited with UniProt as described herein.

By a "native sequence" of a lipocalin is meant that the sequence of a lipocalin that has the same amino acid sequence as the corresponding polypeptide derived from nature. Thus, a native sequence lipocalin can have the amino acid sequence of the respective naturally-occurring lipocalin from any organism, in particular, a mammal. Such native sequence polypeptide can be isolated from nature or can be produced by recombinant or synthetic means. The term "native sequence" polypeptide specifically encompasses naturally-occurring truncated or secreted forms of the lipocalin, naturally-occurring variant forms such as alternatively spliced forms and naturally-occurring allelic variants of the lipocalin. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally, a variant has at least about 70%, including at least about 80%, such as at least about 85% amino acid sequence identity, including at least about 90% amino acid sequence identity or at least about 95% amino acid sequence identity with the native sequence polypeptide. As an illustrative example, the first 4 N-terminal amino acid residues (His-His-Leu-Leu, SEQ ID NO: 51) and the last 2 C-terminal amino acid residues (Ser-Asp) can be deleted or mutated in a hTlc mutein of the disclosure without affecting the biological function of the protein, e.g., SEQ ID NOs: 7-28, 57-70, and 85-95.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sequence positions of one or more lipocalin muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild-type lipocalin 5'-untranslated region (UTR) including the promoter and/or any other regulatory sequences or gene (including exons and introns).

Thus, for a "corresponding position" in accordance with the disclosure, it is preferably to be understood that the positions of nucleotides/amino acids may differ in the indicated number than similar neighboring nucleotides/amino acids, but said neighboring nucleotides/amino acids, which may be exchanged, deleted, or added, are also comprised by the one or more "corresponding positions".

In addition, for a corresponding position in a lipocalin mutein based on a reference sequence in accordance with the disclosure, it is preferably understood that the positions of nucleotides/amino acids structurally correspond to the positions elsewhere in a (mutant or wild-type) lipocalin, even if they may differ in the indicated number, as appreciated by the skilled in light of the highly-conserved overall folding pattern among lipocalins.

The term "albumin" includes all mammal albumins such as human serum albumin or bovine serum albumin or rat serum albumin.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2,000 Daltons, preferably between 100 and 1,000 Daltons, and optionally including one or two metal atoms.

The word "detect," "detection," "detectable," or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgus monkeys, to name only a few illustrative examples. Preferably, the "mammal" herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

III. DESCRIPTIONS OF FIGURES

FIG. 1: depicts an alignment of amino acid sequences of optimized LAG-3 specific human tear lipocalin (hTlc) muteins, in comparison with the linear polypeptide sequence of mature hTlc. Compared to the linear polypeptide sequence of mature hTlc (SEQ ID NO: 1), the first 4 N-terminal amino acid residues (His, His, Leu, Leu; SEQ ID NO: 50) and the last 2 C-terminal amino acid residues (Ser, Asp) are deleted in these hTlc-derived, LAG-3-binding muteins (listed as hTlc muteins SEQ ID NOs: 7-28 and 57-70) and the negative-control muteins (SEQ ID NOs: 3 and 4).

FIG. 2: depicts the results of fluorescence-activated cell sorting (FACS) studies carried out in order to assess the specific binding of the lipocalin muteins to human LAG-3 (FIG. 2A) and cynomolgus LAG-3 (FIG. 2B), respectively, expressed on mammalian cells as described in Example 5. Chinese hamster ovary (CHO) cells stably transfected with human or cynomolgus LAG-3 were incubated with lipocalin muteins, and the bound muteins were detected using a fluorescently labeled anti-hTlc antibody. All lipocalin muteins show binding to LAG-3 expressed on CHO cells with $EC_{50}$ comparable to tested benchmark antibody (SEQ ID NOs: 5 and 6). The negative lipocalin mutein SEQ ID NO: 3 and negative control human IgG4 (hIgG4) (SEQ ID NOs: 55 and 56, Sigma #14639) showed no binding. The geometric means of the fluorescence intensity were normalized to the maximal mean and fit with a 1:1 binding model. The resulting $EC_{50}$ values are provided in Table 3.

Figure 3:
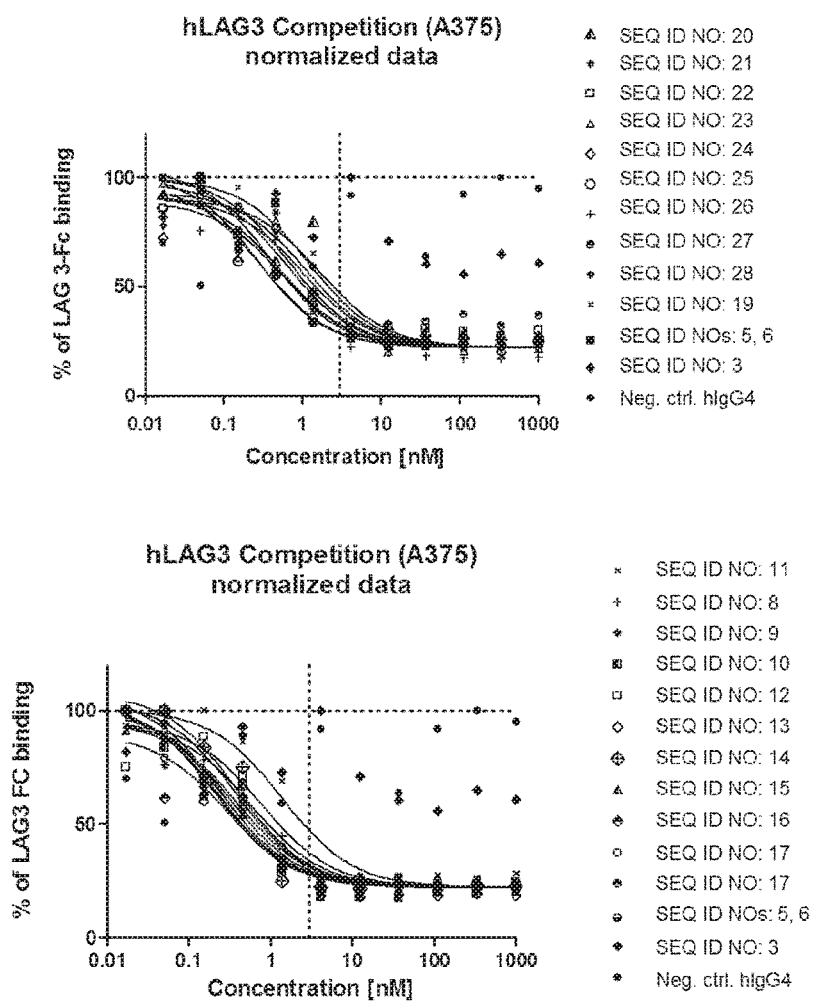

FIG. 3: shows that lipocalin muteins compete with major histocompatibility complex (MHC) class II molecules (LAG-3's natural ligands) for the binding to LAG-3 in a competitive FACS experiment. MHC class II positive human cell line A375 was incubated with lipocalin mutein and huLAG-3-Fc (human LAG-3 extracellular domain fused to human IgG1 Fc fragment, R&D systems), the bound huLAG-3-Fc was detected using a goat anti-human IgG antibody conjugated with phycoerythrin (Jackson ImmunoResearch Laboratories Inc., #109-1 16-098). A dose dependent inhibition of huLAG-3-Fc binding to MHC class II molecules by LAG-3 specific lipocalin muteins was shown. The LAG-3 specific lipocalin muteins and the reference molecule (SEQ ID NOs: 5 and 6) showed inhibitory effect on LAG-3/MHC class II binding at equal concentrations. The negative control lipocalin mutein (SEQ ID NO: 3) and hIgG4 negative control did not lead to measurable inhibition of huLAG-3-Fc binding to A375 cells expressing MHC class II molecules.

IV. DETAILED DESCRIPTION OF THE DISCLOSURE

As used herein, a "lipocalin" is defined as a monomeric protein of approximately 18-20 kDa in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Skerra, Biochim Biophys Acta, 2000, Flower et al., Biochim Biophys Acta, 2000, Flower, Biochem J, 1996). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art (see, e.g., U.S. Pat. No. 7,250,297).

As noted above, a lipocalin is a polypeptide defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to lipocalin muteins having a cylindrical β-pleated sheet supersecondary structural region comprising eight β-strands connected pair-wise by four loops at one end to define thereby a binding pocket, wherein at least one amino acid of each of at least three of said four loops has been mutated as compared to the reference sequence, and wherein said lipocalin is effective to bind LAG-3 with detectable affinity.

In one particular embodiment, a lipocalin mutein disclosed herein is a mutein of human tear lipocalin (hTlc or hTLPC), also termed lipocalin-1, human tear prealbumin or von Ebner gland protein. The term "human tear lipocalin" or "hTlc" or "lipocalin-1" as used herein refers to the mature human tear lipocalin with the SWISS-PROT/UniProt Data Bank Accession Number P31025 (Isoform 1). The amino acid sequence shown in SWISS-PROT/UniProt Data Bank Accession Number P31025 may be used as a preferred "reference sequence," more preferably the amino acid sequence shown in SEQ ID NO: 1 is used herein as "reference sequence."

In some embodiments, a lipocalin mutein binding LAG-3 with detectable affinity may include at least one amino acid substitution of a native cysteine residue of the reference sequence by another amino acid, for example, a serine residue. In some other embodiments, a lipocalin mutein binding LAG-3 with detectable affinity may include one or more non-native cysteine residues substituting one or more amino acids of a wild-type lipocalin. In a further particular embodiment, a lipocalin mutein according to the disclosure includes at least two amino acid substitutions of a native amino acid by a cysteine residue, hereby to form one or more cysteine bridges. In some embodiments, said cysteine bridge may connect at least two loop regions. The definition of these regions is used herein in accordance with Flower (Biochem J, 1996), (Biochim Biophys Acta, 2000) and Breustedt et al. (J Biol Chem, 2005). In a related embodiment, the disclosure teaches one or more lipocalin muteins that are capable of activating downstream signaling pathways of LAG-3 by binding to LAG-3.

Proteins of the disclosure, which are directed against or specific for LAG-3, include any number of specific-binding protein muteins that are based on a defined protein scaffold, preferably a lipocalin scaffold. Also preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50, with 1, 2, 3, 4, 5, 6, 7, 8, 9, 10, or 11 being preferred and 9, 10 or 11 being even more preferred. However, it is preferred that protein muteins of the disclosure is still capable of binding LAG-3.

In one aspect, the present disclosure includes various lipocalin muteins that bind LAG-3 with at least detectable affinity. In this sense, LAG-3 can be regarded as a non-natural ligand of wild-type lipocalins, where "non-natural ligand" refers to a compound that does not bind to wild-type lipocalin under physiological conditions. By engineering wild-type lipocalin with one or more mutations at certain sequence positions, the present inventors have demonstrated that high affinity and high specificity for the non-natural ligand, LAG-3, is possible. In some embodiments, at 1, 2, 3, 4, 5, 6, 7, 8, 9, 10, 11, 12, or even more nucleotide triplet(s) encoding certain sequence positions on wild type lipocalins, random mutagenesis may be carried out through substitution at these positions by a subset of nucleotide triplets.

Further, the lipocalin muteins of the disclosure may have a mutated amino acid residue at any one or more, including at least at any 1, 2, 3, 4, 5, 6, 7, 8, 9, 10, 11, 12, or more of the sequence positions corresponding to certain sequence positions of the linear polypeptide sequence of the reference lipocalin.

A protein of the disclosure may include the wild-type (natural) amino acid sequence of the "parental" protein scaffold (such as a lipocalin scaffold) outside the mutated amino acid sequence positions. In some embodiments, a lipocalin mutein according to the disclosure may also carry one or more amino acid mutations at one or more sequence position(s) as long as such a mutation does, at least essentially not hamper or not interfere with the binding activity and the folding of the mutein. Such mutations can be accomplished very easily on DNA level using established standard methods (Sambrook and Russell, 2001, Molecular cloning: a laboratory manual). Illustrative examples of alterations of the amino acid sequence are insertions or deletions as well as amino acid substitutions. Such substitutions may be conservative, i.e., an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the reference lipocalin, preferably as hTlc, as long as these deletions or insertion result in a stable, folded and functional mutein. In such mutein, for instance, one or more amino acid residues are added or deleted at the N- or C-terminus of the polypeptide (for example, hTlc muteins with truncated N- and C-terminus). Generally, such a mutein may have about at least 70%, including at least about 80%, such as at least about 85% amino acid sequence identity, with the amino acid sequence of hTlc (SEQ ID NO: 1). As an illustrative example, the present disclosure also encompasses hTlc muteins as defined above, in which the first four N-terminal amino acid residues of the sequence of mature human tear lipocalin (His-His-Leu-Leu; SEQ ID NO: 51; positions 1-4) and/or the last two C-terminal amino acid residues (Ser-Asp; positions 157-158) of the linear polypeptide sequence of the mature human tear lipocalin have been deleted (see, e.g., SEQ ID Nos: 7-28, 57-70, and 85-95).

The amino acid sequence of a lipocalin mutein disclosed herein has a high sequence identity to the reference lipocalin, preferably hTlc, when compared to sequence identities with other lipocalins. In this general context, the amino acid sequence of a lipocalin mutein of the disclosure is at least substantially similar to the amino acid sequence of the reference lipocalin, with the proviso that possibly there are gaps (as defined below) in an alignment that are the result of additions or deletions of amino acids. A respective sequence of a lipocalin mutein of the disclosure, being substantially similar to the sequences of the reference lipocalin, has, in some embodiments, at least 70% identity or sequence homology, at least 75% Identity or sequence homology, at least 80% Identity or sequence homology, at least 82% identity or sequence homology, at least 85% identity or sequence homology, at least 87% identity or sequence homology, or at least 90% identity or sequence homology including at least 95% Identity or sequence homology, to the sequence of the reference lipocalin, with the proviso that the altered position or sequence is retained and that one or more gaps are possible.

As used herein, a lipocalin mutein of the disclosure "specifically binds" a target (for example, LAG-3) if it is able to discriminate between that target and one or more reference targets, since binding specificity is not an absolute, but a relative property. "Specific binding" can be determined, for example, in accordance with western blots, ELISA, FACS, RIA (radioimmunoassay), ECL (electrochemiluminescence), IRMA (immunoradiometric assay), IHC (Immunohistochemistry), and peptide scans.

In one embodiment, the lipocalin muteins of the disclosure are fused at its N-terminus and/or its C-terminus to a fusion partner, which is a protein domain that extends the serum half-life of the mutein. In further particular embodiments, the protein domain is an Fc part of an immunoglobulin, a $C_H3$ domain of an immunoglobulin, a $C_H4$ domain of an immunoglobulin, an albumin binding peptide or an albumin binding protein.

In another embodiment, the lipocalin muteins of the disclosure are conjugated to a compound that extends the serum half-life of the mutein. More preferably, the muteins are conjugated to a compound selected from the group consisting of a polyalkylene glycol molecule, a hydroxyethyl starch, an Fc part of an immunoglobulin, a $C_H3$ domain of an immunoglobulin, a $C_H4$ domain of an immunoglobulin, an albumin binding peptide, and an albumin binding protein.

In yet another embodiment, the current disclosure relates to nucleic acid molecules comprising nucleotide sequences encoding lipocalin muteins disclosed herein. The disclosure encompasses a host cell containing said nucleic acid molecule.

A. Lipocalin Muteins Specific for LAG-3

In one aspect, the present disclosure provides human lipocalin muteins that bind to human LAG-3 with high affinity and useful applications of such muteins. The disclosure also provides methods of making LAG-3 binding proteins described herein as well as compositions comprising such proteins. LAG-3 binding proteins of the disclosure, as well as compositions thereof, may be used in methods of detecting LAG-3 protein in a sample or in methods of binding of LAG-3 in a subject to stimulate or inhibit immune responses. The disclosed LAG-3 binding proteins have enhanced biostability and have a similar or comparable binding pattern to both human and cynomolgus LAG-3. Finally, the disclosure provides methods of using the muteins of lipocalin against LAG-3 to inhibit the binding of LAG-3 to major histocompatibility complex (MHC) class II molecules. No such human lipocalin muteins having these features attendant to the uses provided by present disclosure have been previously described.

1. Exemplary Lipocalin Muteins Specific for LAG-3.

Some embodiments of the current disclosure relate to a lipocalin mutein that is capable of binding LAG-3, preferably human LAG-3 (huLAG-3), with an affinity measured by a $K_d$ of about 80 nM, 60 nM, 40 nM, 20 nM, 15 nM, 10 nM, 8 nM, 6 nM, 4 nM, 2 nM, 1.5 nM, 1 nM, 0.2 nM, 0.1 nM, 0.05 nM, or even lower. Such affinity can be determined, for example, by surface plasmon resonance (SPR) analysis essentially described in Example 4.

In other embodiments, the LAG-3 binding lipocalin mutein may be cross-reactive with cynomolgus LAG-3 (cyLAG-3), and in some further embodiments, capable of binding cyLAG-3 with an affinity measured by a $K_d$ of about 80 nM, 70 nM, 60 nM, 50 nM, 40 nM, 30 nM, 20 nM, 10 nM, 5 nM, 4 nM, 3 nM, 2 nM, 1 nM, 0.5 nM, or even lower such as about 0.46 nM. Such affinity can be determined, for example, by SPR analysis essentially described in Example 4.

In other embodiments, the lipocalin mutein is capable of binding LAG-3 on Chinese hamster ovary (CHO) cells transfected with huLAG-3 with an $EC_{50}$ value of about 5 nM, 4 nM, 3 nM, 2.5 nM, 2 nM, 1.5 nM, 1 nM, 0.5 nM or even lower such as about 0.22 nM or 0.02 nM. In other embodiments, the lipocalin mutein is capable of binding LAG-3 on CHO cells transfected with cyLAG-3 with an $EC_{50}$ of about 350 nM, 300 nM, 250 nM, 200 nM, 150 nM, 100 nM, 50 nM, 20 nM, 10 nM, or even lower such as about 9.3 nM. The $EC_{50}$ value can, for example, be determined by a fluorescence-activated cell sorting (FACS) as essentially described in Example 5.

In some embodiments, the lipocalin mutein is capable of inhibiting the binding of LAG-3 to MHC class II, such as those expressed on antigen-presenting cells (APCs) or tumor cells. The inhibitory mode of action can, for example, be determined by a FACS analysis as essentially described in Example 6.

In one aspect, the present disclosure provides LAG-3-binding hTlc muteins.

In this regard, the disclosure provides one or more hTlc muteins that are capable of binding LAG-3 with an affinity measured by a $K_d$ of about 10 nM or lower, 5 nM or lower, 4 nM or lower, 3 nM or lower, 2 nM or lower, 1.5 nM or lower, 1 nM or lower, 0.75 nM or lower, 0.5 nM or lower, 0.25 nM or lower, 0.1 nM or lower, or even about 0.05 nM or lower.

In some embodiments, such hTlc mutein comprises mutated amino acid residue(s) at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more positions corresponding to positions 5, 7-8, 10, 14, 16, 25-34, 44, 46, 52-53, 55-56, 58, 60-61, 63, 65-66, 69-70, 73, 79-80, 84-86, 89-90, 93, 96-98, 101, 105-106, 108, 110-114, 121, 124, 148-150, and 152-154 of the linear polypeptide sequence of mature hTlc (SEQ ID NO: 1).

In some particular embodiments, such hTlc muteins may contain mutated amino acid residue(s) at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more positions corresponding to positions 5, 7-8, 10, 16, 26-34, 44, 46, 53, 56, 58, 60-61, 63, 65, 69-70, 73, 79-80, 85, 89-90, 93, 96-98, 101, 105-106, 108, 111, 114, 124, 148-150, and 152-154 of the linear polypeptide sequence of mature hTlc (SEQ ID NO: 1).

In some particular embodiments, such hTlc muteins may contain mutated amino acid residue(s) at 1, 2, 3, 4, 5, 6, 7, 8, 9, 10, 11, 12, 13, 14, 15, 16, 17, 18, 19, 20, 21, or 22 positions corresponding to positions 14, 25-26, 28, 31-32, 52, 55, 58, 66, 79, 84, 86, 101, 105-106, 108, 110, 112-114, and 121 of the linear polypeptide sequence of mature hTlc (SEQ ID NO: 1).

In some particular embodiments, such hTlc muteins may include mutated amino acid residue(s) at 1, 2, 3, 4, 5, 6, 7, 8, 9, 10, 11, 12, 13, 14, 15, 16, 17, 18, 19, 20, 21, 22, 23, 24, 25, or 26 positions corresponding to positions 5, 8, 26-34, 56, 58, 60-61, 65, 69, 85, 101, 105-106, 108, 111, 114, and 153-154 of the linear polypeptide sequence of mature hTlc (SEQ ID NO: 1).

In some particular embodiments, such hTlc muteins may include mutated amino acid residue(s) 1, 2, 3, 4, 5, 6, 7, 8, 9, 10, 11, 12, 13, 14, 15, 16, 17, 18, 19, or 20 positions corresponding to positions 14, 25-26, 28, 32, 52, 55, 58, 66, 79, 84, 86, 101, 105, 106, 108, 110, 112, 114, and 121 of the linear polypeptide sequence of mature hTlc (SEQ ID NO: 1).

In some particular embodiments, such hTlc muteins may include mutated amino acid residue(s) 1, 2, 3, 4, 5, 6, 7, 8, 9, 10, 11, 12, 13, 14, 15, 16, 17, 18, 19, 20, 21, or 22 positions corresponding to positions 26-34, 56, 58, 60-61, 65, 70, 101, 105-106, 108, 111, 114, and 153 of the linear polypeptide sequence of mature hTlc (SEQ ID NO: 1).

In some particular embodiments, such hTlc muteins may include mutated amino acid residue(s) 1, 2, 3, 4, 5, 6, 7, 8, 9, 10, 11, 12, 13, 14, 15, 16, 17, 18, 19, or 20 positions corresponding to positions 26-34, 56, 58, 60-61, 63, 65, 101, 105-106, 108, 111, 114, 149, and 153 of the linear polypeptide sequence of mature hTlc (SEQ ID NO: 1).

In some particular embodiments, such hTlc muteins may include mutated amino acid residue(s) at 1, 2, 3, 4, 5, 6, 7, 8, 9, 10, 11, 12, 13, 14, 15, 16, 17, 18, 19, 20, 21, 22, 23, 24, 25, 26, or 27 positions corresponding to positions 5, 7-8, 10, 16, 44, 46, 63, 65, 69-70, 73, 80, 84, 89-90, 93, 96-98, 113, 124, 148-150, 152, or 154 of the linear polypeptide sequence of mature hTlc (SEQ ID NO: 1).

In some further embodiments, the hTlc muteins may comprise at least 1, 2, 3, 4, 5, or 6 mutated amino acid residue(s) at one or more sequence positions corresponding to sequence positions 5, 8, 65, 69, 85, and 154 of the linear polypeptide sequence of mature hTlc (SEQ ID NO: 1), and wherein said polypeptide binds LAG-3, in particular huLAG-3.

In some further embodiments, the hTlc muteins may comprise at least 1, 2, or 3 mutated amino acid residue(s) at one or more sequence positions corresponding to sequence positions 63, 65, and 149 of the linear polypeptide sequence of mature hTlc (SEQ ID NO: 1), and wherein said polypeptide binds LAG-3, including huLAG-3.

In some further embodiments, the hTlc muteins may comprise at least 1, 2, 3, or 4 mutated amino acid residue(s) at one or more sequence positions corresponding to sequence positions 26, 84, 106, and 112 of the linear polypeptide sequence of mature hTlc (SEQ ID NO: 1), and wherein said polypeptide binds LAG-3, including huLAG-3.

In some still further embodiments, the disclosure relates to a polypeptide, wherein said polypeptide is a hTlc mutein, in comparison with the linear polypeptide sequence of hTlc (SEQ ID NO: 1), comprising at least 1 mutated amino acid residue(s) at the sequence position 84, and wherein said polypeptide binds LAG-3, in particular huLAG-3.

In some embodiments, a lipocalin mutein according to the disclosure may include at least one amino acid substitution of a native cysteine residue by, e.g., a serine residue. In some embodiments, a hTlc mutein according to the disclosure includes an amino acid substitution of a native cysteine residue at positions 61 and/or 153 by another amino acid such as a serine residue. In this context it is noted that it has been found that removal of the structural disulfide bond (on the level of a respective naïve nucleic acid library) of wild-type tear lipocalin that is formed by the cysteine residues 61 and 153 (cf. Breustedt et al., J Biol Chem, 2005) may provide hTlc muteins that are not only stably folded but are also able to bind a given non-natural ligand with high affinity. In some particular embodiments, the hTlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp, and/or Cys 153→Ser or Ala. Such substitutions have proven useful to prevent the formation of the naturally occurring disulphide bridge linking Cys 61 and Cys 153, and thus to facilitate handling of the mutein. However, hTlc muteins that bind LAG-3 and that have the disulphide bridge formed between Cys 61 and Cys 153 are also part of the present disclosure.

In some embodiments, the elimination of the structural disulfide bond may provide further advantage of allowing for the (spontaneous) generation or deliberate introduction of non-natural artificial disulfide bonds into muteins of the disclosure, thereby increasing the stability of the muteins. For example, in some embodiments, either two or all three of the cysteine codons at position 61, 101 and 153 are replaced by a codon of another amino acid. Further, in some embodiments, a hTlc mutein according to the disclosure includes an amino acid substitution of a native cysteine residue at position 101 by a serine residue or a histidine residue.

However, hTlc muteins that bind LAG-3 and that have the disulfide bridge formed between Cys 61 and Cys 153 are also part of the present disclosure. In some particular embodiments, hTlc muteins that do not include mutated amino acids at positions 61 and 153 and have the disulfide bond formed between Cys 61 and Cys 153. In some further particular embodiments, the hTlc muteins with mutated amino acid(s) at position(s) 61 and/or 153 are subjected to further mutagenesis to restore the natural disulfide bond by back mutating positions 61 and/or 153 to the native cysteine.

In some embodiments, a mutein according to the disclosure includes an amino acid substitution of a native amino acid by a cysteine residue at positions 28 or 105 with respect to the amino acid sequence of hTlc (SEQ ID NO: 1).

Further, in some embodiments, a mutein according to the disclosure includes an amino acid substitution of a native arginine residue at positions 111 by a proline residue with respect to the amino acid sequence of hTlc (SEQ ID NO: 1). Further, in some embodiments, a mutein according to the disclosure includes an amino acid substitution of a native lysine residue at positions 114 by a tryptophan residue or a glutamic acid with respect to the amino acid sequence of hTlc (SEQ ID NO: 1).

In some embodiments, a lipocalin mutein according to the disclosure may include one or more amino acid mutated to an asparagine residue to introduce one or more glycosylation sites. In some preferred embodiments, a mutein according to the disclosure includes an amino acid mutation at position 12 of the linear polypeptide sequence of mature hTlc (SEQ ID NO: 1). For example, a mutein according to the disclosure may have the following mutated amino acid residue with respect to the amino acid sequence of hTlc (SEQ ID NO: 1): Asp 12→Asn.

In some embodiments, a mutein according to the disclosure includes an amino acid substitution at position 5 of the linear polypeptide sequence of mature hTlc (SEQ ID NO: 1). For example, a mutein according to the disclosure may have the following mutated amino acid residue with respect to the amino acid sequence of hTlc (SEQ ID NO: 1): Ala 5→Thr.

Further, in some embodiments, a mutein according to the disclosure may include at least one amino acid substitution of a native negatively charged residue by neutural residue, wherein the native negatively charged residue is not involved in binding to LAG-3, and wherein the substitution results in an increased isoelectric point (pI) of the mutein. In some particular embodiments, such native negatively charged residues and positions include Asp 7, Glu 9, Asp 12, Glu 45, Asp 72, Glu 73, Asp 80, and Asp 95 with respect to the amino acid sequence of hTlc (SEQ ID NO: 1). In some particular embodiments, such neutural amino acid residues include Asn, Arg, and Lys. In some further particular embodiments, a mutein according to the disclosure includes one or more of the following mutated amino acid residues at position 7, 9, 12, 45, 72, 73, 80, and 95 of the linear polypeptide sequence of mature hTlc (SEQ ID NO: 1): Asp 7→Asn, Arg, or Lys; Glu 9→Gln, Arg, or Lys; Asp 12→Asn or Arg; Glu 45→Arg; Asp 72→Asn, Arg, or Lys; Glu 73→Arg; Asp 80→Gly; and Asp 95→Asn, Arg, or Lys. Exemplary muteins include SEQ ID NOs: 57-60, 63, 66.

In some embodiments, a LAG-3-binding hTlc mutein according to the disclosure includes, at one or more positions corresponding to positions 5, 7-8, 10, 14, 16, 25-34, 44, 46, 52-53, 55-56, 58, 60-61, 63, 65-66, 69-70, 73, 79-80, 84-86, 89-90, 93, 96-98, 101, 105-106, 108, 110-114, 121, 124, 148-150, and 152-154 of the linear polypeptide sequence of mature hTlc (SEQ ID NO: 1), one or more of the following mutated amino acid residues: Ala 5→Thr; Asp 7→Gly; Glu 8→Gln; Ile 10→Phe; Ser 14→Pro; Thr 16→Met; Asp 25→Ser; Arg 26→Ser, Asp, Glu, Ala, or Gly; Glu 27→Asp; Phe 28→Cys or Asp; Pro 29→Phe; Glu 30→Trp; Met 31→Ile or Leu; Asn 32→Asp, Met, or Thr; Leu 33→Asp; Glu 34→Val; Leu 44→His; Gly 46→Asp; Lys 52→Arg; Val 53→Ala; Met 55→Val; Leu 56→Asp; Ser 58→Phe or Asp; Arg 60→Phe; Cys 61→Trp; Glu 63→Asp; Lys 65→Glu; Ala 66→Asn; Glu 69→Gly; Lys 70→Arg; Glu 73→Ala; Ala 79→Thr or Glu; Asp 80→Gly; His 84→Tyr or Leu; Val 85→Ala or Asp; Ala 86→Asp; Ile 89→Ser or Asn; Arg 90→Ser; Val 93→Glu: His 96→Asn; Tyr 97→His; Ile 98→Val; Cys 101→Ser or Phe; Leu 105→Cys or Gly; His 106→Ala, Gln, Glu, Lys, or Pro; Lys 108→Tyr or Thr; Val 110→Gly or Asn; Arg 111→Pro; Gly 112→Met, Val, or Leu; Val 113→Ala or Leu; Lys 114→Trp or Ala; Lys 121→Thr; Leu 124→Gln; Arg 148→Trp; Gln 149→Leu; Ser 150→Gly; Thr 152→Pro; Cys 153→Ser; and Ser 154→Ala. In some embodiments, a hTlc mutein according to the disclosure includes two or more, such as 3, 4, 5, 6, 7, 8, 9, 10, 11, 12, or even more such as 13, 14, 15, 16, 17, 18, 19, 20, 21, 22, 23, 24, 25, 26, 27 or even more mutated amino acid residues at these sequence positions of mature hTlc (SEQ ID NO: 1).

In some embodiments, a LAG-3-binding hTlc mutein according to the disclosure includes, at one or more positions corresponding to positions 14, 25-26, 28, 31-32, 52, 55, 58, 66, 79, 84, 86, 101, 105-106, 108, 110, 112-114, and 121 of the linear polypeptide sequence of mature hTlc (SEQ ID NO: 1), one or more of the following mutated amino acid residues: Ser 14→Pro; Asp 25→Ser; Arg 26→Ser, Asp, Glu, Ala, or Gly; Phe 28→Asp; Met 31→Leu; Asn 32→Met or Thr; Lys 52→Arg; Met 55→Val; Ser 58→Asp; Ala 66→Asn; Ala 79→Glu; His 84→Tyr or Leu; Ala 86→Asp; Cys 101→Phe; Leu 105→, Gly; His 106→Gln, Glu, Lys, or Pro; Lys 108→Thr; Val 110→Gly or Asn; Gly 112→Met, Val, or Leu; Val 113→Ala or Leu; Lys 114→Ala; Lys 121→Thr. In some embodiments, a hTlc mutein according to the disclosure includes two or more, such as 3, 4, 5, 6, 7, 8, 9, 10, 11, 12, or even more such as 13, 14, 15, 16, 17, 18, 19, 20, 21, or 22 mutated amino acid residues at these sequence positions of mature hTlc (SEQ ID NO: 1).

In some embodiments, a LAG-3-binding hTlc mutein according to the disclosure includes, at one or more positions corresponding to positions 5, 7-8, 10, 16, 26-34, 44, 46, 53, 56, 58, 60-61, 63, 65-66, 69-70, 73, 79-80, 85, 89-90, 93, 96-98, 101, 105-106, 108, 110-111, 114, 121, 124, 148-150, and 152-154 of the linear polypeptide sequence of mature hTlc (SEQ ID NO: 1), one or more of the following mutated amino acid residues: Ala 5→Thr; Asp 7→Gly; Glu 8→Gln; Ile 10→Phe; Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 44→His; Gly 46→Asp; Val 53→Ala; Leu 56→Asp; Ser 58→Phe; Arg 60→Phe; Cys 61→Trp; Glu 63→Asp; Lys 65→Glu; Glu 69→Gly; Lys 70→Arg; Glu 73→Ala; Ala 79→Thr; Asp 80→Gly; Val 85→Ala or Asp; Ile 89→Ser or Asn; Arg 90→Ser; Val 93→Glu; His 96→Asn; Tyr 97→His; Ile 98→Val; Cys 101→Ser; Leu 105→Cys; His 106→Ala; Lys 108→Tyr; Arg 111→Pro; Lys 114→Trp; Leu 124→Gln; Arg 148→Trp; Gin 149→Leu; Ser 150→Gly: Thr 152→Pro; Cys 153→Ser; and Ser 154→Ala. In some embodiments, a hTlc mutein according to the disclosure includes two or more, such as 3, 4, 5, 6, 7, 8, 9, 10, 11, 12, or even more such as 13, 14, 15, 16, 17, 18, 19, 20, 21, 22, 23, 24, 25, 26, 27 or even more mutated amino acid residues at these sequence positions of mature hTlc (SEQ ID NO: 1).

In some embodiments, a LAG-3-binding hTlc mutein according to the disclosure includes, at one or more positions corresponding to positions 5, 7-8, 10, 16, 26-34, 44, 46, 53, 56, 58, 60-61, 63, 65, 69-70, 73, 79-80, 85, 89-90, 93, 96-98, 101, 105-106, 108, 111, 114, 124, 148-150, and 152-154 of the linear polypeptide sequence of mature hTlc (SEQ ID NO: 1), one or more of the following mutated amino acid residues: Ala 5→Thr; Asp 7→Gly; Glu 8→Gln; Ile 10→Phe; Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 44→His; Gly 46→Asp; Val 53→Ala; Leu 56→Asp; Ser 58→Phe; Arg 60→Phe; Cys 61→Trp; Glu 63→Asp; Lys 65→Glu; Glu 69→Gly; Lys 70→Arg; Glu 73→Ala; Ala 79→Thr; Asp 80→Gly; Val 85→Ala or Asp; Ile 89→Ser or Asn; Arg 90→Ser; Val 93→Glu; His 96→Asn; Tyr 97→His; Ile 98→Val; Cys 101→Ser; Leu 105→Cys; His 106→Ala; Lys 108→Tyr; Arg 111→Pro; Lys 114→Trp; Leu 124→Gln; Arg 148→Trp; Gin 149→Leu; Ser 150→Gly; Thr 152→Pro; Cys 153→Ser; and Ser 154→Ala. In some embodiments, a hTlc mutein according to the disclosure includes two or more, such as 3, 4, 5, 6, 7, 8, 9, 10, 11, 12, or even more such as 13, 14, 15, 16, 17, 18, 19, 20, 21, 22, 23, 24, 25, 26, 27 or even more mutated amino acid residues at these sequence positions of mature hTlc (SEQ ID NO: 1).

In some embodiments, the LAG-3 binding hTlc muteins include the following amino acid mutations in comparison with the linear polypeptide sequence of mature hTlc (SEQ ID NO: 1): Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Cys 101→Ser Leu 105→Cys; His 106→Ala; Lys 108→Tyr; Arg 111→Pro; Lys 114→Trp; Cys 153→Ser; and further one or more, including 2, 3, 4, 5, 6, or 7, or even more, of the following amino acid mutations: Ala 5→Thr; Asp 7→Gly; Glu 8→Gln; Ile 10→Phe; Thr 16→Met; Leu 44→His; Gly 46→Asp; Val 53→Ala; Glu 63→Asp; Lys 65→Glu; Glu 69→Gly; Lys 70→Arg; Glu 73→Ala; Ala 79→Thr; Asp 80→Gly; Val 85→Ala or Asp; Ile 89→Ser or Asn; Arg 90→Ser; Val 93→Glu; His 96→Asn; Tyr 97→His; Ile 98→Val; Leu 124→Gln; Arg 148→Trp; Gin 149→Leu; Ser 150→Gly; Thr 152→Pro; and Ser 154→Ala.

In some embodiments, the LAG-3 binding hTlc muteins include the following amino acid mutations in comparison with the linear polypeptide sequence of mature hTlc (SEQ ID NO: 1): Ser 14→Pro; Asp 25→Ser; Phe 28→Asp; Lys 52→Arg; Met 55→Val; Ser 58→Asp; Ala 66→Asn; Ala 79→Glu; Ala 86→Asp; Cys 101→Phe; Leu 105→Gly; Lys 108→Thr; Lys 114→Ala; Lys 121→Thr; and one or more, including 2, 3, 4, 5, 6, 7, or even more, of the following amino acid mutations: Arg 26→Ser, Asp, Glu, Ala, or Gly; Met 31→Leu; Asn 32→Thr; Leu 56→Asp; His 84→Tyr or Leu; His 106→Gln, Glu, Lys, or Pro; Val 110→Gly or Asn; Gly 112→Met, Val or Leu; Val 113→Ala or Leu.

In some embodiments, the LAG-3 binding hTlc muteins include the following amino acid mutations in comparison with the linear polypeptide sequence of mature hTlc (SEQ ID NO: 1): Ser 14→Pro; Asp 25→Ser; Phe 28→Asp; Lys 52→Arg; Met 55→Val; Ser 58→Asp; Ala 66→Asn; Ala 79→Glu; Ala 86→Asp; Cys 101→Phe; Leu 105→Gly; Lys 108→Thr; Lys 114→Ala; Lys 121→Thr: and one or more, including 2, 3, 4, 5, 6, 7, or even more, of the following amino acid mutations: Arg 26→Ser, Asp, Glu, Ala, or Gly; Met 31→Leu; Asn 32→Thr; His 84→Tyr or Leu; His 106→Gln, Glu, Lys, or Pro; Val 110→Gly or Asn; Gly 112→Met, Val or Leu; Val 113→Ala or Leu.

In some embodiments, the LAG-3 binding hTlc muteins include the following amino acid mutations in comparison with the linear polypeptide sequence of mature hTlc (SEQ ID NO: 1): Ser 14→Pro; Asp 25→Ser; Phe 28→Asp; Lys 52→Arg; Met 55→Val; Ser 58→Asp; Ala 66→Asn; Ala 79→Glu; Ala 86→Asp; Cys 101→Phe; Leu 105→Gly; Lys 108→Thr, Lys 114→Ala; Lys 121→Thr; and one or more, including 2, 3, 4, 5, 6, 7, or even more, of the following amino acid mutations: Arg 26→Ser, Asp, Glu, or Ala; Met 31→Leu; Asn 32→Thr; Leu 56→Asp; His 84→Tyr or Leu; His 106→Glu, Lys, or Pro; Val 110→Asn; Gly 112→Val or Leu; Val 113→Ala or Leu.

In some additional embodiments, the LAG-3 binding hTlc muteins include one of the following sets of amino acid mutations in comparison with the linear polypeptide sequence of mature hTlc (SEQ ID NO: 1):

(a) Ala 5→Thr Glu 8→Gln; Arg 26→Ser Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 69→Gly; Val 85→Ala; Cys 101→Ser; Leu 105→Cys; His 106 Ala; Lys 108→Tyr; Arg 111→Pro; Lys 114→Trp; Cys 153→Ser; and Ser 154→Ala;

(b) Ala 5→Thr; Arg 26→Ser, Glu 27→Asp; Phe 28→Cys; Pro 29→Phe; Glu 30→Trp; Met 31→Ile; Asn 32→Asp; Leu 33→Asp; Glu 34→Val; Gly 46→Asp; Leu 56→Asp; Ser 58→Phe; Arg 60→Phe; Cys 61→Trp; Lys 65→Glu; Val 85→Ala; Cys 101→Ser; Leu 105→Cys; His 106→Ala; Lys 108→Tyr; Arg 111→Pro; Lys 114→Trp; Ser 150→Gly; and Cys 153→Sert;

(c) Asp 7→Gly; Arg 26→Ser, Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Val 85→Asp; Cys 101→Ser; Leu 105→Cys; His 106→Ala; Lys 108→Tyr; Arg 111→Pro; Lys 114→Trp; Arg 148→Trp; Thr 152→Pro; and Cys 153→Ser;

(d) Ala 5→Thr; Arg 26→Ser, Glu 27→Asp; Phe 28→Cys; Pro 29→Phe; Glu 30→Trp; Met 31→Ile; Asn 32→Asp; Leu 33→Asp; Glu 34→Val; Val 53→Ala; Leu 56 Asp; Ser 58→Phe; Arg 60→Phe; Cys 61→Trp; Lys 65→Glu; Ala 79→Thr; Tyr 97→His; Cys 101→Ser; Leu 105→Cys; His 106→Ala; Lys 108→Tyr; Arg 111→Pro; Lys 114→Trp; and Cys 153→Ser;

(e) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60-4 Phe; Cys 61→Trp; Glu 63→Asp; Val 85→Asp; Arg 90→Ser; His 96→Asn; Cys 101→Ser; Leu 105→Cys; His 106→Ala; Lys 108→Tyr; Arg 111→Pro; Lys 114→Trp; Leu 124→Gn; and Cys 153→Ser;

(f) Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 44→His; Leu 56→Asp; Ser 58→Phe; Arg 60→Phe; Cys 61→Trp; Lys 65→Glu; Ile 89→Ser; Cys 101→Ser; Leu 105→Cys; His 106→Ala; Lys 108→Tyr; Arg 111→Pro; Lys 114→Trp; and Cys 153→Ser;

(g) Arg 26→Ser; Glu 27→Asp; Phe 28→Cys: Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Lys 65→Glu; Cys 101→Ser; Leu 105→Cys; His 106→Ala; Lys 108→Tyr; Arg 111→Pro; Lys 114→Trp; Gin 149→Leu; and Cys 153→Ser;

(h) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Lys 70→Arg; Cys 101→, Ser; Leu 105→Cys; His 106→Ala; Lys 108→Tyr; Arg 111→Pro; Lys 114→Trp; and Cys 153→Ser;

(i) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Asp 80→Gly; Ile 89→Asn; Ile 98→Val; Cys 101→Ser; Leu 105→Cys; His 106→Ala; Lys 108→Tyr; Arg 111→Pro; Lys 114→Trp; and Cys 153→Ser;

(j) Ile 10→Phe; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 73→Ala; Ile 89→Asn; Val 93→Glu; Cys 101→Ser; Leu 105→Cys; His 106→Ala; Lys 108→Tyr; Arg 111→Pro; Lys 114→Trp; and Cys 153→Ser;

(k) Ala 5→Thr; Glu 8→Gln; Arg 26→Ser; Glu 27→Asp; Phe 28→Cys; Pro 29→Phe: Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 69→Gly; Val 85→Ala; Cys 101→Ser; Leu 105→Cys; His 106→Ala; Lys 108→Tyr; Arg 111→Pro; Lys 114→Trp; Cys 153→Ser; and Ser 154→Ala;

(l) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Cys 101→Ser; Leu 105→Cys; His 106→Ala; Lys 108→Tyr, Arg 111→Pro; Lys 114→Trp; and Cys 153→Ser;

(m) Ser; 14→Pro; Asp 25→Ser; Arg 26→Asp; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; Lys 108→Thr; Val 110→Gly; Gly 112→Met; Lys 114→Ala; and Lys 121→Thr;

(n) Ser 14→Pro; Asp 25→Ser; Arg 26→Glu; Phe 28→Asp; Met 31→Leu; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Gln; Lys 108→Thr; Val 110→Gly; Gly 112→Met; Lys 114→Ala; and Lys 121→Thr;

(o) Ser 14→Pro; Asp 25→Ser; Arg 26→Glu; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Glu; Lys 108→Thr; Val 110→Gly; Gly 112→Val; Lys 114→Ala; and Lys 121→Thr;

(p) Ser 14→Pro; Asp 25→Ser; Arg 26→Asp; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Gln; Lys 108→Thr; Val 110→Gly; Gly 112→Leu; Lys 114→Ala; and Lys 121→Thr;

(q) Ser 14→Pro; Asp 25→Ser; Arg 26→Ser; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Gln; Lys 108→Thr; Val 110→Gly; Gly 112→Met; Lys 114→Ala; and Lys 121→Thr;

(r) Ser 14→Pro; Asp 25→Ser; Arg 26→Ala; Phe 28→Asp; Asn 32→Thr; Lys 52→Arg; Met 55→Val; Ser 58→Asp; Ala 66→Asn; Ala 79→Glu; His 84→, Tyr; Ala 86→Asp; Cys 101→Phe; Leu 105→Gly; His 106→Lys; Lys 108→Thr; Val 110→Gly; Gly 112→Met; Lys 114→Ala; and Lys 121→Thr;

(s) Ser 14→Pro; Asp 25→Ser; Phe 28→Asp; Asn 32→Thr; Lys 52→Arg; Met 55→Val; Ser 58→Asp; Ala 66→Asn; Ala 79→Glu; Ala 86→Asp; Cys 101→Phe; Leu 105→Gly; His 106→Gln; Lys 108→Thr; Val 110→Asn; Gly 112→Met; Val 113→Ala; Lys 114→Ala; and Lys 121→Thr;

(t) Ser 14→Pro; Asp 25→Ser; Arg 26→Gly; Phe 28→Asp; Met 31→Leu; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Pro; Lys 108→Thr; Val 110→Gly; Gly 112→Met; Lys 114→Ala; and Lys 121→Thr;

(u) Ser 14→Pro; Asp 25→Ser Arg 26→Asp; Phe 28→Asp; Asn 32→Thr; Lys 52 Arg; Met 55→Val; Ser 58→Asp; Ala 66→Asn; Ala 79→Glu; His 84→Leu; Ala 86→Asp; Cys 101→Phe; Leu 105→Gly; His 106→Gln; Lys 108→Thr; Val 110→Gly; Gly 112→Met; Val 113→Leu; Lys 114→Ala; and Lys 121→Thr;

(v) Ser 14→Pro; Asp 25→Ser; Arg 26→Gly; Phe 28→Asp; Asn 32→Met; Lys 52→Arg; Met 55→Val; Ser 58→Asp; Ala 66→Asn; Ala 79→Glu; Ala 86→Asp; Cys 101→Phe; Leu 105→Gly; His 106→Gln; Lys 108→Thr; Val 110→Gly; Gly 112→Met; Lys 114→Ala; and Lys 121→Thr; or (w) Arg 26→Ser, Glu 27→Asp; Phe 28→Cys; Pro 29 Phe; Glu 30→Trp; Met 31→Ile; Asn 32→Asp; Leu 33→Asp; Glu 34→Val; Leu 56→Asp; Ser 58→Phe; Arg 60→Phe; Glu 63→Asp; Lys 65→Glu; Cys 101→Ser; Leu 105→Cys; His 106→Ala; Lys 108→Tyr; Arg 111→Pro; Lys 114→Trp; and Gln 149→Leu.

In some additional embodiments, the LAG-3 binding hTlc muteins include one of the following sets of amino acid mutations in comparison with the linear polypeptide sequence of mature hTlc (SEQ ID NO: 1):

(a) Ala 5→Thr; Glu 8→Gln; Lys 65→Glu; Glu 69→Gly; Val 85→Ala; and Ser 154→Ala;
(b) Ala 5→Thr; Gly 46→Asp; Lys 65→Glu; Val 85→Ala; and Ser 150→Gly
(c) Asp 7→Gly; Val 85→Asp; Arg 148→Trp; and Thr 152→Pro;
(d) Ala 5→Thr; Val 53→Ala; Lys 65→Glu; Ala 79→Thr; and Tyr 97→His;
(e) Glu 63→Asp; Val 85→Asp; Arg 90→Ser; His 96→Asn; and Leu 124→Gln;
(f) Thr 16→Met; Leu 44→His; Lys 65→Glu; and Ile 89→Ser;
(g) Glu 63→Asp; Lys 65→Glu; and Gln 149→Leu;
(h) Lys 65→Glu and Lys 70 Arg;
(i) Ala 5→Thr; Lys 65→Glu; Asp 80→Gly; Ile 89→Asn; and Ile 98→Val
(j) Ile 10→Phe; Lys 65→Glu; Glu 73→Ala; Ile 89→Asn; and Val 93→Glu;
(k) Arg 26→Asp; Asn 32→Thr; His 84→Tyr; Val 110→Gly; and Gly 112→Met;
(l) Arg 26→Glu; Met 31→Leu; Asn 32→Thr; His 84→Tyr; His 106→Gln; Val 110→Gly; and Gly 112→Met;
(m) Arg 26→Glu; Asn 32→Thr; His 84→Tyr; His 106→Glu; and Gly 112→Val;
(n) Arg 26→Asp; Asn 32→Thr; His 84→Tyr; His 106→Gln; Val 110→Gly; and Gly 112→Leu;
(o) Arg 26→Ser; Asn 32→Thr; His 84→Tyr; His 106→Gln; Val 110→Gly; and Gly 112→Met;
(p) Arg 26→Ala; Asn 32→Thr; His 84→Tyr; His 106→Lys; Val 110→Gly; and Gly 112→Met;
(q) Asn 32→Thr; His 106→Gln; Val 110→Asn; Gly 112→Met; and Val 113→Ala;
(r) Arg 26→Gly; Met 31→Leu; Asn 32→Thr; His 84→Tyr; His 106→Pro; Val 110→Gly; and Gly 112→Met; or
(s) Arg 26→Asp; Asn 32→Thr; His 84→Leu; His 106→Gln; Val 110→Gly; Gly 112→Met; and Val 113→Leu.

In some additional embodiments the LAG-3 binding hTlc mutein includes the following amino acid mutation in comparison with the linear polypeptide sequence of the hTlc (SEQ ID NO: 1): Insertion of Pro between positions 156 and 157.

In the residual region, i.e., the region differing from sequence positions 5, 7-8, 10, 14, 16, 25-34, 44, 46, 52-53, 55-56, 58, 60-61, 63, 65-66, 69-70, 73, 79-80, 84-86, 89-90, 93, 96-98, 101, 105-106, 108, 110-114, 121, 124, 148-150, 152-154, and 157, a hTlc mutein of the disclosure may include the wild-type (natural) amino acid sequence of mature hTlc (SEQ ID NO: 1) outside the mutated amino acid sequence positions or mutated amino acid residues at such positions.

Unless otherwise indicated, the position of a residue of a hTlc mutein described herein is numbered in comparison with the linear polypeptide sequence of the hTlc (SEQ ID NO: 1).

In still further embodiments, a hTlc mutein according to the current disclosure has at least 70% sequence identity or at least 70% sequence homology to the sequence of mature hTlc (SEQ ID NO: 1). As an illustrative example, the mutein of the SEQ ID NO: 8 has an amino acid sequence identity or a sequence homology of approximately 81.8% with the amino acid sequence of mature hTlc (SEQ ID NO: 1).

In further particular embodiments, a hTlc mutein of the disclosure comprises an amino acid sequence as set forth in any one of SEQ ID NOs: 7-28, 57-70, and 85-95 or a fragment or variant thereof.

In further particular embodiments, a hTlc mutein of the disclosure has at least 75%, at least 80%, at least 85% or higher, at least 90% or higher, at least 95% or higher, at least 97.5% or higher, at least 98% or higher or at least 99% or higher sequence identity to an amino acid sequence selected from the group consisting of SEQ ID NOs: 8-18, 20-28, 57-70 and 85-95.

The disclosure also includes structural homologues of a hTlc mutein having an amino acid sequence selected from the group consisting of SEQ ID NOs: 7-28, 57-70, and 85-95, which structural homologues have an amino acid sequence homology or sequence identity of more than about 60%, preferably more than 65%, more than 70%, more than 75%, more than 80%, more than 85%, more than 90%, more than 92%, and most preferably more than 95% in relation to said hTlc mutein.

A hTlc mutein according to the present disclosure can be obtained by means of mutagenesis of a naturally occurring form of mature hTlc (SEQ ID NO: 1). In some embodiments of the mutagenesis, a substitution (or replacement) is a conservative substitution. Nevertheless, any substitution—including non-conservative substitution or one or more from the exemplary substitutions below—is envisaged as long as the lipocalin mutein retains its capability to bind to LAG-3, and/or it has a sequence identity to the then substituted sequence in that it is at least 60%, such as at least 65%, at least 70%, at least 75%, at least 80%, at least 85% or higher sequence identity to the amino acid sequence of mature hTlc (SEQ ID NO: 1).

In some particular embodiments, the present disclosure provides a lipocalin mutein that binds human LAG-3 with an affinity measured by a $K_d$ of about 10 nM or lower, 5 nM or lower, 4 nM or lower, 3 nM or lower, 2 nM or lower, 1 nM or lower, 0.5 nM or lower, 0.1 nM or lower or 0.05 nM or lower. In some embodiments, the lipocalin mutein has at least 90% or higher, such as 95% or higher, 97.5% or higher, 98% or higher, or 99% or higher sequence identity to the amino acid sequence of any one of SEQ ID NOs: 7 and 19.

2. Applications of Lipocalin Muteins Specific for LAG-3.

Numerous possible applications for the LAG-3-binding lipocalin muteins of the disclosure exist in medicine.

In one further aspect, the disclosure relates to the use of a LAG-3-binding lipocalin mutein disclosed herein for detecting LAG-3 in a sample as well as a respective method of diagnosis.

The present disclosure also involves the use of one or more LAG-3-binding lipocalin muteins as described for complex formation with LAG-3.

Therefore, in another aspect of the disclosure, the disclosed lipocalin muteins are used for the detection of LAG-3. Such use may include the steps of contacting one or more said muteins, under suitable conditions, with a sample suspected of containing LAG-3, thereby allowing the formation of a complex between the muteins and LAG-3, and detecting the complex by a suitable signal. The detectable signal can be caused by a label, as explained above, or by a change of physical properties due to the binding, i.e., the complex formation, itself. One example is surface plasmon resonance, the value of which is changed during binding of binding partners from which one is immobilized on a surface such as a gold foil.

The LAG-3-binding lipocalin muteins disclosed herein may also be used for the separation of LAG-3. Such use may include the steps of contacting one or more said muteins, under suitable conditions, with a sample supposed to contain LAG-3, thereby allowing the formation of a complex between the muteins and LAG-3 and separating the complex from the sample.

In the use of the disclosed muteins for the detection of LAG-3 as well as the separation of LAG-3, the muteins and/or LAG-3 or a domain or fragment thereof may be immobilized on a suitable solid phase.

In still another aspect, the present disclosure features a diagnostic or analytical kit comprising a LAG-3-binding lipocalin mutein according to the disclosure.

In addition to their use in diagnostics, in yet another aspect, the disclosure contemplates a pharmaceutical composition comprising a mutein of the disclosure and a pharmaceutically acceptable excipient.

Furthermore, the present disclosure provides human lipocalin muteins that bind LAG-3 for use as anti-cancer agents and/or immune modulators. As such the lipocalin muteins of the present disclosure that bind LAG-3 are envisaged to be used in a method of treatment or prevention of human diseases such as cancer, infectious diseases, and autoimmune diseases. Accordingly, also provided are methods of treatment or prevention of human diseases such as cancer, infectious diseases, and autoimmune diseases in a subject in need thereof, comprising administering to said subject a therapeutically effective amount of a lipocalin mutein of the present invention that binds LAG-3.

B. Lipocalin Muteins of the Disclosure

Lipocalins are proteinaceous binding molecules that have naturally evolved to bind ligands. Lipocalins occur in many organisms, including vertebrates, insects, plants and bacteria. The members of the lipocalin protein family (Pervaiz and Brew, FASEB J, 1987) are typically small secreted proteins and have a single polypeptide chain. They are characterized by a range of different molecular-recognition properties: their binding to various, principally hydrophobic, small molecules (such as retinoids, fatty acids, cholesterols, prostaglandins, biliverdins, pheromones, tastants, and odorants), and to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signaling, and the synthesis of prostaglandins. Lipocalins have also been implicated in the regulation of the immune response and the mediation of cell homoeostasis (reviewed, e.g., in Flower et al., Biochim Biophys Acta, 2000, Flower, Biochem J, 1996).

Lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet, closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, formed by four flexible peptide loops. It is the diversity of the loops in the otherwise rigid lipocalin scaffold that gives rise to a variety of different binding modes, each capable of accommodating targets of different size, shape, and chemical character (reviewed, e.g., in Skerra, Biochim Biophys Acta, 2000, Flower et al., Biochim Biophys Acta, 2000, Flower, Biochem J, 1996).

When used herein in the context of the lipocalin muteins of the present disclosure that bind to LAG-3, the term "specific for" includes that the lipocalin mutein is directed against, binds to, or reacts with LAG-3. Thus, being directed to, binding to or reacting with includes that the lipocalin mutein specifically binds to LAG-3. The term "specifically" in this context means that the lipocalin mutein reacts with a LAG-3 protein, as described herein, but essentially not with another protein. The term "another protein" Includes any non-LAG-3 protein, including proteins closely related to or being homologous to LAG-3 against which the lipocalins disclosed herein are directed to. However, LAG-3 proteins, fragments and/or variants from species other than human such as those described in the context of the definition "subject" are not excluded by the term "another protein." The term "does not essentially bind" means that the lipocalin mutein of the present disclosure does not bind another protein, i.e., shows a cross-reactivity of less than 30%, preferably 20%, more preferably 10%, particularly preferably less than 9, 8, 7, 6 or 5%. Whether the lipocalin specifically reacts as defined herein above can easily be tested, inter alia, by comparing the reaction of a lipocalin mutein of the present disclosure with LAG-3 and the reaction of said lipocalin with (an)other protein(s). "Specific binding" can also be determined, for example, in accordance with Western blot, ELISA, RIA, ECL, IRMA, FACS, IHC, and peptide scans.

The amino acid sequence of a lipocalin mutein according to the disclosure has a high sequence identity to the reference lipocalin, for example hTlc, as compared to such mutein's sequence identity with another lipocalin. In this general context, the amino acid sequence of a lipocalin mutein of the combination according to the disclosure is at least substantially similar to the amino acid sequence of the corresponding wild-type or reference lipocalin. A respective sequence of a lipocalin mutein of the combination according to the disclosure, being substantially similar to the sequences of the corresponding reference lipocalin, has at least 65%, at least 70%, at least 75%, at least 80%, at least 82%, at least 85%, at least 87%, at least 90% Identity, including at least 95% identity to the sequence of the corresponding lipocalin. In this regard, a lipocalin mutein of the disclosure of course may contain, in comparison substitutions as described herein which renders the lipocalin mutein capable of binding to LAG-3. Typically, a mutein of a lipocalin includes one or more mutations—relative to the sequence of the reference lipocalin—of amino acids in the four loops at the open end of the ligand binding site of lipocalins (cf. above). As explained above, these regions are essential in determining the binding specificity of a lipocalin mutein for a desired target.

A mutein of the present disclosure may also contain mutations in regions outside of the four flexible peptide loops that form the target binding site of the lipocalin. For example, a mutein of the present invention may contain one or more mutations in one or more of the three peptide loops (designated BC, DE, and FG) connecting the β-strands at the closed end of the lipocalin. As an illustrative example, a mutein derived from a polypeptide of tear lipocalin or a homologue thereof, may have 1, 2, 3, 4 or more mutated amino acid residues at any sequence position in the N-terminal region and/or in the three peptide loops BC, DE, and FG arranged at the end of the β-barrel structure that is located opposite to the natural lipocalin binding pocket. As a further illustrative example, a mutein derived from a polypeptide of tear lipocalin or a homologue thereof, may have no mutated amino acid residues in peptide loop DE arranged at the end of the β-barrel structure, compared to wild-type sequence of tear lipocalin.

A lipocalin mutein according to the disclosure includes one or more, such as 2, 3, 4, 5, 6, 7, 8, 9, 10, 11, 12, 13, 14, 15, 16, 17, 18, 19, or even 20 substitutions in comparison to the corresponding native lipocalin, provided that such a lipocalin mutein should be capable of binding to LAG-3. For example, a lipocalin mutein can have a substitution at a position corresponding to a distinct position (i.e., at a corresponding position) of the wild-type lipocalin having the wild-type sequence of, for example, hTlc. In some embodiments, a lipocalin mutein of the combination according to the disclosure includes at least two amino acid substitutions, including 2, 3, 4, 5, or even more, amino acid substitutions of a native amino acid by an arginine residue. Accordingly, the nucleic acid of a "reference protein" scaffold as described herein is subject to mutagenesis with the aim of generating a lipocalin mutein which is capable of binding to LAG-3.

Also, a lipocalin mutein of the present disclosure can comprise a heterologous amino acid sequence, such as a Strep-tag II sequence, at its N- or C-Terminus, preferably C-terminus, such as in SEQ ID NO: 53 and SEQ ID NO: 54, without affecting the biological activity (binding to its target, e.g. LAG-3) of the lipocalin mutein.

Likewise, a lipocalin mutein of the present disclosure may lack 1, 2, 3, 4, or more amino acids at its N-terminal end and/or 1, 2, or more amino acids at its C-terminal end, in comparison to the respective wild-type tear lipocalin; for example, SEQ ID NOs: 7-28, 57-70, and 85-95.

In some embodiments, a substitution (or replacement) is a conservative substitution. Nevertheless, any substitution—including non-conservative substitution or one or more of the exemplary substitutions listed below—is envisaged as long as the lipocalin mutein retains its capability to bind to LAG-3, and/or it has an identity to the then substituted sequence in that it is at least 60%, such as at least 65%, at least 70%, at least 75%, at least 80%, at least 85% or higher identical to the "reference sequence".

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; lie→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:
a. Alanine (Ala), Glycine (Gly):
b. Aspartic acid (Asp), Glutamic acid (Glu);
c. Asparagine (Asn), Glutamine (Gin);
d. Arginine (Arg), Lysine (Lys);
e. Isoleucine (Ile), Leucine (Leu). Methionine (Met), Valine (Val);
f. Phenylalanine (Phe), Tyrosine (Tyr), Tryptophan (Trp);
g. Serine (Ser), Threonine (Thr); and
h. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gin→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of the lipocalin are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: aspartic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of the respective lipocalin also may be substituted, generally with serine, to improve the oxidative stability of the molecule and prevent aberrant crosslinking. Conversely, cysteine bond(s) may be added to the lipocalin to improve its stability.

Any mutation, including an insertion as discussed above, can be accomplished very easily on the nucleic acid, e.g., DNA level using established standard methods. Illustrative examples of alterations of the amino acid sequence are insertions or deletions as well as amino acid substitutions. Such substitutions may be conservative, i.e., an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein.

Modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target such as LAG-3. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence positions to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective lipocalin mutein. Exemplary possibilities of such a mutation to introduce a cysteine residue into the amino acid sequence of a hTlc mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95, and/or 131 may be used to PEGylate or HESylate the mutein, for example, in order to increase the serum half-life of a respective hTlc mutein.

In some embodiments, if one of the above moieties is conjugated to a lipocalin mutein of the disclosure, conjugation to an amino acid side chain can be advantageous. Suitable amino acid side chains may occur naturally in the amino acid sequence of a human lipocalin or may be introduced by mutagenesis. In case a suitable binding site is introduced via mutagenesis, one possibility is the replacement of an amino acid at the appropriate position by a cysteine residue. For example, such mutation includes at least one of Thr 40→Cys, Glu 73→Cys, Arg 90→Cys, Asp 95→Cys or Glu 131→Cys substitution in the wild-type sequence of human tear lipocalin. The newly created cysteine residue at any of these positions can then be utilized to conjugate the mutein to moiety prolonging the serum half-life of the mutein, such as PEG or an activated derivative thereof.

In another embodiment, in order to provide suitable amino acid side chains for conjugating one of the above compounds to a lipocalin mutein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

For several applications of the muteins disclosed herein it may be advantageous to use them in the form of fusion proteins. In some embodiments, a lipocalin mutein of the disclosure is fused at its N-terminus or its C-terminus to a protein, a protein domain or a peptide, for instance, a signal sequence and/or an affinity tag.

Affinity tags such as the Strep-tag or Strep-tag II (Schmidt et al., J Mol Biol, 1996), the c-myc-tag, the FLAG-tag, the His-tag or the HA-tag or proteins such as glutathione-S-transferase, which allow easy detection and/or purification of recombinant proteins, are further examples of suitable fusion partners. Finally, proteins with chromogenic or fluorescent properties such as the green fluorescent protein (GFP) or the yellow fluorescent protein (YFP) are suitable fusion partners for lipocalin muteins of the disclosure as well.

In general, it is possible to label the lipocalin muteins of the disclosure with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of x-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the lipocalin muteins of the disclosure. The lipocalin muteins of the disclosure may also be conjugated with any suitable therapeutically active agent, e.g., for the targeted delivery of such agents to a given cell, tissue or organ, or for the selective targeting of cells (e.g., tumor cells) without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a lipocalin mutein of the disclosure may in some embodiments be conjugated to a moiety that extends the serum half-life of the mutein (in this regard see also International Patent Publication No. WO 2006/056464, where such conjugation strategies are described with reference to muteins of human neutrophil gelatinase-associated lipocalin (hNGAL) with binding affinity for CTLA-4). The moiety that extends the serum half-life may be a polyalkylene glycol molecule, hydroxyethyl starch, fatty acid molecules, such as palmitic acid (Vajo and Duckworth, Pharmacol Rev, 2000), an Fc part of an immunoglobulin, a $C_H3$ domain of an immunoglobulin, a $C_H4$ domain of an immunoglobulin, an albumin binding peptide, or an albumin binding protein, transferrin to name only a few. The albumin binding protein may be a bacterial albumin binding protein, an antibody, an antibody fragment including domain antibodies (e.g., U.S. Pat. No. 6,696,245), or a lipocalin mutein with binding activity for albumin. Accordingly, suitable conjugation partners for extending the half-life of a lipocalin mutein of the disclosure include an albumin binding protein, for example, a bacterial albumin binding domain, such as the one of streptococcal protein G (Konig and Skerra, J Immunol Methods, 1998). Other examples of albumin binding peptides that can be used as conjugation partner are, for instance, those having a Cys-$Xaa_1$-$Xaa_2$-$Xaa_3$-$Xaa_4$-Cys consensus sequence, wherein $Xaa_1$, is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in U.S. Patent Publication No. 20030069395 or Dennis et al. (J Biol Chem, 2002).

In other embodiments, albumin itself (Osborn et al., J Pharmacol Exp Ther, 2002), or a biologically active fragment of albumin can be used as conjugation partner of a lipocalin mutein of the disclosure. The term "albumin" includes all mammal albumins such as human serum albumin or bovine serum albumin or rat albumin. The albumin or fragment thereof can be recombinantly produced as described in U.S. Pat. No. 5,728,553 or European Patent Publication Nos. EP0330451 and EP0361991. Recombinant human albumin (e.g., Recombumin® from Novozymes Delta Ltd., Nottingham, UK) can be conjugated or fused to a lipocalin mutein of the disclosure in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and MA, USA).

If a transferrin is used as a moiety to extend the serum half-life of the lipocalin muteins of the disclosure, the muteins can be genetically fused to the N- or C-terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution, and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the lipocalin muteins of the disclosure, the SynFusion™ technology, commercially available from Syntonix Pharmaceuticals, Inc. (MA, USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of the lipocalin muteins of the disclosure is to fuse to the N- or C-terminus of a mutein a long, unstructured, flexible glycine-rich sequences (for example poly-glycine with about 20 to 80 consecutive glycine residues). This approach disclosed in International Patent Publication No. WO 2007/038619, for example, has also been term "rPEG" (recombinant PEG).

If PEG is used as conjugation partner, the polyalkylene glycol can be substituted, unsubstituted, linear, or branched. It can also be an activated polyalkylene derivative. Examples of suitable compounds are PEG molecules as described in International Patent Publication No. WO 99/64016, in U.S. Pat. No. 6,177,074, or in U.S. Pat. No. 6,403,564 in relation to interferon, or as described for other proteins such as PEG-modified asparaginase, PEG-adenosine deaminase (PEG-ADA) or PEG-superoxide dismutase (Fuertges and Abuchowski, Journal of Controlled Release, 1990). The molecular weight of such a polymer, such as PEG, may range from about 300 to about 70,000 daltons, including, for example, polyethylene glycol with a molecular weight of about 10,000, of about 20,000, of about 30,000 or of about 40,000 daltons. Moreover, as e.g., described in U.S. Pat. No. 6,500,930 or 6,620,413, carbohydrate oligomers and polymers such as HES can be conjugated to a mutein of the disclosure for the purpose of serum half-life extension.

In addition, a lipocalin mutein disclosed herein may be fused to a moiety may confer new characteristics to the lipocalin muteins of the disclosure such as enzymatic activity or binding affinity for other targets. Examples of suitable fusion partners are alkaline phosphatase, horseradish peroxidase, glutathione S-transferase, the albumin-binding domain of protein G, protein A, antibodies or antibody fragments, oligomerization domains, or toxins.

In particular, it may be possible to fuse a lipocalin mutein disclosed herein with a separate enzyme active site such that both "components" of the resulting fusion protein together act on a given therapeutic target. The binding domain of the lipocalin mutein attaches to the disease-causing target, allowing the enzyme domain to abolish the biological function of the target.

The present disclosure also relates to nucleic acid molecules (DNA and RNA) that include nucleotide sequences encoding the lipocalin muteins of the disclosure. Since the degeneracy of the genetic code permits substitutions of certain codons by other codons specifying the same amino acid, the disclosure is not limited to a specific nucleic acid molecule encoding a lipocalin mutein as described herein but encompasses all nucleic acid molecules that include nucleotide sequences encoding a functional mutein. In this regard, the present disclosure provides nucleotide sequences encoding some lipocalin muteins of the disclosure as shown in SEQ ID NOs: 29-50, 71-84, and 96-106.

In another embodiment of the method according to the disclosure, a nucleic add molecule encoding a hTlc is firstly subjected to mutagenesis at one or more of the amino acid sequence positions 5, 7-8, 10, 14, 16, 25-34, 44, 46, 52-53, 55-56, 58, 60-61, 63, 65-66, 69-70, 73, 79-80, 84-86, 89-90, 93, 96-98, 101, 105-106, 108, 110-114, 121, 124, 148-150, 152-154, and 157 of the linear polypeptide sequence of mature hTlc (SEQ ID NO: 1). Secondly, the nucleic acid molecule encoding a human tear lipocalin is also subjected to mutagenesis at one or more of the amino acid sequence positions 101, 111, 114 and 153 of the linear polypeptide sequence of mature hTlc (SEQ ID NO:1).

The disclosure also includes nucleic acid molecules encoding the lipocalin muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability, formulation stability or ligand binding affinity of the muteins.

A nucleic acid molecule disclosed in this application may be "operably linked" to one or more regulatory sequence(s) to allow expression of this nucleic acid molecule.

A nucleic acid molecule, such as DNA, is referred to as "capable of expressing a nucleic acid molecule" or "able to allow expression of a nucleotide sequence" if it includes sequence elements that contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter, which, in prokaryotes, contains both the promoter per se, i.e., DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5' capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments, a nucleic acid molecule of the disclosure includes a promoter sequence and a transcriptional termination sequence. Suitable prokaryotic promoters are, for example, the tet promoter, the lacUV5 promoter, or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid, or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g., M13K07, VCS-M13 or R408) intact phage particles are produced, thereby enabling physical coupling of the encoded heterologous cDNA to its corresponding polypeptide displayed on the phage surface (Lowman, Annu Rev Biophys Biomol Struct, 1997, Rodi and Makowski, Curr Opin Biotechnol, 1999).

Such cloning vehicles can include, aside from the regulatory sequences described above and a nucleic acid sequence encoding a lipocalin mutein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a lipocalin mutein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g., HeLa cells or CHO cells) or primary mammalian cells.

The disclosure also relates to a method for the production of a lipocalin mutein as described herein, wherein the mutein, a fragment of the mutein or a fusion protein of the mutein and another polypeptide (e.g., another lipocalin mutein or antibody or antibody fragment) is produced starting from the nucleic acid coding for the mutein by means of genetic engineering methods. The method can be carried out in vivo, the lipocalin mutein can for example be produced in a bacterial or eukaryotic host organism and then isolated from this host organism or its culture. It is also possible to produce a protein in vitro, for example by use of an in vitro translation system.

When producing the lipocalin mutein in vivo a nucleic acid encoding such mutein is introduced into a suitable bacterial or eukaryotic host organism by means of recombinant DNA technology (as already outlined above). For this purpose, the host cell is first transformed with a cloning vector that includes a nucleic acid molecule encoding a lipocalin mutein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion protein of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments for hTlc muteins of the disclosure, the naturally occurring disulfide bond between Cys 61 and Cys 153 may be removed. Accordingly, such muteins can be produced in a cell compartment having a reducing redox milieu, for example, in the cytoplasm of Gram-negative bacteria.

In case a lipocalin mutein of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmic reticulum of eukaryotic cells and usually favors the formation of structural disulfide bonds.

It is, however, also possible to produce a mutein of the disclosure in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al., J Mol Biol, 2002).

However, a lipocalin mutein as described herein may not necessarily be generated or produced only by use of genetic engineering. Rather, such a mutein can also be obtained by chemical synthesis such as Merrifield solid phase polypeptide synthesis or by in vitro transcription and translation. It is for example possible that promising mutations are identified using molecular modeling, polypeptides continuing such mutations synthesized in vitro, and investigated for binding activity with respect to LAG-3 and other desirable properties (such as stability). Methods for the solid phase and/or solution phase synthesis of polypeptides/proteins are well known in the art (see e.g., Bruckdorfer et al., Curr Pharm Biotechnol, 2004).

In another embodiment, the lipocalin muteins of the disclosure may be produced by in vitro transcription/translation employing well-established methods known to those skilled in the art.

The skilled worker will appreciate methods useful to prepare lipocalin muteins contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein for its target (e.g., LAG-3). Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

The lipocalin muteins disclosed herein and its derivatives can be used in many fields similar to antibodies or fragments thereof. For example, the lipocalin muteins can be used for labeling with an enzyme, an antibody, a radioactive substance or any other group having biochemical activity or defined binding characteristics. By doing so, their respective targets or conjugates or fusion proteins thereof can be detected or brought in contact with them. In addition, lipocalin muteins of the disclosure can serve to detect chemical structures by means of established analytical methods (e.g., ELISA or Western Blot) or by microscopy or immunosensorics. In this regard, the detection signal can either be generated directly by use of a suitable mutein conjugate or fusion protein or indirectly by immunochemical detection of the bound mutein via an antibody.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

The present invention may further be characterized by the following items:

Item 1. A lipocalin mutein that is capable of binding LAG-3 with an affinity measured by $K_d$ of about 250 nM or lower.

Item 2. The lipocalin mutein of item 1, wherein the mutein is capable of binding LAG-3 with an affinity measured by $K_d$ of about 50 nM or lower.

Item 3. The lipocalin mutein of item 1, wherein the mutein is capable of binding LAG-3 with an affinity measured by $K_d$ of about 3 nM or lower.

Item 4. The lipocalin mutein of item 1, wherein the mutein is capable of binding LAG-3 with an affinity measured by $K_d$ of about 0.1 nM or lower.

Item 5. The lipocalin mutein of item 1, wherein the mutein is capable of binding LAG-3 with an affinity measured by $K_d$ of about 0.05 nM or lower.

Item 6. The lipocalin mutein of any one of items 1-5, wherein the $K_d$ values are determined by surface plasmon resonance analysis as essentially described in Example 4.

Item 7. The lipocalin mutein of any one of items 1-7, wherein the mutein comprises at least two or more mutated amino acid residues at the sequence positions 5, 7-8, 10, 14, 16, 25-34, 44, 46, 52-53, 55-56, 58, 60-61, 63, 65-66, 69-70, 73, 79-80, 84-86, 89-90, 93, 96-98, 101, 105-106, 108, 110-114, 121, 124, 148-150, 152-154, and 156-157 of the linear polypeptide sequence of human tear lipocalin (SEQ ID NO: 1).

Item 8. The lipocalin mutein of any one of items 1-6, wherein the mutein comprises at least one mutated amino acid residues at the sequence positions 14, 25-26, 28, 31-32, 52, 55, 58, 66, 79, 84, 86, 101, 105-106, 108, 110, 112-114, and 121 of the linear polypeptide sequence of human tear lipocalin (SEQ ID NO: 1).

Item 9. The lipocalin mutein of any one of items 1-7, wherein the mutein further comprises at least one or more mutated amino acid residues at the sequence positions 5, 7-8, 10, 16, 26-34, 44, 46, 53, 56, 58, 60-61, 63, 65-66, 69-70, 73, 79-80, 85, 89-90, 93, 96-98, 101, 105-106, 108, 110-111, 114, 121, 124, 148-150, 152-154, and 156-157 of the linear polypeptide sequence of human tear lipocalin (SEQ ID NO: 1).

Item 10. The lipocalin mutein of any one of items 1-9, wherein the mutein comprises at least at least one or more mutated amino acid residues at the sequence positions 5, 7-8, 10, 16, 44, 46, 63, 65, 69-70, 73, 80, 84, 89-90, 93, 96-98, 113, 124, 148-150, 152, 154, and 156-157 of the linear polypeptide sequence of hTlc (SEQ ID NO: 1).

Item 11. The lipocalin mutein of item 7, wherein the amino acid sequence of the mutein comprises two or more of the following mutated amino acid residues in comparison with the linear polypeptide sequence of human tear lipocalin (SEQ ID NO: 1): Ala 5→Thr; Asp 7→Gly; Glu 8→Gln; Ile 10→Phe; Ser 14→Pro; Thr 16→Met; Asp 25→Ser; Arg 26→Ser, Asp, Glu, Ala, or Gly; Glu 27→Asp; Phe 28→Cys or Asp; Pro 29→Phe; Glu 30→Trp; Met 31→Ile or Leu; Asn 32→Asp, Met or Thr; Leu 33→Asp; Glu 34→Val; Leu 44→His; Gly 46→Asp; Lys 52→Arg; Val 53→Ala; Met 55→Val; Leu 56→Asp; Ser 58→Phe or Asp; Arg 60→Phe; Cys 61→Trp; Glu 63→Asp; Lys 65→Glu; Ala 66→Asn; Glu 69 Gly; Lys 70 Arg; Glu 73→Ala; Ala 79→Thr or Glu; Asp 80→Gly; His 84→Tyr or Leu; Val 85→Ala or Asp; Ala 86→Asp; Ile 89→Ser or Asn; Arg 90→Ser; Val 93→Glu; His 96→Asn; Tyr 97→His; Ile 98→Val; Cys 101→Ser or Phe; Leu 105→Cys or Gly; His 106→Ala, Gln, Glu, Lys, or Pro; Lys 108→Tyr or Thr; Val 110→Gly or Asn; Arg 111→Pro; Gly 112→Met, Val, or Leu; Val 113→Ala or Leu; Lys 114→Trp or Ala; Lys 121→Thr; Leu 124→Gln; Arg 148→Trp; Gin 149→Leu; Ser 150→Gly; Thr 152→Pro; Cys 153→Ser; Ser 154→Ala; insertion of Pro between positions 156 and 157.

Item 12. The lipocalin mutein of item 7, wherein the amino acid sequence of the mutein comprises at least one of the following mutated amino acid residues in comparison with the linear polypeptide sequence of human tear lipocalin (SEQ ID NO: 1): Ser 14→Pro; Asp 25→Ser; Arg 26→Ser, Asp, Glu, Ala, or Gly; Phe 28→Asp; Met 31→Leu; Asn 32→Met or Thr; Lys 52→Arg; Met 55→Val; Ser 58→Asp; Ala 66→Asn; Ala 79→Glu; His 84→Tyr or Leu; Ala 86→Asp; Cys 101→Phe; Leu 105→Gly; His 106→Gln, Glu, Lys, or Pro; Lys 108→Thr; Val 110→Gly or Asn; Gly 112→Met, Val, or Leu; Val 113→Ala or Leu; Lys 114→Ala; Lys 121→Thr.

Item 13. The lipocalin mutein of item 7, wherein the amino acid sequence of the mutein comprises at least one of the following mutated amino acid residues in comparison with the linear polypeptide sequence of human tear lipocalin (SEQ ID NO: 1): Ala 5→Thr; Asp 7→Gly; Glu 8→Gln; Ile 10→Phe; Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→, Val; Leu 44→His; Gly 46→Asp; Val 53→Ala; Leu 56→Asp; Ser 58→Phe; Arg 60→Phe; Cys 61→Trp; Glu 63→Asp; Lys 65→Glu; Glu 69→Gly; Lys 70→Arg; Glu 73→Ala; Ala 79→Thr; Asp 80→Gly; Val 85→Ala or Asp; Ile 89→Ser or Asn; Arg 90→Ser; Val 93→Glu; His 96→Asn; Tyr 97→His; Ile 98→Val; Cys 101→Ser; Leu 105→Cys; His 106→Ala; Lys 108→Tyr; Arg 111→Pro; Lys 114→Trp; Leu 124→Gln; Arg 148→Trp; Gin 149→Leu; Ser 150→Gly; Thr 152→Pro; Cys 153→Ser; Ser 154→Ala; insertion of Pro between positions 156 and 157.

Item 14. The lipocalin mutein of any one of items 1-13, wherein the lipocalin mutein binds LAG-3 with an $EC_{50}$ value of about 320 nM or lower.

Item 15. The lipocalin mutein of any one of items 14, wherein the lipocalin mutein binds LAG-3 with an $EC_{50}$ value of about 10 nM or lower.

Item 16. The lipocalin mutein of any one of items 14, wherein the lipocalin mutein binds LAG-3 with an $EC_{50}$ value of about 0.2 nM or lower.

Item 17. The lipocalin mutein of any one of items 14-16, wherein the said $EC_{50}$ values are measured by fluorescence-activated cell sorting as essentially described in Example 5.

Item 18. The lipocalin mutein of any one of items 1-17, wherein the mutein is cross-reactive with both human LAG-3 and cynomolgus LAG-3 (SEQ ID NO: 1).

Item 19. The lipocalin mutein of any one of items 1-18, wherein the mutein is capable of interfering with the binding of human LAG-3 to major histocompatibility complex (MHC) class II.

Item 20. The lipocalin mutein of item 19, wherein the capability of interfering with the binding of human LAG-3 to major histocompatibility complex (MHC) class II is analyzed by fluorescence-activated cell sorting as essentially described in Example 6.

Item 21. The lipocalin mutein of any one of items 1-20, wherein the amino acid sequence of the mutein comprises the following amino acid mutations: Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Cys 101→Ser; Leu 105→Cys; His 106→Ala; Lys 108→Tyr; Arg 111→Pro; Lys 114→Trp; Cys 153→Ser; and one or more of the following amino acid mutations: Ala 5→Thr; Asp 7→Gly; Glu 8→Gln; Ile 10→Phe; Thr 16→Met; Leu 44→His; Gly 46→Asp; Val 53→Ala; Glu 63→Asp; Lys 65→Glu; Glu 69→Gly; Lys 70→Arg; Glu 73→Ala; Ala 79→Thr; Asp 80→Gly; Val 85→Ala or Asp; Ile 89→Ser or Asn; Arg 90→Ser; Val 93→Glu; His 96→Asn; Tyr 97→His; Ile 98→Val; Leu 124→Gln; Arg 148→Trp; Gln 149→Leu; Ser 150→Gly; Thr 152→Pro; Ser 154→Ala; insertion of Pro between positions 156 and 157.

Item 22. The lipocalin mutein of any one of items 1-20, wherein the amino acid sequence of the mutein comprises the following amino acid mutations: Ser 14→Pro; Asp 25→Ser; Phe 28→Asp; Lys 52→Arg; Met 55→Val; Ser 58→Asp; Ala 66→Asn; Ala 79→Glu; Ala 86→Asp; Cys 101→Phe; Leu 105→Gly; Lys 108→Thr; Lys 114→Ala; Lys 121→Thr; and one or more of the following amino acid mutations: Arg 26→Ser, Asp, Glu, or Ala; Met 31→Leu; Asn 32→Thr; Leu 56→Asp; His 84→Tyr or Leu; His 106→Glu, Lys, or Pro; Val 110→Asn; Gly 112→Val or Leu; Val 113→Ala or Leu.

Item 23. The lipocalin mutein of any one of items 1-22, wherein the amino acid sequence of the mutein comprises one of the following sets of amino acid mutations:

(a) Ala 5→Thr; Glu 8→Gln; Arg 26→Ser, Glu 27→Asp; Phe 28→Cys; Pro 29→Phe; Glu 30→Trp: Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 69→Gly; Val 85→Ala; Cys 101→Ser; Leu 105→Cys; His 106→Ala; Lys 108→Tyr; Arg 111→Pro; Lys 114→Trp; Cys 153→Ser; Ser 154 Ala; insertion of Pro between positions 156 and 157;

(b) Ala 5→Thr; Arg 26→Ser Glu 27→Asp; Phe 28→Cys; Pro 29→Phe; Glu 30→Trp; Met 31→Ile; Asn 32→Asp; Leu 33→Asp; Glu 34→Val; Gly 46→Asp; Leu 56→Asp; Ser 58→Phe; Arg 60→Phe; Cys 61→Trp; Lys 65→Glu; Val 85→Ala; Cys 101→Ser; Leu 105→Cys; His 106→Ala; Lys 108→Tyr; Arg 111→Pro; Lys 114→Trp; Ser 150→Gly; Cys 153→Ser; insertion of Pro between positions 156 and 157;

(c) Asp 7→Gly; Arg 26→Ser; Glu 27→Asp; Phe 28→Cys; Pro 29→Phe; Glu 30→Trp; Met 31→Ile; Asn 32→Asp; Leu 33→Asp: Glu 34→Val; Leu 56→Asp; Ser 58→Phe; Arg 60→Phe; Cys 61→Trp; Val 85→Asp; Cys 101→Ser; Leu 105→Cys; His 106→Ala; Lys 108→Tyr; Arg 111→Pro; Lys 114→Trp; Arg 148→Trp; Thr 152→Pro; Cys 153→Ser: insertion of Pro between positions 156 and 157;

(d) Ala 5→Thr; Arg 26→Ser; Glu 27→Asp; Phe 28→Cys; Pro 29→Phe; Glu Trp; Met 31→Ile; Asn 32→Asp; Leu 33→Asp; Glu 34→Val; Val 53→Ala; Leu 56→Asp; Ser 58→Phe; Arg 60→Phe; Cys 61→Trp; Lys 65→Glu; Ala 79→Thr; Tyr 97→His; Cys 101→Ser; Leu 105→Cys; His 106→Ala; Lys 108→Tyr; Arg 111→Pro; Lys 114→Trp; Cys 153→Ser; insertion of Pro between positions 156 and 157;

(e) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Val 85→Asp; Arg 90→Ser; His 96→Asn; Cys 101→Ser; Leu 105→Cys; His 106→Ala; Lys 108→Tyr; Arg 111→Pro: Lys 114→Trp; Leu 124→Gln; Cys 153→Ser;

(f) Thr 16→Met; Arg 26→Ser; Glu 27→Asp; Phe 28→Cys; Pro 29→Phe; Glu 30→Trp; Met 31→Ile; Asn 32→Asp; Leu 33→Asp: Glu 34→Val; Leu 44→His; Leu 56→Asp; Ser 58→Phe; Arg 60→Phe; Cys 61→Trp; Lys 65→Glu; Ile 89→Ser; Cys 101→Ser; Leu 105→Cys; His 106→Ala; Lys 108→Tyr; Arg 111→Pro; Lys 114→Trp; Cys 153→Ser;

(g) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Lys 65→Glu; Cys 101→Ser; Leu 105→Cys; His 106→Ala; Lys 108→Tyr; Arg 111→Pro; Lys 114→Trp; Gln 149→Leu; Cys 153→Ser; Insertion of Pro between positions 156 and 157;

(h) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Lys 70→Arg; Cys 101→Ser; Leu 105→Cys; His 106→Ala; Lys 108→Tyr; Arg 111→Pro; Lys 114→Trp; Cys 153→Ser;

(i) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Asp 80→Gly; Ile 89→Asn; Ile 98→Val; Cys 101→Ser; Leu 105→Cys; His 106→Ala; Lys 108→Tyr; Arg 111→Pro; Lys 114→Trp; Cys 153→Ser; insertion of Pro between positions 156 and 157;

(j) Ile 10→Phe; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 73→Ala; Ile 89→Asn; Val 93→Glu;

Cys 101→Ser Leu 105→Cys; His 106→Ala; Lys 108→Tyr; Arg 111→Pro; Lys 114→Trp; Cys 153→Ser;

(k) Ala 5→Thr; Glu 8→Gln; Arg 26→Ser Glu 27→Asp; Phe 28→Cys; Pro 29→Phe; Glu 30→Trp: Met 31→Ile; Asn 32→Asp; Leu 33→Asp; Glu 34→Val; Leu 56→Asp; Ser 58→Phe; Arg 60→Phe; Cys 61 Trp; Lys 65 Glu; Glu 69→Gly; Val 85→Ala; Cys 101→Ser; Leu 105→Cys; His 106→Ala; Lys 108→Tyr; Arg 111→Pro; Lys 114→Trp; Cys 153→Ser; Ser 154→Ala; insertion of Pro between positions 156 and 157;

(l) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Cys 101→Ser; Leu 105→Cys; His 106→Ala; Lys 108→Tyr, Arg 111→, Pro; Lys 114→Trp; Cys 153→, Ser;

(m) Ser 14→Pro; Asp 25→Ser; Arg 26→Asp; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; Lys 108→Thr; Val 110→Gly; Gly 112→Met; Lys 114→Ala; Lys 121→Thr;

(n) Ser 14→Pro; Asp 25→Ser; Arg 26→Glu; Phe 28→Asp; Met 31→Leu; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Gln; Lys 108→Thr; Val 110→Gly; Gly 112→Met; Lys 114→Ala; Lys 121→Thr;

(o) Ser 14→Pro; Asp 25→Ser; Arg 26→Glu; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Glu: Lys 108→Thr; Val 110→Gly; Gly 112→Val; Lys 114→Ala; Lys 121→Thr;

(p) Ser 14→Pro; Asp 25→Ser; Arg 26→Asp; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106 Gln; Lys 108→Thr; Val 110→Gly; Gly 112→Leu; Lys 114→Ala; Lys 121→Thr;

(q) Ser 14→Pro; Asp 25→Ser; Arg 26→Ser; Phe 28→Asp; Asn 32→Thr; Lys 52→Arg; Met 55→Val; Ser 58→Asp; Ala 66→Asn; Ala 79→Glu; His 84ΔTyr; Ala 86→Asp; Cys 101→Phe; Leu 105→Gly; His 106→Gln; Lys 108→Thr; Val 110→Gly; Gly 112→Met; Lys 114→Ala; Lys 121→Thr;

(r) Ser 14→Pro; Asp 25→Ser; Arg 26→Ala; Phe 28→Asp; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Lys; Lys 108→Thr; Val 110→Gly; Gly 112→Met; Lys 114→Ala; Lys 121→Thr;

(s) Ser 14→Pro; Asp 25→Ser; Phe 28→Asp; Asn 32→Thr; Lys 52→Arg; Met 55→Val; Ser 58→Asp; Ala 66→Asn; Ala 79→Glu; Ala 86→Asp; Cys 101→Phe; Leu 105→Gly; His 106→Gln; Lys 108→Thr; Val 110→Asn; Gly 112→Met; Val 113→Ala; Lys 114→Ala; Lys 121→Thr;

(t) Ser 14→Pro; Asp 25→Ser; Arg 26→Gly; Phe 28→Asp; Met 31→Leu; Asn 32→Thr; Lys 52→Arg; Met 55→Val; Ser 58→Asp; Ala 66→Asn; Ala 79→Glu; His 84→Tyr; Ala 86→Asp; Cys 101→Phe; Leu 105→Gly; His 106→Pro; Lys 108→Thr; Val 110→Gly; Gly 112→Met; Lys 114→Ala; Lys 121→Thr;

(u) Ser 14→Pro; Asp 25→Ser; Arg 26→Asp; Phe 28→Asp; Asn 32→, Thr; Lys 52→Arg; Met 55→Val; Ser 58→Asp; Ala 66→Asn; Ala 79→Glu; His 84→Leu; Ala 86→Asp; Cys 101→Phe; Leu 105→Gly; His 106→Gln; Lys 108→Thr; Val 110→Gly; Gly 112→Met; Val 113→Leu; Lys 114→Ala; Lys 121→Thr; or (v) Ser 14→Pro; Asp 25→Ser; Arg 26→Gly; Phe 28→Asp; Asn 32→Met; Lys 52→Arg; Met 55→Val; Ser 58→Asp; Ala 66→Asn; Ala 79→Glu; Ala 86→Asp; Cys 101→Phe; Leu 105→Gly; His 106→Gln; Lys 108→Thr; Val 110→Gly; Gly 112→Met; Lys 114→Ala; Lys 121→Thr.

Item 24. The lipocalin mutein of any one of items 1-22, wherein the amino acid sequence of the mutein comprises one of the following sets of amino acid mutations:

(a) Ala 5→Thr; Glu 8→Gln; Lys 65→Glu; Glu 69→Gly; Val 85→Ala; Ser 154→Ala; insertion of Pro between positions 156 and 157;

(b) Ala 5→Thr; Gly 46→Asp; Lys 65 Glu; Val 85→Ala; Ser 150→Gly; insertion of Pro between positions 156 and 157;

(c) Asp 7→Gly; Val 85→Asp; Arg 148→Trp; Thr 152→Pro; insertion of Pro between positions 156 and 157;

(d) Ala 5→Thr; Val 53→Ala; Lys 65→Glu; Ala 79→Thr; Tyr 97→His; insertion of Pro between positions 156 and 157;

(e) Glu 63→Asp; Val 85→, Asp; Arg 90→Ser; His 96→, Asn; Leu 124→Gln;

(f) Thr 16→Met; Leu 44→His; Lys 65→Glu; Ile 89→Ser;

(g) Glu 63→Asp; Lys 65→Glu; Gin 149→Leu; insertion of Pro between positions 156 and 157;

(h) Lys 65→Glu; Lys 70→Arg;

(i) Ala 5→Thr; Lys 65→Glu; Asp 80→Gly; Ile 89→Asn; Ile 98→Val; insertion of Pro between positions 156 and 157;

(j) Ile 10→Phe; Lys 65→Glu; Glu 73→Ala; Ile 89→Asn; Val 93→Glu;

(k) Arg 26→Asp; Asn 32→, Thr; His 84→Tyr; Val 110→Gly; Gly 112→Met;

(l) Arg 26→Glu; Met 31→Leu; Asn 32→Thr; His 84→Tyr; His 106→Gln; Val 110→Gly; Gly 112→Met;

(m) Arg 26→Glu; Asn 32→Thr; His 84→Tyr; His 106→Glu; Gly 112→Val;

(n) Arg 26→Asp; Asn 32→Thr; His 84→Tyr; His 106→Gln; Val 110→Gly; Gly 112→Leu;

(o) Arg 26→Ser; Asn 32→Thr; His 84→Tyr; His 106→Gln; Val 110→Gly; Gly 112→Met;

(p) Arg 26→Ala; Asn 32→Thr; His 84→Tyr; His 106→Lys; Val 110→Gly; Gly 112→Met;

(q) Asn 32→Thr; His 106→Gln; Val 110→Asn; Gly 112→Met; Val 113→Ala;

(r) Arg 26→Gly; Met 31→Leu; Asn 32→Thr; His 84→Tyr; His 106→Pro; Val 110→Gly; Gly 112→Met; or (s) Arg 26→Asp; Asn 32→Thr, His 84→Leu; His 106→Gln; Val 110→Gly; Gly 112→Met; Val 113→Leu.

Item 25. The lipocalin mutein of any one of items 1-24, wherein the mutein comprises an amino acid sequence selected from the group consisting of SEQ ID NOs: 8-18 and 20-28 or of a fragment or variant thereof.

Item 26. The lipocalin mutein according to any of items 1-25, wherein the mutein has at least 85%, at least 90%, at least 95%, at least 97.5% or at least 99% sequence identity to an amino acid sequence selected from the group consisting of SEQ ID NOs: SEQ ID NOs: 8-18 and 20-28.

Item 27. The lipocalin mutein of any one of items 1-26, wherein the mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, and colloidal gold.

Item 28. The lipocalin mutein of any one of items 1-27, wherein the mutein is fused at its N-terminus and/or its C-terminus to a fusion partner that is a protein, a protein domain, or a peptide.

Item 29. The lipocalin mutein of any one of items 1-28, wherein the mutein is fused at its N-terminus and/or its C-terminus to a fusion partner that is an antibody or antibody fragment.

Item 30. The lipocalin mutein of any one of items 1-29, wherein the mutein is conjugated to a compound that extends the serum half-life of the mutein.

Item 31. The lipocalin mutein of item 30, wherein the compound that extends the serum half-life is selected from the group consisting of a polyalkylene glycol molecule, hydroethylstarch, a Fc part of an immunoglobulin, a $C_H3$ domain of an immunoglobulin, a $C_H4$ domain of an immunoglobulin, an albumin binding peptide, and an albumin binding protein.

Item 32. The lipocalin mutein of item 31 wherein the polyalkylene glycol molecule is polyethylene (PEG) or an activated derivative thereof.

Item 33. A nucleic acid molecule comprising a nucleotide sequence encoding a lipocalin mutein of any one of items 1-32.

Item 34. An expression vector comprising the nucleic acid molecule of item 33.

Item 35. A host cell containing a nucleic acid molecule of item 34.

Item 36. A method of producing a lipocalin mutein according to any one of items 1-32, wherein the mutein is produced starting from the nucleic acid coding for the mutein or fragment thereof by means of genetic engineering methods.

Item 37. A method of binding LAG-3 in a subject, comprising applying one or more lipocalin muteins according to any one of items 1-32 or one or more compositions comprising such muteins.

Item 38. A method of stimulating immune response in a subject, comprising applying one or more lipocalin muteins according to any one of items 1-32 or one or more compositions comprising such muteins.

Item 39. A method of inducing T lymphocyte proliferation in a subject, comprising applying one or more lipocalin muteins according to any one of items 1-32 or one or more compositions comprising such muteins.

Item 40. A method of interfering with the binding of human LAG-3 to major histocompatibility complex (MHC) class II in a subject, comprising applying one or more lipocalin muteins of any one of items 1-32 or one or more compositions comprising such muteins.

Item 41. The lipocalin mutein of any one of items 1-32 wherein the mutein competes with the binding of human LAG-3 to cells expressing major histocompatibility complex (MHC) class II.

Item 42. The lipocalin mutein of any one of items 1-32 wherein the mutein competes with the binding of human LAG-3 to cells expressing major histocompatibility complex (MHC) class II, when measured in fluorescence-activated cell sorting analysis as essentially described in Example 6.

Item 43. A pharmaceutical composition comprising a the lipocalin mutein of any one of items 1-32 and a pharmaceutically acceptable excipient.

Item 44. An immunoconjugate or fusion protein comprising the lipocalin muteins, or fragment thereof, of any one of items 1-32 linked to a therapeutic agent.

Item 45. The use of a mutein according to any one of items 1-32 for the binding/detection of LAG-3, comprising:
(a) contacting the mutein with a test sample suspected to contain LAG-3, thereby allowing the formation of a complex between the mutein and LAG-3; and
(b) detecting the complex between the mutein and LAG-3 by a suitable signal.

Item 46. A diagnostic or analytical kit comprising a mutein according to any one of items 1-32.

Item 47. A method of detecting the presence of LAG-3 in a biological sample, the method comprising contacting the sample with a mutein of any one of items 1-32 under conditions that allow the formation of a complex of the mutein and LAG-3.

Item 48. The method of item 47, further comprising detecting the complex of the mutein and LAG-3.

Item 49. The method of item 47 or 48, wherein the biological sample is isolated from a human.

Item 50. The method of any one of items 47-49, wherein the sample comprises body fluid.

V. EXAMPLES

Example 1: Generation of Maturation Libraries and Selection of Optimized Muteins Specifically Binding to LAG-3

For optimization of LAG-3-specific muteins, libraries were generated based on mutein SEQ ID NOs: 7 or 19 using either a biased randomization of selected positions or error prone polymerase chain reaction (PCR) based methods. The biased design was made such that for each of the selected positions the amino acid encoded corresponds to the amino acid found in the respective mother clone with a probability of 50-70%, while it can be a different amino acid with a 50-30% probability. With N as the number of targeted positions and B as bias, the most probable number of exchanges per clone is N×(1−B).

The generated lipocalin muteins were cloned with high efficiency into phagemid vector essentially as described (Kim et al., J Am Chem Soc, 2009). Phage display was employed to select for optimized muteins with improved heat stability and binding affinity. The phagemid selection was conducted with increased stringency compared to the initial mutein selections and involved preincubation steps at elevated temperature and limiting target concentration amongst other things.

Example 2: Identification of Muteins Specifically Binding to LAG-3 Using High-Throughput ELISA Screening Individual colonies were used to inoculate 2× Yeast Extract Trypton (2XYT)/Amp medium and grown overnight (14-18 h) to stationary phase. Subsequently, 50 μL 2xYT/

Amp were inoculated from the stationary phase cultures and incubated for 3 h at 37° C. and then shifted to 22° C. until an $OD_{595}$ of 0.6-0.8 was reached. Production of muteins was induced by addition of 10 µL 2xYT/Amp supplemented with 1.2 µg/mL anhydrotetracycline. Cultures were incubated at 22° C. until the next day. After addition of 40 µL of 5% (w/v) BSA in PBS/T and incubation for 1 h at 25° C., cultures were ready for use in screening assays.

Reverse screening formats were applied, where the muteins were captured via the Strep-tag on microtiter plates coated with anti-Strep-Tag antibody and biotinylated LAG-3-Fc was added and detected via Extravidin-horseradish peroxidase (HRP) (Sigma).

To select for muteins with increased affinity and stability the screening was performed with i) reduced antigen concentration, ii) using reverse screening formats where the muteins were captured via the Strep-tag on microtiter plates coated with anti-Strep-Tag antibody and different concentrations of the target was added and detected via either Extravidin-HRP (Sigma) and partially iii) incubation of the screening supernatant at 75° C. before addition to the target plate.

Clones were then sequenced based on the screening results, and muteins were selected for further characterization.

Example 3: Expression of Muteins

Selected muteins with C-terminal sequence SAWSHPQFEK of SA linker and the Strep-tag II peptide (WSHPQFEK) were expressed in E. coli in 2XYT/Amp medium to purify the muteins after expression using Strep-Tactin affinity chromatography and preparative size exclusion chromatography (SEC). After SEC purification, the fractions containing monomeric protein are pooled and analyzed again using analytical SEC. The yield of the lipocalin muteins after Strep-Tactin affinity chromatography and preparative size exclusion chromatography (SEC) Is shown in Table 1 as well as the monomer content of the lipocalin muteins after Strep-Tactin purification:

TABLE 1

| | Expression of muteins | |
|---|---|---|
| SEQ ID NO: | Yield [mg/L] | Monomer content (assessed by analytical SEC) [%] |
| 85 | 4.03 | 100 |
| 86 | 8.33 | 100 |
| 87 | 10.79 | 100 |
| 88 | 10.63 | 94 |
| 89 | 9.56 | 89.6 |
| 90 | 10.40 | 89.9 |
| 91 | 9.96 | 95 |
| 92 | 8.75 | 98.9 |
| 93 | 10.26 | 92.6 |
| 94 | 10.15 | 91.3 |
| 20 | 7.53 | 95 |
| 21 | 8.40 | 96 |
| 22 | 7.86 | 95 |
| 23 | 7.28 | 89 |
| 24 | 7.14 | 92 |
| 25 | 7.38 | 92 |
| 26 | 8.74 | 93 |
| 27 | 8.84 | 97 |
| 28 | 8.04 | 97 |
| 57 | 0.38 | 100 |
| 61 | 0.96 | 100 |
| 63 | 2.26 | 100 |
| 64 | 0.64 | 100 |
| 65 | 5.85 | 100 |

TABLE 1-continued

| | Expression of muteins | |
|---|---|---|
| SEQ ID NO: | Yield [mg/L] | Monomer content (assessed by analytical SEC) [%] |
| 66 | 2.20 | 100 |
| 67 | 0.69 | 100 |
| 68 | 8.29 | 100 |

Example 4: Affinity of Muteins Binding to Human and Cynomolgus LAG-3 Determined by Surface Plasmon Resonance (SPR)

Surface plasmon resonance (SPR) was used to measure binding kinetics and affinity of the representative lipocalin muteins disclosed herein.

The binding of exemplary lipocalin muteins to huLAG-3-Fc (R&D Systems) and cyLAG-3-Fc was determined by Surface Plasmon Resonance (SPR) using a Biacore T200 instrument (GE Healthcare). Recombinant LAG-3 from cynomolgus monkeys (cyLAG-3-Fc) was produced by fusing the extracellular domain of cynomolgus LAG-3 (cyLAG-3) to human IgG1 Fc fragment via a Factor Xa cleavage site and a $(G_4S)_3$ linker.

The anti-human IgG Fc antibody (GE Healthcare) was immobilized on a CM5 sensor chip using standard amine chemistry: the carboxyl groups on the chip were activated using 1-ethyl-3-(3-dimethylaminopropyl)-carbodiimide (EDC) and N-hydroxysuccinimide (NHS). Subsequently, anti-human IgG Fc antibody solution (GE Healthcare) at a concentration of 25 µg/mL in 10 mM sodium acetate (pH) 5 was applied at a flow rate of 5 µL/min until an immobilization level of 9000-14000 resonance units (RU) was achieved. Residual non-reacted NHS-esters were blocked by passing a solution of 1M ethanolamine across the surface. The reference channel was treated in an analogous manner. Subsequently, huLAG-3-Fc at 0.25 µg/mL or cyLAG-3-Fc at 1.5 µg/mL in HBS-EP+ buffer was captured by the anti-human IgG-Fc antibody at the chip surface for 180 s at a flow rate of 10 µL/min.

For affinity determination, dilutions of each mutein were prepared in HBS-EP+ buffer and applied to the prepared chip surface. For SEQ ID NOs: 19-28 concentrations of 100 nM down to 4 nM and in some cases down to 0.8 nM were applied and for SEQ ID NOs: 7 and 85-94 concentrations of 6 nM down to 0.5 nM were applied for affinity measurement to human LAG-3 and 8 nM down to 0.5 nM for affinity measurement to cynomolgus LAG-3. The binding assay was carried out with a contact time of 180 s, a dissociation time of 1500 or 600 s and a flow rate of 30 µl/min. All measurements were performed at 25° C. Regeneration of the chip surface was achieved with injections of 3 M $MgCl_2$ for 60 s and 10 mM glycine-HCl (pH 1.7) for 180 s at a flow rate of 10 µL/min followed by an extra wash with running buffer (HBS-EP+ buffer) and a stabilization period of 120 s. Lipocalin mutein SEQ ID NO: 3 was also tested as a negative control. Prior to the protein measurements, three startup cycles were performed for conditioning purposes. Data were evaluated with Biacore T200 Evaluation software (v2.0). Double referencing was used and the 1:1 binding model was used to fit the raw data.

The values determined for $k_{on}$, $k_{off}$ and the resulting equilibrium dissociation constant ($K_d$) for SEQ ID NOs: 7 and 19, and the optimized lipocalin muteins of SEQ ID NOs: 85-94, 20-28, 57, 61, and 63-68 are summarized in Table 2.

All optimized LAG-3 specific lipocalin muteins bind human as well as cynomolgus LAG-3 with picomolar to low nanomolar affinity and affinities are up to 60-fold improved after optimization.

TABLE 2

Kinetic constants and affinities of LAG-3-specific muteins determined by surface-plasmon-resonance (SPR).

| SEQ ID NO: | human LAG-3 | | | cynomolgus LAG-3 | | |
|---|---|---|---|---|---|---|
| | $k_{on}$ [M$^{-1}$·s$^{-1}$] | $k_{off}$ [s$^{-1}$] | $K_d$ [nM] | $k_{on}$ [M$^{-1}$·s$^{-1}$] | $k_{off}$ [s$^{-1}$] | $K_d$ [nM] |
| 7 | 5.86E+06 | 1.89E−03 | 0.32 | 2.29E+06 | 1.81E−01 | 78.99 |
| 85 | 5.30E+06 | 2.80E−04 | 0.053 | 4.62E+06 | 6.21E−03 | 1.35 |
| 86 | 4.78E+06 | 3.70E−04 | 0.077 | 4.44E+06 | 1.11E−02 | 2.51 |
| 87 | 5.85E+06 | 5.08E−04 | 0.087 | 4.27E+06 | 1.77E−02 | 4.15 |
| 88 | 5.81E+06 | 2.88E−04 | 0.05 | 4.83E+06 | 5.55E−03 | 1.15 |
| 89 | 4.93E+06 | 4.67E−04 | 0.095 | 4.39E+06 | 1.88E−02 | 4.281 |
| 90 | 4.75E+06 | 6.18E−04 | 0.13 | 7.74E+06 | 5.82E−02 | 7.517 |
| 91 | 5.56E+06 | 6.62E−04 | 0.119 | 7.78E+06 | 5.33E−02 | 6.856 |
| 92 | 5.54E+06 | 8.09E−04 | 0.146 | 4.63E+07 | 4.94E−01 | 10.681 |
| 93 | 4.41E+06 | 4.63E−04 | 0.105 | 5.22E+06 | 1.98E−02 | 3.789 |
| 94 | 4.87E+06 | 7.00E−04 | 0.144 | 2.47E+07 | 2.12E−01 | 8.605 |
| 19 | 2.62E+05 | 7.18E−04 | 2.741 | 2.24E+05 | 6.74E−04 | 3.012 |
| 20 | 1.88E+05 | 1.35E−04 | 0.722 | 1.63E+05 | 7.51E−05 | 0.461 |
| 21 | 1.57E+05 | 1.13E−04 | 0.718 | 1.42E+05 | 6.62E−05 | 0.467 |
| 22 | 2.34E+05 | 1.45E−04 | 0.619 | 1.80E+05 | 9.14E−05 | 0.507 |
| 23 | 1.58E+05 | 1.05E−04 | 0.668 | 1.22E+05 | 7.16E−05 | 0.589 |
| 24 | 2.07E+05 | 1.40E−04 | 0.676 | 1.42E+05 | 1.17E−04 | 0.826 |
| 25 | 1.10E+05 | 1.42E−04 | 1.29 | 1.03E+05 | 1.19E−04 | 1.161 |
| 26 | 1.01E+05 | 1.38E−04 | 1.366 | 9.41E+04 | 1.36E−04 | 1.45 |
| 27 | 1.21E+05 | 1.74E−04 | 1.439 | 1.22E+05 | 2.41E−04 | 1.97 |
| 28 | 4.63E+05 | 4.09E−04 | 0.883 | 2.36E+05 | 4.01E−04 | 1.7 |
| 57 | 2.21E+06 | 5.81E−05 | 0.026 | 1.98E+06 | 1.89E−03 | 0.954 |
| 61 | 1.61E+07 | 1.90E−03 | 0.118 | 6.25E+06 | 1.28E−02 | 2.04 |
| 63 | 6.59E+07 | 7.22E−03 | 0.11 | 1.38E+07 | 2.56E−02 | 1.85 |
| 64 | 3.34E+07 | 7.85E−03 | 0.235 | 1.13E+07 | 8.16E−02 | 7.24 |
| 65 | 2.58E+07 | 5.01E−03 | 0.195 | 1.46E+07 | 6.41E−02 | 4.39 |
| 66 | 7.05E+07 | 5.59E−03 | 0.0793 | 2.01E+07 | 2.42E−02 | 1.2 |
| 67 | 2.43E+07 | 5.16E−03 | 0.213 | 1.08E+07 | 5.53E−02 | 5.13 |
| 68 | 3.25E+07 | 5.15E−03 | 0.158 | 2.01E+07 | 4.33E−02 | 2.15 |

Example 5: Fluorescence-Activated Cell Sorting (FACS) Analysis of Lipocalin Muteins Binding to Cells Expressing Human and Cynomolgus LAG-3

We employed fluorescence-activated cell sorting (FACS) studies in order to assess the specific binding of lipocalin muteins SEQ ID NOs: 7, 19-28, and 85-94 to Chinese hamster ovary (CHO) cells stably transfected with huLAG-3 (CHO-huLAG-3) or cyLAG-3 (CHO-cyLAG-3). SEQ ID NO: 3 was tested in parallel as negative control. The cell lines were generated using the Flp-In system (Invitrogen) according to the manufacturer's instructions. Mock-transfected Flp-In CHO cells served as the negative control.

Transfected CHO cells were maintained in Ham's F12 medium (Invitrogen) supplemented with 10% Fetal Calf Serum (FCS, Biochrom) and 500 µg/mL Hygromycin B (Roth). Cells were cultured in cell culture flasks under standard conditions according to manufacturer's instruction (37° C., 5% $CO_2$ atmosphere). In order to dissociate the adherent cells for subculture or FACS experiments, Accutase (PAA) was employed according to the manufacturer's instructions.

To perform the experiment, LAG-3-positive and negative Flp-In CHO cells were incubated with lipocalin muteins, and bound mutein was labeled using fluorescently labeled anti-hTlc antibodies, and then the signal was detected using FACS analysis as described in this example.

$5 \times 10^4$ cells per well were pre-incubated for 1 h in ice-cold PBS containing 5% fetal calf serum (PBS-FCS). Subsequently, a dilution series of lipocalin muteins, the negative control lipocalin mutein (SEQ ID NO: 3), and a benchmark anti-LAG-3 antibody (SEQ ID NOs: 5 and 6) typically ranging from 1 µM to 0.01 nM, was added to the cells, and incubated on ice for 1 h. Cells were washed twice in ice-cold PBS using centrifugation at 500×g and then incubated with a rabbit anti-lipocalin antibody labeled with the fluorescent dye Alexa 488 (Pieris) or a goat anti-human IgG antibody labeled with Alexa 488 (Invitrogen) for 30 min on ice. Cells were subsequently washed and analyzed using a intellicyt IQue Flow cytometer (Intellicyt). Fluorescent data generated by lipocalin mutein binding to LAG-3 expressing cells were analyzed by gating for LAG-3 expressing CHO cells and using Forecyt@ software and resulted geometric fluorescent mean were plotted and fitted using Graphpad software. Data generated for SEQ ID NOs: 7, 19-28, and 85-94 are shown in FIG. 2 and Table 3. All optimized LAG-3 specific muteins (SEQ ID NOs: 85-94 and 20-28) show clear binding to CHO cells expressing either huLAG-3 or cyLAG-3, with $EC_{50}$ comparable to the benchmark antibody. The majority of the optimized muteins exhibits lower ECo values compared to SEQ ID NOs: 7 and 19, indicating improved binding as compared to the parental lipocalin muteins. The differences between binding affinities to human and cynomolgus LAG-3, has been significantly reduced for most of the optimized muteins, representing a preferred feature for potential pharmacokinetic or drug-safety studies. The negative control lipocalin mutein (SEQ ID NO: 3), which do not bind LAG-3, did not show any binding (not shown). No binding of the lipocalin muteins was detected on mock-transfected Flp-In CHO cells (not shown).

TABLE 3

Binding of LAG-3 specific lipocalin muteins and the reference molecule (benchmark anti-LAG-3 antibody, SEQ ID NOs: 5 and 6) to CHO cells transfected with huLAG-3 or cynomolgus LAG.

| SEQ ID NO: | $EC_{50}$ [nm] CHO::human LAG-3 | $EC_{50}$ [nM] CHO::cynomolgus LAG-3 |
|---|---|---|
| 7 | 1.33 | 319.3 |
| 85 | 0.22 | 9.8 |
| 86 | 1.52 | 21.16 |
| 87 | 0.95 | 21.05 |
| 88 | 0.18 | 9.3 |
| 89 | 0.85 | 41.73 |
| 90 | 0.02 | 103.4 |
| 91 | 0.61 | 74.27 |
| 92 | 0.76 | 111.3 |
| 93 | 0.69 | 42.68 |
| 94 | 0.53 | 117.4 |
| 19 | 4.09 | 26.2 |
| 20 | 1.97 | 29.84 |
| 21 | 2.52 | 31.59 |
| 22 | 2.23 | 33.06 |
| 23 | 3.04 | 33.61 |
| 24 | 2.35 | 34.93 |
| 25 | 2.55 | 38.93 |
| 26 | 2.23 | 44.97 |
| 27 | 2.15 | 31.37 |
| 28 | 2.19 | 21.04 |
| 5 and 6 | 0.5 | 46.8 |

Example 6: FACS Analysis of Competitive Binding of Lipocalin Muteins for Human LAG-3 with MHC Class II Expressing Cells To assess whether a given lipocalin mutein interferes with LAG-3 binding to MHC class II on MHC class II-positive cells, a competition FACS experiment was utilized. In this experiment, a constant concentration of human LAG-3-Fc fusion (huLAG-3-Fc, R&D system) and a dilution series of each lipocalin mutein were incubated with the MHC class II positive human cell line A375, and cell-bound huLAG-3-Fc was detected using a fluorescently labelled anti-IgG Fc antibody. In this assay, competitive lipocalin muteins interfering with the binding of huLAG-3 with its ligand MHC class II lead to a reduction of huLAG-3-Fc binding to the MHC class II positive cell line A375.

The melanoma cell line A375 was maintained in DMEM medium (Invitrogen) supplemented with 10% Fetal Calf Serum (FCS, Biochrom). Cells were cultured in cell culture flasks under standard conditions according to manufacturer's instruction (37° C., 5% $CO_2$ atmosphere). In order to dissociate the adherent cells for subculture or FACS experiments, Accutase (PAA Laboratories GmbH) was employed according to the manufacturer's instructions.

For FACS assay, $5 \times 10^4$ A375 cells per well were incubated for 1 h in PBS-FCS, followed by addition of 3 nM huLAG-3-Fc and varying concentrations of the LAG-3-specific lipocalin muteins, ranging from 1 µM to 0.01 nM. Cells were washed twice in ice-cold PBS, re-suspended in PBS-FCS and incubated 30 min on ice with phycoerythrin labelled anti-human IgG Fc antibody (Jackson ImmunoResearch). Cells were subsequently washed and analyzed using an Intellicyt IQue Flow cytometer (Intellicyt). Fluorescent data generated by huLAG-3-Fc binding to A375 cells were analyzed using Forecyt software, and resulted geometric fluorescent mean were normalized to huLAG-3-Fc maximal binding. Percent of huLAG-3-Fc binding were plotted and fitted using Graphpad software. $IC_5$ values of SEQ ID NOs: 7, 19-28, and 85-94 are summarized in Table 4 and selected competition binding curves are provided in FIG. 3. The data show that all optimized lipocalin muteins compete with binding of huLAG-3 to its ligand MHC class II on human MHC class II expressing cells. The detection limit for such experiment was reached, thus improvement in $IC_{50}$ of optimized lipocalin muteins compared to parental muteins, if any, were not observed. The negative control lipocalin mutein (SEQ ID NO: 3), which does not bind to LAG-3, did not show any competition.

TABLE 4

Lipocalin muteins compete with binding of huLAG-3 to its ligand MHC class II on MHC class II expressing cells.

| SEQ ID NO: | $IC_{50}$ [nM] |
|---|---|
| 7 | 0.22 |
| 85 | 0.38 |
| 86 | 0.78 |
| 87 | 0.32 |
| 88 | 1.4 |
| 89 | 0.58 |
| 90 | 0.25 |
| 91 | 0.39 |
| 92 | 0.23 |
| 93 | 0.29 |
| 94 | 0.41 |
| 19 | 1.2 |
| 20 | 1.7 |
| 21 | 0.68 |
| 22 | 1.11 |
| 23 | 0.63 |
| 24 | 1.01 |
| 25 | 0.3 |

TABLE 4-continued

Lipocalin muteins compete with binding of huLAG-3 to its ligand MHC class II on MHC class II expressing cells.

| SEQ ID NO: | $IC_{50}$ [nM] |
|---|---|
| 26 | 0.54 |
| 27 | 0.39 |
| 28 | 0.55 |
| 5 and 6 | 0.28 |

Example 7: Thermal Stability Assessment of Lipocalin Muteins

To determine the melting temperatures ($T_m$s) of the lipocalin muteins, which is a general indicator for overall stability, the LAG-3 specific muteins, at a protein concentration of 1 mg/mL in PBS (Gibco), were scanned (25-100'C) at 1° C./min using a capillary nanoDSC instrument (CSC 6300, TA Instruments). The $T_m$s were calculated from the displayed thermogram using the integrated Nano Analyze software.

The resulting maximum melting temperatures as well as the onset of melting for exemplary lipocalin muteins (SEQ ID NOs: 7, 19-28, 85-94, and 67) are listed in Table 5 below. Almost all lipocalin muteins have $T_m$s in the range of 60 to 80° C., indicating good overall stability with respect to each of these muteins.

TABLE 5

$T_m$ and onset melting temperature as determined by nanoDSC of LAG-3-specific lipocalin muteins

| SEQ ID NO: | $T_m$ [° C.] | Onset melting [° C.] |
|---|---|---|
| 7 | 73 and 81 | 58 |
| 85 | 72 | 60 |
| 86 | 74 | 60 |
| 87 | 72 | 61 |
| 88 | 68 | 55 |
| 89 | 65 | 54 |
| 90 | 66 and 72 | 59 |
| 91 | 80 | 66 |
| 92 | 80 | 69 |
| 93 | 69 and 73 | 58 |
| 94 | 67 | 55 |
| 19 | 58 and 67 | 42 |
| 20 | 64 and 69 | 49 |
| 21 | 58 and 69 | 50 |
| 22 | 64 | 56 |
| 23 | 55 and 67 | 47 |
| 24 | 59 and 68 | 51 |
| 25 | 60 and 68 | 50 |
| 26 | 59 and 70 | 50 |
| 27 | 60 and 70 | 49 |
| 28 | 63 and 70 | 51 |
| 67 | 88 | 74 |

Embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks, and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

Equivalents: Those skilled in the art will recognize, or be able to ascertain using no more than routine experimentation, many equivalents to the specific embodiments of the invention described herein. Such equivalents are intended to be encompassed by the following claims. All publications, patents, and patent applications mentioned in this specification are herein incorporated by reference into the specification to the same extent as if each individual publication, patent or patent application was specifically and individually indicated to be incorporated herein by reference.

NON-PATENT REFERENCES

1. TRIEBEL, F., JITSUKAWA, S., BAIXERAS, E., ROMAN-ROMAN, S., GENEVEE, C., VIEGAS-PEQUIGNOT, E. & HERCEND, T. 1990. LAG-3, a novel lymphocyte activation gene closely related to CD4. *J Exp Med,* 171, 1393-405.
2. KISIELOW, M., KISIELOW, J., CAPOFERRI-SOLLAMI, G. & KARJALAINEN, K. 2005. Expression of lymphocyte activation gene 3 (LAG-3) on B cells is induced by T cells. *Eur J Immunol,* 35, 2081-8.
3. WORKMAN, C. J., WANG, Y., EL KASMI, K. C., PARDOLL, D. M., MURRAY, P. J., DRAKE, C. G. & VIGNALI, D. A. 2009. LAG-3 regulates plasmacytoid dendritic cell homeostasis. *J Immunol,* 182, 1885-91.
4. HUARD, B., MASTRANGELI, R., PRIGENT, P., BRUNIQUEL, D., DONINI, S., EL-TAYAR, N., MAIGRET, B., DREANO, M. & TRIEBEL, F. 1997. Characterization of the major histocompatibility complex class II binding site on LAG-3 protein. *Proc Natl Acad Sci USA,* 94, 5744-9.
5. BUISSON, S. & TRIEBEL, F. 2003. MHC class II engagement by its ligand LAG-3 (CD223) leads to a distinct pattern of chemokine and chemokine receptor expression by human dendritic cells. *Vaccine,* 21, 862-8.
6. ANDREAE, S., PIRAS, F., BURDIN, N. & TRIEBEL, F. 2002. Maturation and activation of dendritic cells induced by lymphocyte activation gene-3 (CD223). *J Immunol,* 168, 3874-80.
7. MACON-LEMAITRE, L. & TRIEBEL, F. 2005. The negative regulatory function of the lymphocyte-activation gene-3 co-receptor (CD223) on human T cells. *Immunology,* 115, 170-8.
8. WOO, S. R., TURNIS, M. E., GOLDBERG, M. V., BANKOTI, J., SELBY, M., NIRSCHL, C. J., BETTINI, M. L., GRAVANO, D. M., VOGEL, P., LIU, C. L., TANGSOMBATVISIT, S., GROSSO, J. F., NETTO, G., SMELTZER, M. P., CHAUX, A., UTZ, P. J., WORKMAN, C. J., PARDOLL, D. M., KORMAN, A. J., DRAKE, C. G. & VIGNALI, D. A. 2012. Immune inhibitory molecules LAG-3 and PD-1 synergistically regulate T-cell function to promote tumoral immune escape. *Cancer Res,* 72, 917-27.
9. ALTSCHUL, S. F., MADDEN, T. L., SCHAFFER, A. A. ZHANG, J., ZHANG, Z., MILLER, W. & LIPMAN, D. J. 1997. Gapped BLAST and PSI-BLAST: a new generation of protein database search programs. *Nucleic Acids Res,* 25, 3389-402.
10. SKERRA, A. 2000. Lipocalins as a scaffold. *Biochim Biophys Acta,* 1482, 337-50.
11. FLOWER, D. R., NORTH, A. C. & SANSOM, C. E. 2000. The lipocalin protein family: structural and sequence overview. *Biochim Biophys Acta,* 1482, 9-24.
12. FLOWER, D. R. 1996. The lipocalin protein family: structure and function. *Biochem J,* 318 (Pt 1), 1-14.
13. FLOWER, D. R. 2000. Beyond the superfamily: the lipocalin receptors. *Biochim Biophys Acta,* 1482, 327-36.
14. BREUSTEDT, D. A., KORNDORFER, I. P., REDL, B. & SKERRA, A. 2005. The 1.8-A crystal structure of human tear lipocalin reveals an extended branched cavity with capacity for multiple ligands. *J Biol Chem,* 280, 484-93.
15. SAMBROOK, J. & RUSSELL, D. W. 2001. *Molecular cloning: a laboratory manual,* Cold Spring Harbor, N.Y., Cold Spring Harbor Laboratory Press.
16. PERVAIZ, S. & BREW, K. 1987. Homology and structure-function correlations between alpha 1-acid glycoprotein and serum retinol-binding protein and its relatives. *FASEB J,* 1, 209-14.
17. SCHMIDT, T. G., KOEPKE, J., FRANK, R. & SKERRA, A. 1996. Molecular Interaction between the Strep-tag affinity peptide and Its cognate target, streptavidin. *J Mol Biol,* 255, 753-66.
18. VAJO, Z. & DUCKWORTH, W. C. 2000. Genetically engineered insulin analogs: diabetes in the new millenium. *Pharmacol Rev,* 52, 1-9.
19. KONIG, T. & SKERRA, A. 1998. Use of an albumin-binding domain for the selective immobilisation of recombinant capture antibody fragments on ELISA plates. *J Immunol Methods,* 218, 73-83.
20. DENNIS, M. S., ZHANG, M., MENG, Y. G., KADKHODAYAN, M., KIRCHHOFER, D., COMBS, D. & DAMICO, L. A. 2002. Albumin binding as a general strategy for improving the pharmacokinetics of proteins. *J Biol Chem,* 277, 35035-43.
21. OSBORN, B. L., OLSEN, H. S., NARDELLI, B., MURRAY, J. H., ZHOU, J. X., GARCIA, A., MOODY, G., ZARITSKAYA, L. S. & SUNG, C. 2002. Pharmacokinetic and pharmacodynamic studies of a human serum albumin-interferon-alpha fusion protein in cynomolgus monkeys. *J Pharmacol Exp Ther,* 303, 540-8.
22. FUERTGES, F. & ABUCHOWSKI, A. 1990. The clinical efficacy of poly(ethylene glycol)-modified proteins. *Journal of Controlled Release,* 11, 139-148.
23. LOWMAN, H. B. 1997. Bacteriophage display and discovery of peptide leads for drug development. *Annu Rev Biophys Biomol Struct.* 26, 401-24.

24. RODI, D. J. & MAKOWSKI, L. 1999. Phage-display technology-finding a needle in a vast molecular haystack. *Curr Opin Biotechnol,* 10, 87-93.

25. VENTURI, M., SEIFERT, C. & HUNTE, C. 2002. High level production of functional antibody Fab fragments in an oxidizing bacterial cytoplasm. *J Mol Biol,* 315, 1-8.

26. BRUCKDORFER, T., MARDER, O. & ALBERICIO, F. 2004. From production of peptides in milligram amounts for research to multi-tons quantities for drugs of the future. *Curr Pharm Biotechnol,* 5, 29-43.

27. KIM, H. J., EICHINGER, A. & SKERRA, A. 2009. High-affinity recognition of lanthanide(III) chelate complexes by a reprogrammed human lipocalin 2. *J Am Chem Soc,* 131, 3565-76.

The invention claimed is:

1. A lipocalin mutein that is capable of binding lymphocyte-activation protein 3 (LAG-3), wherein the mutein has at least 85% sequence identity to an amino acid sequence selected from the group consisting of SEQ ID NOs: 8-18, 57-70, and 85-95,
wherein the amino acid sequence of the mutein comprises the following amino acid mutations in comparison with the linear polypeptide sequence of mature human tear lipocalin (SEQ ID NO: 1): Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 101→Ser; Leu 105→Cys; His 106→Ala; Lys 108→Tyr; Arg 111→Pro; and Lys 114→Trp, and
wherein the amino acid sequence of the mutein further comprises one or more of the following amino acid mutations in comparison with the linear polypeptide sequence of mature human tear lipocalin (SEQ ID NO: 1): Ala 5→Thr; Asp 7→Gly, Asn, Arg, or Lys; Glu 8→Gln; Glu 9→Gln, Arg, or Lys; Ile 10→Phe; Asp 12→Asn or Arg; Thr 16→Met; Leu 44→His; Glu 45→Arg; Gly 46→Asp; Val 53→Ala; Glu 63→Asp; Lys 65→Glu; Glu 69→Gly; Lys 70→Arg; Asp 72→Asn, Arg, or Lys; Glu 73→Ala or Arg; Ala 79→Thr; Asp 80→Gly; Val 85→Ala or Asp; Ile 89→Ser or Asn; Arg 90→Ser; Val 93→Glu; Asp 95→Asn, Arg, or Lys; His 96→Asn; Tyr 97→His; Ile 98→Val; Leu 124→Gln; Arg 148→Trp; Gln 149→Leu; Ser 150→Gly; Thr 152→Pro; and Ser 154→Ala.

2. The lipocalin mutein of claim 1, wherein the mutein is capable of binding LAG-3 with an affinity measured by $K_d$ of about 250 nM or lower, about 50 nM or lower, about 3 nM or lower, about 0.1 nM or lower, or about 0.05 nM or lower.

3. The lipocalin mutein of claim 1, wherein the lipocalin mutein binds LAG-3 with an $EC_{50}$ value of about 320 nM or lower, about 10 nM or lower, or about 0.2 nM or lower.

4. The lipocalin mutein of claim 1, wherein the mutein is cross-reactive with both human LAG-3 and cynomolgus LAG-3.

5. The lipocalin mutein of claim 1, wherein the mutein is capable of interfering with the binding of human LAG-3 to major histocompatibility complex (MHC) class II.

6. The lipocalin mutein of claim 1, wherein the amino acid sequence of the mutein comprises at least 21 of the following mutated amino acid residues in comparison with the linear polypeptide sequence of mature human tear lipocalin (SEQ ID NO: 1): Ala 5→Thr; Asp 7→Gly; Glu 8→Gln; Ile 10→Phe; Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 44→His; Gly 46→Asp; Val 53→Ala; Leu 56→Asp; Ser 58→Phe; Arg 60→Phe; Cys 61→Trp; Glu 63→Asp; Lys 65→Glu; Glu 69→Gly; Lys 70→Arg; Glu 73→Ala; Ala 79→Thr; Asp 80→Gly; Val 85→Ala or Asp; Ile 89→Ser or Asn; Arg 90→Ser; Val 93→Glu; His 96→Asn; Tyr 97→His; Ile 98→Val; Cys 101→Ser; Leu 105→Cys; His 106→Ala; Lys 108→Tyr; Arg 111→Pro; Lys 114→Trp; Leu 124→Gln; Arg 148→Trp; Gln 149→Leu; Ser 150→Gly; Thr 152→Pro; Cys 153→Ser; and Ser 154→Ala.

7. The lipocalin mutein of claim 1, wherein the amino acid sequence of the mutein comprises one of the following sets of amino acid mutations in comparison with the linear polypeptide sequence of mature human tear lipocalin (SEQ ID NO: 1):

(a) Ala 5→Thr; Glu 8→Gln; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 69→Gly; Val 85→Ala; Cys 101→Ser; Leu 105→Cys; His 106→Ala; Lys 108→Tyr; Arg 111→Pro; Lys 114→Trp; Cys 153→Ser; and Ser 154→Ala;

(b) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Gly 46→Asp; Leu 56→Asp; Ser 58→Phe; Arg 60→Phe; Cys 61→Trp; Lys 65→Glu; Val 85→Ala; Cys 101→Ser; Leu 105→Cys; His 106→Ala; Lys 108→Tyr; Arg 111→Pro; Lys 114→Trp; Ser 150→Gly; and Cys 153→Ser;

(c) Asp 7→Gly; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Val 85→Asp; Cys 101→Ser; Leu 105→Cys; His 106→Ala; Lys 108→Tyr; Arg 111→Pro; Lys 114→Trp; Arg 148→Trp; Thr 152→Pro; and Cys 153→Ser;

(d) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Val 53→Ala; Leu 56→Asp; Ser 58→Phe; Arg 60→Phe; Cys 61→Trp; Lys 65→Glu; Ala 79→Thr; Tyr 97→His; Cys 101→Ser; Leu 105→Cys; His 106→Ala; Lys 108→Tyr; Arg 111→Pro; Lys 114→Trp; and Cys 153→Ser;

(e) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Val 85→Asp; Arg 90→Ser; His 96→Asn; Cys 101→Ser; Leu 105→Cys; His 106→Ala; Lys 108→Tyr; Arg 111→Pro; Lys 114→Trp; Leu 124→Gln; and Cys 153→Ser;

(f) Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 44→His; Leu 56→Asp; Ser 58→Phe; Arg 60→Phe; Cys 61→Trp; Lys 65→Glu; Ile 89→Ser; Cys 101→Ser; Leu 105→Cys; His 106→Ala; Lys 108→Tyr; Arg 111→Pro; Lys 114→Trp; and Cys 153→Ser;

(g) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Lys 65→Glu; Cys 101→Ser; Leu 105→Cys; His 106→Ala; Lys 108→Tyr; Arg 111→Pro; Lys 114→Trp; Gln 149→Leu; and Cys 153→Ser;

(h) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Lys 70→Arg; Cys 101→Ser; Leu 105→Cys; His 106→Ala; Lys 108→Tyr; Arg 111→Pro; Lys 114→Trp; and Cys 153→Ser;

(i) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Asp 80→Gly; Ile 89→Asn; Ile 98→Val; Cys 101→Ser; Leu 105→Cys; His 106→Ala; Lys 108→Tyr; Arg 111→Pro; Lys 114→Trp; and Cys 153→Ser;

(j) Ile 10→Phe; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 73→Ala; Ile 89→Asn; Val 93→Glu; Cys 101→Ser; Leu 105→Cys; His 106→Ala; Lys 108→Tyr; Arg 111→Pro; Lys 114→Trp; and Cys 153→Ser;

(k) Ala 5→Thr; Glu 8→Gln; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 69→Gly; Val85→Ala; Cys 101→Ser; Leu 105→Cys; His 106→Ala; Lys 108→Tyr; Arg 111→Pro; Lys 114→Trp; Cys 153→Ser; and Ser 154→Ala;

(l) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Glu 45→Arg; Leu 56→Asp; Ser 58→Phe; Arg 60→Phe; Cys 61→Trp; Glu 63→Asp; Lys 65→Glu; Glu 73→Arg; Asp 80→Gly; Cys 101→Ser; Leu 105→Cys; His 106→Ala; Lys 108→Tyr; Arg 111→Pro; Lys 114→Trp; Gln 149→Leu; and Cys 153→Ser;

(m) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Glu 63→Asp; Lys 65→Glu; Cys 101→Ser; Leu 105→Cys; His 106→Ala; Lys 108→Tyr; Arg 111→Pro; Lys 114→Trp; and Gln 149→Leu;

(n) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Lys 65→Glu; Cys 101→Ser; Leu 105→Cys; His 106→Ala; Lys 108→Tyr; Arg 111→Pro; Lys 114→Trp; Gln 149→Leu; and Cys 153→Ser;

(o) Asp 12→Asn; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Lys 65→Glu; Cys 101→Ser; Leu 105→Cys; His 106→Ala; Lys 108→Tyr; Arg 111→Pro; Lys 114→Trp; Gln 149→Leu; and Cys 153→Ser; or (p) Asp 12→Asn; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Glu 63→Asp; Lys 65→Glu; Cys 101→Ser; Leu 105→Cys; His 106→Ala; Lys 108→Tyr; Arg 111→Pro; Lys 114→Trp; and Gln 149→Leu.

8. The lipocalin mutein of claim 1, wherein the amino acid sequence of the mutein comprises cysteine residues at the sequence positions 61 and 153 of the linear polypeptide sequence of mature human tear lipocalin (SEQ ID NO: 1).

9. The lipocalin mutein of claim 1, wherein the mutein comprises an amino acid sequence selected from the group consisting of SEQ ID NOs: 8-18, 57-70, and 85-95 or a functional fragment thereof.

10. The lipocalin mutein claim 1, wherein the mutein has at least 90%, at least 95%, at least 97.5% or at least 99% sequence identity to an amino acid sequence selected from the group consisting of SEQ ID NOs: 8-18, 57-70, and 85-95.

11. The lipocalin mutein of claim 1, wherein the mutein is conjugated to a compound selected from the group consisting of an organic molecule, an enzyme label, a radioactive label, a colored label, a fluorescent label, a chromogenic label, a luminescent label, a hapten, digoxigenin, biotin, a cytostatic agent, a toxin, a metal complex, a metal, colloidal gold, and a compound that extends the serum half-life of the mutein.

12. The lipocalin mutein of claim 11, wherein the compound that extends the serum half-life is selected from the group consisting of a polyalkylene glycol molecule, a polyethylene (PEG) glycol molecule, hydroxyethyl starch, an Fc part of an immunoglobulin, a $C_H3$ domain of an immunoglobulin, a $C_H4$ domain of an immunoglobulin, an albumin binding peptide, and an albumin binding protein.

13. The lipocalin mutein of claim 1, wherein the mutein is fused at its N-terminus and/or its C-terminus to a fusion partner that is an antibody, an antibody fragment, a protein, a protein domain, or a peptide.

14. The lipocalin mutein of claim 1, wherein the mutein has at least 85% sequence identity to an amino acid sequence selected from the group consisting of SEQ ID NOs: 8-18.

15. The lipocalin mutein of claim 14, wherein the amino acid sequence of the mutein comprises at least 21 of the following mutated amino acid residues in comparison with the linear polypeptide sequence of mature human tear lipocalin (SEQ ID NO: 1): Ala 5→Thr; Asp 7→Gly; Glu 8→Gln; Ile 10→Phe; Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 44→His; Gly 46→Asp; Val 53→Ala; Leu 56→Asp; Ser 58→Phe; Arg 60→Phe; Cys 61→Trp; Glu 63→Asp; Lys 65→Glu; Glu 69→Gly; Lys 70→Arg; Glu 73→Ala; Ala 79→Thr; Asp 80→Gly; Val 85→Ala or Asp; Ile 89→Ser or Asn; Arg 90→Ser; Val 9343 Glu; His 96→Asn; Tyr 97→His; Ile 98→Val; Cys 101→Ser; Leu 105→Cys; His 106→Ala; Lys 108→Tyr; Arg 111→Pro; Lys 114→Trp; Leu 124→Gln; Arg 148→Trp; Gln 149→Leu; Ser 150→Gly; Thr 152→Pro; Cys 153→Ser; and Ser 154→Ala.

16. The lipocalin mutein of claim 1, wherein the amino acid sequence of the mutein comprises one of the following sets of amino acid mutations in comparison with the linear polypeptide sequence of mature human tear lipocalin (SEQ ID NO: 1):

(a) Ala 5→Thr; Glu 8→Gln; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 69→Gly; Val 85→Ala; Cys 101→Ser; Leu 105→Cys; His 106→Ala; Lys 108→Tyr; Arg 111→Pro; Lys 114→Trp; Cys 153→Ser; and Ser 154→Ala;

(b) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Gly 46→Asp; Leu 56→Asp; Ser 58→Phe; Arg 60→Phe; Cys 61→Trp; Lys 65→Glu; Val 85→Ala; Cys 101→Ser; Leu 105→Cys; His 106→Ala; Lys 108→Tyr; Arg 111→Pro; Lys 114→Trp; Ser 150→Gly; and Cys 153→Ser;

(c) Asp 7→Gly; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Val 85→Asp; Cys 101→Ser; Leu 105→Cys; His 106→Ala; Lys 108→Tyr; Arg 111→Pro; Lys 114→Trp; Arg 148→Trp; Thr 152→Pro; and Cys 153→Ser;

(d) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Val 53→Ala; Leu 56→Asp; Ser 58→Phe; Arg 60→Phe; Cys 61→Trp; Lys 65→Glu; Ala 79→Thr; Tyr 97→His; Cys 101→Ser; Leu 105→Cys; His 106→Ala; Lys 108→Tyr; Arg 111→Pro; Lys 114→Trp; and Cys 153→Ser;

(e) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Val 85→Asp; Arg 90→Ser; His 96→Asn; Cys 101→Ser; Leu 105→Cys; His 106→Ala; Lys 108→Tyr; Arg 111→Pro; Lys 114→Trp; Leu 124→Gln; and Cys 153→Ser;

(f) Thr 16→Met; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 44→His; Leu 56→Asp; Ser 58→Phe; Arg 60→Phe; Cys 61→Trp; Lys 65→Glu; Ile 89→Ser; Cys 101→Ser; Leu 105→Cys; His 106→Ala; Lys 108→Tyr; Arg 111→Pro; Lys 114→Trp; and Cys 153→Ser;

(g) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Glu 63→Asp; Lys 65→Glu; Cys 101→Ser; Leu 105→Cys; His 106→Ala; Lys 108→Tyr; Arg 111→Pro; Lys 114→Trp; Gln 149→Leu; and Cys 153→Ser;

(h) Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Lys 70→Arg; Cys 101→Ser; Leu 105→Cys; His 106→Ala; Lys 108→Tyr; Arg 111→Pro; Lys 114→Trp; and Cys 153→Ser;

(i) Ala 5→Thr; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Asp 80→Gly; Ile 89→Asn; Ile 98→Val; Cys 101→Ser; Leu 105→Cys; His 106→Ala; Lys 108→Tyr; Arg 111→Pro; Lys 114→Trp; and Cys 153→Ser;

(j) Ile 10→Phe; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 58→Phe; Arg 60→Phe; Cys 61→Trp; Lys 65→Glu; Glu 73→Ala; Ile 89→Asn; Val 93→Glu; Cys 101→Ser; Leu 105→Cys; His 106→Ala; Lys 108→Tyr; Arg 111→Pro; Lys 114→Trp; and Cys 153→Ser;

(k) Ala 5→Thr; Glu 8→Gln; Arg 26→Ser; Glu 27→Asp; Phe 28→Cys; Pro 29→Phe; Glu 30→Trp; Met 31→Ile; Asn 32→Asp; Leu 33→Asp; Glu 34→Val; Leu 56→Asp; Ser 5→Phe; Arg 60→Phe; Cys 61→Trp; Lys 65→Glu; Glu 69→Gly; Val 85→Ala; Cys 101→Ser; Leu 105→Cys; His 106→Ala; Lys 108→Tyr; Arg 111→Pro; Lys 114→Trp; Cys 153→Ser; and Ser 154→Ala;.

17. The lipocalin mutein of claim 16, wherein the amino acid sequence of the mutein comprises cysteine residues at the sequence positions 61 and 153 of the linear polypeptide sequence of mature human tear lipocalin (SEQ ID NO: 1).

18. The lipocalin mutein of claim 16, wherein the mutein has at least 95% sequence identity to an amino acid sequence selected from the group consisting of SEQ ID NOs: 8-18.

19. A pharmaceutical composition comprising the lipocalin mutein of claim 1 and a pharmaceutically acceptable excipient.

20. An immunoconjugate or fusion protein comprising the lipocalin mutein, or fragment thereof, of claim 1 linked to a therapeutic agent.

21. A diagnostic or analytical kit comprising the mutein of claim 1.

22. A nucleic acid molecule comprising a nucleotide sequence encoding the lipocalin mutein of claim 1.

23. A host cell containing a nucleic acid molecule of claim 22.

24. A method of producing a lipocalin mutein of claim 1, wherein the mutein is produced starting from the nucleic acid coding for the mutein or fragment thereof.

25. A method of binding or detecting LAG-3 in a subject, comprising applying one or more lipocalin muteins of claim 1 or one or more compositions comprising such muteins.

26. A method of stimulating an immune response in a subject, comprising applying one or more lipocalin muteins of claim 1 or one or more compositions comprising such muteins.

27. A method of inducing T lymphocyte proliferation in a subject, comprising applying one or more lipocalin muteins of claim 1 or one or more compositions comprising such muteins.

28. A method of interfering with the binding of human LAG-3 to MHC class II in a subject, comprising applying one or more lipocalin muteins of claim 1 or one or more compositions comprising such muteins.

* * * * *

SEQUENCE LISTING

<160> NUMBER OF SEQ ID NOS: 106

<210> SEQ ID NO 1
<211> LENGTH: 158
<212> TYPE: PRT
<213> ORGANISM: Homo sapiens

<400> SEQUENCE: 1

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 2
<211> LENGTH: 659
<212> TYPE: PRT
<213> ORGANISM: Artificial Sequence
<220> FEATURE:
<223> OTHER INFORMATION: LAG-3 Fc fusion protein

<400> SEQUENCE: 2

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

-continued

```
Arg Gly Arg Gln Arg Gly Asp Phe Ser Leu Trp Leu Arg Pro Ala Arg
                100                 105                 110

Arg Ala Asp Ala Gly Glu Tyr Arg Ala Ala Val His Leu Arg Asp Arg
            115                 120                 125

Ala Leu Ser Cys Arg Leu Arg Leu Arg Leu Gly Gln Ala Ser Met Thr
        130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
370                 375                 380

Gln Leu Tyr Gln Gly Glu Arg Leu Leu Gly Ala Ala Val Tyr Phe Thr
385                 390                 395                 400

Glu Leu Ser Ser Pro Gly Ala Gln Arg Ser Gly Arg Ala Pro Gly Ala
                405                 410                 415

Leu Pro Ala Gly His Leu Ile Glu Gly Arg Met Asp Pro Lys Ser Cys
            420                 425                 430

Asp Lys Thr His Thr Cys Pro Pro Cys Pro Ala Pro Glu Ala Glu Gly
        435                 440                 445

Ala Pro Ser Val Phe Leu Phe Pro Pro Lys Pro Lys Asp Thr Leu Met
450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
```

```
                515                 520                 525
Lys Glu Tyr Lys Cys Lys Val Ser Asn Lys Ala Leu Pro Ala Pro Ile
    530                 535                 540
Glu Lys Thr Ile Ser Lys Ala Lys Gly Gln Pro Arg Glu Pro Gln Val
545                 550                 555                 560
Tyr Thr Leu Pro Pro Ser Arg Asp Glu Leu Thr Lys Asn Gln Val Ser
                565                 570                 575
Leu Thr Cys Leu Val Lys Gly Phe Tyr Pro Ser Asp Ile Ala Val Glu
            580                 585                 590
Trp Glu Ser Asn Gly Gln Pro Glu Asn Asn Tyr Lys Ala Thr Pro Pro
                595                 600                 605
Val Leu Asp Ser Asp Gly Ser Phe Phe Leu Tyr Ser Lys Leu Thr Val
            610                 615                 620
Asp Lys Ser Arg Trp Gln Gln Gly Asn Val Phe Ser Cys Ser Val Met
625                 630                 635                 640
His Glu Ala Leu His Asn His Tyr Thr Gln Lys Ser Leu Ser Leu Ser
                645                 650                 655
Pro Gly Lys

<210> SEQ ID NO 3
<211> LENGTH: 152
<212> TYPE: PRT
<213> ORGANISM: Artificial Sequence
<220> FEATURE:
<223> OTHER INFORMATION: lipocalin mutein

<400> SEQUENCE: 3

Ala Ser Asp Glu Glu Ile Gln Asp Val Ser Gly Thr Trp Tyr Leu Lys
1               5                   10                  15
Ala Met Thr Val Asp Arg Glu Cys Pro Glu Met Asn Leu Glu Ser Val
            20                  25                  30
Thr Pro Met Thr Leu Thr Thr Leu Glu Gly Gly Asn Leu Glu Ala Lys
        35                  40                  45
Val Thr Met Leu Ile Ser Gly Arg Ser Gln Glu Val Lys Ala Val Leu
    50                  55                  60
Glu Lys Thr Asp Glu Pro Gly Lys Tyr Thr Ala Asp Gly Gly Lys His
65                  70                  75                  80
Val Ala Tyr Ile Ile Arg Ser His Val Lys Asp His Tyr Ile Phe Tyr
                85                  90                  95
Ser Glu Gly Glu Cys His Gly Lys Pro Val Pro Gly Val Trp Leu Val
            100                 105                 110
Gly Arg Asp Pro Lys Asn Asn Leu Glu Ala Leu Glu Asp Phe Glu Lys
        115                 120                 125
Ala Ala Gly Ala Arg Gly Leu Ser Thr Glu Ser Ile Leu Ile Pro Arg
    130                 135                 140
Gln Ser Glu Thr Ser Ser Pro Gly
145                 150

<210> SEQ ID NO 4
<211> LENGTH: 152
<212> TYPE: PRT
<213> ORGANISM: Artificial Sequence
<220> FEATURE:
<223> OTHER INFORMATION: lipocalin mutein

<400> SEQUENCE: 4

Ala Ser Asp Glu Glu Ile Gln Asp Val Pro Gly Thr Trp Tyr Leu Lys
```

```
                1               5                      10                      15
            Ala Met Thr Val Asp Arg Glu Phe Pro Glu Met Asn Leu Glu Ser Val
                                20                      25                      30
            Thr Pro Met Thr Leu Thr Thr Leu Glu Gly Gly Asn Leu Glu Ala Lys
                                35                      40                      45
            Val Thr Met Leu Ile Ser Gly Arg Cys Gln Glu Val Lys Ala Val Leu
                                50                      55                      60
            Glu Lys Thr Asp Glu Pro Gly Lys Tyr Thr Ala Asp Gly Lys His
             65                  70                      75                      80
            Val Ala Tyr Ile Ile Arg Ser His Val Lys Asp His Tyr Ile Phe Tyr
                                85                      90                      95
            Ser Glu Gly Glu Leu His Gly Lys Pro Val Arg Gly Val Lys Leu Val
                                100                     105                     110
            Gly Arg Asp Pro Thr Asn Asn Leu Glu Ala Leu Glu Asp Phe Glu Lys
                                115                     120                     125
            Ala Ala Gly Ala Arg Gly Leu Ser Thr Glu Ser Ile Leu Ile Pro Arg
                                130                     135                     140
            Gln Ser Glu Thr Cys Ser Pro Gly
             145                 150
```

<210> SEQ ID NO 5
<211> LENGTH: 447
<212> TYPE: PRT
<213> ORGANISM: Artificial Sequence
<220> FEATURE:
<223> OTHER INFORMATION: Lag-3 antibody heavy chain

<400> SEQUENCE: 5

```
            Gln Val Gln Leu Gln Gln Trp Gly Ala Gly Leu Leu Lys Pro Ser Glu
             1               5                      10                      15
            Thr Leu Ser Leu Thr Cys Ala Val Tyr Gly Gly Ser Phe Ser Asp Tyr
                                20                      25                      30
            Tyr Trp Asn Trp Ile Arg Gln Pro Pro Gly Lys Gly Leu Glu Trp Ile
                                35                      40                      45
            Gly Glu Ile Asn His Arg Gly Ser Thr Asn Ser Asn Pro Ser Leu Lys
                                50                      55                      60
            Ser Arg Val Thr Leu Ser Leu Asp Thr Ser Lys Asn Gln Phe Ser Leu
             65                  70                      75                      80
            Lys Leu Arg Ser Val Thr Ala Ala Asp Thr Ala Val Tyr Tyr Cys Ala
                                85                      90                      95
            Phe Gly Tyr Ser Asp Tyr Glu Tyr Asn Trp Phe Asp Pro Trp Gly Gln
                                100                     105                     110
            Gly Thr Leu Val Thr Val Ser Ser Ala Ser Thr Lys Gly Pro Ser Val
                                115                     120                     125
            Phe Pro Leu Ala Pro Cys Ser Arg Ser Thr Ser Glu Ser Thr Ala Ala
                                130                     135                     140
            Leu Gly Cys Leu Val Lys Asp Tyr Phe Pro Glu Pro Val Thr Val Ser
             145                 150                     155                     160
            Trp Asn Ser Gly Ala Leu Thr Ser Gly Val His Thr Phe Pro Ala Val
                                165                     170                     175
            Leu Gln Ser Ser Gly Leu Tyr Ser Leu Ser Ser Val Val Thr Val Pro
                                180                     185                     190
            Ser Ser Ser Leu Gly Thr Lys Thr Tyr Thr Cys Asn Val Asp His Lys
                                195                     200                     205
            Pro Ser Asn Thr Lys Val Asp Lys Arg Val Glu Ser Lys Tyr Gly Pro
```

```
                210                 215                 220
Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 6
<211> LENGTH: 214
<212> TYPE: PRT
<213> ORGANISM: Artificial Sequence
<220> FEATURE:
<223> OTHER INFORMATION: Lag-3 antibody light chain

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Asn Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                    130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 7
<211> LENGTH: 152
<212> TYPE: PRT
<213> ORGANISM: Artificial Sequence
<220> FEATURE:
<223> OTHER INFORMATION: lipocalin mutein

<400> SEQUENCE: 7

Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 8
<211> LENGTH: 153
<212> TYPE: PRT
<213> ORGANISM: Artificial Sequence
<220> FEATURE:
<223> OTHER INFORMATION: lipocalin mutein

<400> SEQUENCE: 8

Thr Ser Asp Gln Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Glu Val Glu Ala Val Leu
    50                  55                  60
```

```
Gly Lys Thr Asp Glu Pro Gly Lys Tyr Thr Ala Asp Gly Gly Lys His
 65                  70                  75                  80

Ala Ala Tyr Ile Ile Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ala Pro Gly Pro
145                 150
```

<210> SEQ ID NO 9
<211> LENGTH: 153
<212> TYPE: PRT
<213> ORGANISM: Artificial Sequence
<220> FEATURE:
<223> OTHER INFORMATION: lipocalin mutein

<400> SEQUENCE: 9

```
Thr Ser Asp Glu Glu Ile Gln Asp Val Ser Gly Thr Trp Tyr Leu Lys
 1               5                  10                  15

Ala Met Thr Val Asp Ser Asp Cys Phe Trp Ile Asp Asp Val Ser Val
                 20                  25                  30

Thr Pro Met Thr Leu Thr Thr Leu Glu Asp Gly Asn Leu Glu Ala Lys
             35                  40                  45

Val Thr Met Asp Ile Phe Gly Phe Trp Gln Glu Val Glu Ala Val Leu
 50                  55                  60

Glu Lys Thr Asp Glu Pro Gly Lys Tyr Thr Ala Asp Gly Gly Lys His
 65                  70                  75                  80

Ala Ala Tyr Ile Ile Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Gly Glu Thr Ser Ser Pro Gly Pro
145                 150
```

<210> SEQ ID NO 10
<211> LENGTH: 153
<212> TYPE: PRT
<213> ORGANISM: Artificial Sequence
<220> FEATURE:
<223> OTHER INFORMATION: lipocalin mutein

<400> SEQUENCE: 10

```
Ala Ser Gly Glu Glu Ile Gln Asp Val Ser Gly Thr Trp Tyr Leu Lys
 1               5                  10                  15

Ala Met Thr Val Asp Ser Asp Cys Phe Trp Ile Asp Asp Val Ser Val
                 20                  25                  30

Thr Pro Met Thr Leu Thr Thr Leu Glu Gly Gly Asn Leu Glu Ala Lys
             35                  40                  45

Val Thr Met Asp Ile Phe Gly Phe Trp Gln Glu Val Lys Ala Val Leu
 50                  55                  60
```

Glu Lys Thr Asp Glu Pro Gly Lys Tyr Thr Ala Asp Gly Lys His
65                  70                  75                  80

Asp Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Trp
        130                 135                 140

Gln Ser Glu Pro Ser Ser Pro Gly Pro
145                 150

<210> SEQ ID NO 11
<211> LENGTH: 153
<212> TYPE: PRT
<213> ORGANISM: Artificial Sequence
<220> FEATURE:
<223> OTHER INFORMATION: lipocalin mutein

<400> SEQUENCE: 11

Thr Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Ala Thr Met Asp Ile Phe Gly Phe Trp Gln Glu Val Glu Ala Val Leu
        50                  55                  60

Glu Lys Thr Asp Glu Pro Gly Lys Tyr Thr Thr Asp Gly Lys His
65                  70                  75                  80

Val Ala Tyr Ile Ile Arg Ser His Val Lys Asp His His Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Pro
145                 150

<210> SEQ ID NO 12
<211> LENGTH: 153
<212> TYPE: PRT
<213> ORGANISM: Artificial Sequence
<220> FEATURE:
<223> OTHER INFORMATION: lipocalin mutein

<400> SEQUENCE: 12

Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Asp Val Lys Ala Val Leu

```
                    50                  55                  60
Glu Lys Thr Asp Glu Pro Gly Lys Tyr Thr Ala Asp Gly Lys His
 65                  70                  75                  80

Asp Ala Tyr Ile Ile Ser Ser His Val Lys Asp Asn Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Gln Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Pro
145                 150

<210> SEQ ID NO 13
<211> LENGTH: 153
<212> TYPE: PRT
<213> ORGANISM: Artificial Sequence
<220> FEATURE:
<223> OTHER INFORMATION: lipocalin mutein

<400> SEQUENCE: 13

Ala Ser Asp Glu Glu Ile Gln Asp Val Ser Gly Met Trp Tyr Leu Lys
 1               5                  10                  15

Ala Met Thr Val Asp Ser Asp Cys Phe Trp Ile Asp Asp Val Ser Val
                20                  25                  30

Thr Pro Met Thr Leu Thr Thr His Glu Gly Gly Asn Leu Glu Ala Lys
            35                  40                  45

Val Thr Met Asp Ile Phe Gly Phe Trp Gln Glu Val Glu Ala Val Leu
        50                  55                  60

Glu Lys Thr Asp Glu Pro Gly Lys Tyr Thr Ala Asp Gly Lys His
 65                  70                  75                  80

Val Ala Tyr Ile Ser Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Pro
145                 150

<210> SEQ ID NO 14
<211> LENGTH: 153
<212> TYPE: PRT
<213> ORGANISM: Artificial Sequence
<220> FEATURE:
<223> OTHER INFORMATION: lipocalin mutein

<400> SEQUENCE: 14

Ala Ser Asp Glu Glu Ile Gln Asp Val Ser Gly Thr Trp Tyr Leu Lys
 1               5                  10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45
```

```
Val Thr Met Asp Ile Phe Gly Phe Trp Gln Asp Val Glu Ala Val Leu
 50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Leu Ser Glu Thr Ser Ser Pro Gly Pro
145                 150
```

<210> SEQ ID NO 15
<211> LENGTH: 153
<212> TYPE: PRT
<213> ORGANISM: Artificial Sequence
<220> FEATURE:
<223> OTHER INFORMATION: lipocalin mutein

<400> SEQUENCE: 15

```
Ala Ser Asp Glu Glu Ile Gln Asp Val Ser Gly Thr Trp Tyr Leu Lys
 1               5                  10                  15

Ala Met Thr Val Asp Ser Asp Cys Phe Trp Ile Asp Asp Val Ser Val
                 20                  25                  30

Thr Pro Met Thr Leu Thr Thr Leu Glu Gly Gly Asn Leu Glu Ala Lys
             35                  40                  45

Val Thr Met Asp Ile Phe Gly Phe Trp Gln Glu Val Glu Ala Val Leu
 50                  55                  60

Glu Arg Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Pro
145                 150
```

<210> SEQ ID NO 16
<211> LENGTH: 153
<212> TYPE: PRT
<213> ORGANISM: Artificial Sequence
<220> FEATURE:
<223> OTHER INFORMATION: lipocalin mutein

<400> SEQUENCE: 16

```
Thr Ser Asp Glu Glu Ile Gln Asp Val Ser Gly Thr Trp Tyr Leu Lys
 1               5                  10                  15

Ala Met Thr Val Asp Ser Asp Cys Phe Trp Ile Asp Asp Val Ser Val
                 20                  25                  30

Thr Pro Met Thr Leu Thr Thr Leu Glu Gly Gly Asn Leu Glu Ala Lys
             35                  40                  45
```

```
Val Thr Met Asp Ile Phe Gly Phe Trp Gln Glu Val Glu Ala Val Leu
                50                  55                  60

Glu Lys Thr Asp Glu Pro Gly Lys Tyr Thr Ala Gly Gly Lys His
 65                  70                  75                  80

Val Ala Tyr Ile Asn Arg Ser His Val Lys Asp His Tyr Val Phe Tyr
                    85                  90                  95

Ser Glu Gly Glu Cys Ala Gly Tyr Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Pro
145                 150
```

<210> SEQ ID NO 17
<211> LENGTH: 153
<212> TYPE: PRT
<213> ORGANISM: Artificial Sequence
<220> FEATURE:
<223> OTHER INFORMATION: lipocalin mutein

<400> SEQUENCE: 17

```
Ala Ser Asp Glu Glu Phe Gln Asp Val Ser Gly Thr Trp Tyr Leu Lys
 1               5                  10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Glu Val Glu Ala Val Leu
        50                  55                  60

Glu Lys Thr Asp Ala Pro Gly Lys Tyr Thr Ala Asp Gly Gly Lys His
 65                  70                  75                  80

Val Ala Tyr Ile Asn Arg Ser His Glu Lys Asp His Tyr Ile Phe Tyr
                    85                  90                  95

Ser Glu Gly Glu Cys Ala Gly Tyr Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly Pro
145                 150
```

<210> SEQ ID NO 18
<211> LENGTH: 153
<212> TYPE: PRT
<213> ORGANISM: Artificial Sequence
<220> FEATURE:
<223> OTHER INFORMATION: lipocalin mutein

<400> SEQUENCE: 18

```
Thr Ser Asp Gln Glu Ile Gln Asp Val Ser Gly Thr Trp Tyr Leu Lys
 1               5                  10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
```

```
                35                  40                  45
Val Thr Met Asp Ile Phe Gly Phe Trp Gln Glu Val Glu Ala Val Leu
 50                  55                  60

Gly Lys Thr Asp Glu Pro Gly Lys Tyr Thr Ala Asp Gly Gly Lys His
 65                  70                  75                  80

Ala Ala Tyr Ile Ile Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ala Pro Gly Pro
145                 150

<210> SEQ ID NO 19
<211> LENGTH: 152
<212> TYPE: PRT
<213> ORGANISM: Artificial Sequence
<220> FEATURE:
<223> OTHER INFORMATION: lipocalin mutein

<400> SEQUENCE: 19

Ala Ser Asp Glu Glu Ile Gln Asp Val Pro Gly Thr Trp Tyr Leu Lys
 1               5                  10                  15

Ala Met Thr Val Ser Gly Glu Asp Pro Glu Met Met Leu Glu Ser Val
                20                  25                  30

Thr Pro Met Thr Leu Thr Thr Leu Glu Gly Gly Asn Leu Glu Ala Arg
            35                  40                  45

Val Thr Val Leu Ile Asp Gly Arg Cys Gln Glu Val Lys Asn Val Leu
 50                  55                  60

Glu Lys Thr Asp Glu Pro Gly Lys Tyr Thr Glu Asp Gly Gly Lys His
 65                  70                  75                  80

Val Asp Tyr Ile Ile Arg Ser His Val Lys Asp His Tyr Ile Phe Tyr
                 85                  90                  95

Phe Glu Gly Glu Gly Gln Gly Thr Pro Gly Arg Met Val Ala Leu Val
            100                 105                 110

Gly Arg Asp Pro Thr Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Cys Ser Pro Gly
145                 150

<210> SEQ ID NO 20
<211> LENGTH: 152
<212> TYPE: PRT
<213> ORGANISM: Artificial Sequence
<220> FEATURE:
<223> OTHER INFORMATION: lipocalin mutein

<400> SEQUENCE: 20

Ala Ser Asp Glu Glu Ile Gln Asp Val Pro Gly Thr Trp Tyr Leu Lys
 1               5                  10                  15

Ala Met Thr Val Ser Asp Glu Asp Pro Glu Met Thr Leu Glu Ser Val
                20                  25                  30
```

Thr Pro Met Thr Leu Thr Thr Leu Glu Gly Gly Asn Leu Glu Ala Arg
                35                  40                  45

Val Thr Val Leu Ile Asp Gly Arg Cys Gln Glu Val Lys Asn Val Leu
 50                  55                  60

Glu Lys Thr Asp Glu Pro Gly Lys Tyr Thr Glu Asp Gly Gly Lys Tyr
 65                  70                  75                  80

Val Asp Tyr Ile Ile Arg Ser His Val Lys Asp His Tyr Ile Phe Tyr
                 85                  90                  95

Phe Glu Gly Glu Gly His Gly Thr Pro Gly Arg Met Val Ala Leu Val
                100                 105                 110

Gly Arg Asp Pro Thr Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
130                 135                 140

Gln Ser Glu Thr Cys Ser Pro Gly
145                 150

<210> SEQ ID NO 21
<211> LENGTH: 152
<212> TYPE: PRT
<213> ORGANISM: Artificial Sequence
<220> FEATURE:
<223> OTHER INFORMATION: lipocalin mutein

<400> SEQUENCE: 21

Ala Ser Asp Glu Glu Ile Gln Asp Val Pro Gly Thr Trp Tyr Leu Lys
 1               5                  10                  15

Ala Met Thr Val Ser Glu Glu Asp Pro Glu Leu Thr Leu Glu Ser Val
                 20                  25                  30

Thr Pro Met Thr Leu Thr Thr Leu Glu Gly Gly Asn Leu Glu Ala Arg
                35                  40                  45

Val Thr Val Leu Ile Asp Gly Arg Cys Gln Glu Val Lys Asn Val Leu
 50                  55                  60

Glu Lys Thr Asp Glu Pro Gly Lys Tyr Thr Glu Asp Gly Gly Lys Tyr
 65                  70                  75                  80

Val Asp Tyr Ile Ile Arg Ser His Val Lys Asp His Tyr Ile Phe Tyr
                 85                  90                  95

Phe Glu Gly Glu Gly Gln Gly Thr Pro Gly Arg Met Val Ala Leu Val
                100                 105                 110

Gly Arg Asp Pro Thr Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
130                 135                 140

Gln Ser Glu Thr Cys Ser Pro Gly
145                 150

<210> SEQ ID NO 22
<211> LENGTH: 152
<212> TYPE: PRT
<213> ORGANISM: Artificial Sequence
<220> FEATURE:
<223> OTHER INFORMATION: lipocalin mutein

<400> SEQUENCE: 22

Ala Ser Asp Glu Glu Ile Gln Asp Val Pro Gly Thr Trp Tyr Leu Lys
 1               5                  10                  15

Ala Met Thr Val Ser Glu Glu Asp Pro Glu Met Thr Leu Glu Ser Val
                 20                  25                  30

```
Thr Pro Met Thr Leu Thr Thr Leu Glu Gly Gly Asn Leu Glu Ala Arg
            35                  40                  45

Val Thr Val Leu Ile Asp Gly Arg Cys Gln Glu Val Lys Asn Val Leu
 50                  55                  60

Glu Lys Thr Asp Glu Pro Gly Lys Tyr Thr Asp Gly Gly Lys Tyr
 65                  70                  75                  80

Val Asp Tyr Ile Ile Arg Ser His Val Lys Asp His Tyr Ile Phe Tyr
                85                  90                  95

Phe Glu Gly Glu Gly Glu Gly Thr Pro Gly Arg Val Val Ala Leu Val
                100                 105                 110

Gly Arg Asp Pro Thr Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
            130                 135                 140

Gln Ser Glu Thr Cys Ser Pro Gly
145                 150

<210> SEQ ID NO 23
<211> LENGTH: 152
<212> TYPE: PRT
<213> ORGANISM: Artificial Sequence
<220> FEATURE:
<223> OTHER INFORMATION: lipocalin mutein

<400> SEQUENCE: 23

Ala Ser Asp Glu Glu Ile Gln Asp Val Pro Gly Thr Trp Tyr Leu Lys
 1               5                  10                  15

Ala Met Thr Val Ser Asp Glu Asp Pro Glu Met Thr Leu Glu Ser Val
                20                  25                  30

Thr Pro Met Thr Leu Thr Thr Leu Glu Gly Gly Asn Leu Glu Ala Arg
            35                  40                  45

Val Thr Val Leu Ile Asp Gly Arg Cys Gln Glu Val Lys Asn Val Leu
 50                  55                  60

Glu Lys Thr Asp Glu Pro Gly Lys Tyr Thr Asp Gly Gly Lys Tyr
 65                  70                  75                  80

Val Asp Tyr Ile Ile Arg Ser His Val Lys Asp His Tyr Ile Phe Tyr
                85                  90                  95

Phe Glu Gly Glu Gly Gln Gly Thr Pro Gly Arg Leu Val Ala Leu Val
                100                 105                 110

Gly Arg Asp Pro Thr Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
            130                 135                 140

Gln Ser Glu Thr Cys Ser Pro Gly
145                 150

<210> SEQ ID NO 24
<211> LENGTH: 152
<212> TYPE: PRT
<213> ORGANISM: Artificial Sequence
<220> FEATURE:
<223> OTHER INFORMATION: lipocalin mutein

<400> SEQUENCE: 24

Ala Ser Asp Glu Glu Ile Gln Asp Val Pro Gly Thr Trp Tyr Leu Lys
 1               5                  10                  15

Ala Met Thr Val Ser Ser Glu Asp Pro Glu Met Thr Leu Glu Ser Val
```

```
            20                  25                  30
Thr Pro Met Thr Leu Thr Thr Leu Glu Gly Gly Asn Leu Glu Ala Arg
        35                  40                  45
Val Thr Val Leu Ile Asp Gly Arg Cys Gln Glu Val Lys Asn Val Leu
    50                  55                  60
Glu Lys Thr Asp Glu Pro Gly Lys Tyr Thr Glu Asp Gly Gly Lys Tyr
65                  70                  75                  80
Val Asp Tyr Ile Ile Arg Ser His Val Lys Asp His Tyr Ile Phe Tyr
                85                  90                  95
Phe Glu Gly Glu Gly Gln Gly Thr Pro Gly Arg Met Val Ala Leu Val
            100                 105                 110
Gly Arg Asp Pro Thr Asn Asn Leu Glu Ala Leu Glu Asp Phe Glu Lys
        115                 120                 125
Ala Ala Gly Ala Arg Gly Leu Ser Thr Glu Ser Ile Leu Ile Pro Arg
    130                 135                 140
Gln Ser Glu Thr Cys Ser Pro Gly
145                 150

<210> SEQ ID NO 25
<211> LENGTH: 152
<212> TYPE: PRT
<213> ORGANISM: Artificial Sequence
<220> FEATURE:
<223> OTHER INFORMATION: lipocalin mutein

<400> SEQUENCE: 25

Ala Ser Asp Glu Glu Ile Gln Asp Val Pro Gly Thr Trp Tyr Leu Lys
1               5                   10                  15
Ala Met Thr Val Ser Ala Glu Asp Pro Glu Met Thr Leu Glu Ser Val
            20                  25                  30
Thr Pro Met Thr Leu Thr Thr Leu Glu Gly Gly Asn Leu Glu Ala Arg
        35                  40                  45
Val Thr Val Leu Ile Asp Gly Arg Cys Gln Glu Val Lys Asn Val Leu
    50                  55                  60
Glu Lys Thr Asp Glu Pro Gly Lys Tyr Thr Glu Asp Gly Gly Lys Tyr
65                  70                  75                  80
Val Asp Tyr Ile Ile Arg Ser His Val Lys Asp His Tyr Ile Phe Tyr
                85                  90                  95
Phe Glu Gly Glu Gly Lys Gly Thr Pro Gly Arg Met Val Ala Leu Val
            100                 105                 110
Gly Arg Asp Pro Thr Asn Asn Leu Glu Ala Leu Glu Asp Phe Glu Lys
        115                 120                 125
Ala Ala Gly Ala Arg Gly Leu Ser Thr Glu Ser Ile Leu Ile Pro Arg
    130                 135                 140
Gln Ser Glu Thr Cys Ser Pro Gly
145                 150

<210> SEQ ID NO 26
<211> LENGTH: 152
<212> TYPE: PRT
<213> ORGANISM: Artificial Sequence
<220> FEATURE:
<223> OTHER INFORMATION: lipocalin mutein

<400> SEQUENCE: 26

Ala Ser Asp Glu Glu Ile Gln Asp Val Pro Gly Thr Trp Tyr Leu Lys
1               5                   10                  15
```

Ala Met Thr Val Ser Arg Glu Asp Pro Glu Met Thr Leu Glu Ser Val
            20                  25                  30

Thr Pro Met Thr Leu Thr Thr Leu Glu Gly Gly Asn Leu Glu Ala Arg
            35                  40                  45

Val Thr Val Leu Ile Asp Gly Arg Cys Gln Glu Val Lys Asn Val Leu
    50                  55                  60

Glu Lys Thr Asp Glu Pro Gly Lys Tyr Thr Glu Asp Gly Gly Lys His
65                  70                  75                  80

Val Asp Tyr Ile Ile Arg Ser His Val Lys Asp His Tyr Ile Phe Tyr
                85                  90                  95

Phe Glu Gly Glu Gly Gln Gly Thr Pro Asn Arg Met Ala Ala Leu Val
            100                 105                 110

Gly Arg Asp Pro Thr Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Cys Ser Pro Gly
145                 150

<210> SEQ ID NO 27
<211> LENGTH: 152
<212> TYPE: PRT
<213> ORGANISM: Artificial Sequence
<220> FEATURE:
<223> OTHER INFORMATION: lipocalin mutein

<400> SEQUENCE: 27

Ala Ser Asp Glu Glu Ile Gln Asp Val Pro Gly Thr Trp Tyr Leu Lys
1               5                   10                  15

Ala Met Thr Val Ser Gly Glu Asp Pro Glu Leu Thr Leu Glu Ser Val
            20                  25                  30

Thr Pro Met Thr Leu Thr Thr Leu Glu Gly Gly Asn Leu Glu Ala Arg
            35                  40                  45

Val Thr Val Leu Ile Asp Gly Arg Cys Gln Glu Val Lys Asn Val Leu
    50                  55                  60

Glu Lys Thr Asp Glu Pro Gly Lys Tyr Thr Glu Asp Gly Gly Lys Tyr
65                  70                  75                  80

Val Asp Tyr Ile Ile Arg Ser His Val Lys Asp His Tyr Ile Phe Tyr
                85                  90                  95

Phe Glu Gly Glu Gly Pro Gly Thr Pro Gly Arg Met Val Ala Leu Val
            100                 105                 110

Gly Arg Asp Pro Thr Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Cys Ser Pro Gly
145                 150

<210> SEQ ID NO 28
<211> LENGTH: 152
<212> TYPE: PRT
<213> ORGANISM: Artificial Sequence
<220> FEATURE:
<223> OTHER INFORMATION: lipocalin mutein

<400> SEQUENCE: 28

Ala Ser Asp Glu Glu Ile Gln Asp Val Pro Gly Thr Trp Tyr Leu Lys
1               5                   10                  15

Ala Met Thr Val Ser Asp Glu Asp Pro Glu Met Thr Leu Glu Ser Val
            20                  25                  30

Thr Pro Met Thr Leu Thr Thr Leu Glu Gly Gly Asn Leu Glu Ala Arg
        35                  40                  45

Val Thr Val Leu Ile Asp Gly Arg Cys Gln Val Lys Asn Val Leu
 50                  55                  60

Glu Lys Thr Asp Glu Pro Gly Lys Tyr Thr Glu Asp Gly Gly Lys Leu
 65                  70                  75                  80

Val Asp Tyr Ile Ile Arg Ser His Val Lys Asp His Tyr Ile Phe Tyr
                85                  90                  95

Phe Glu Gly Glu Gly Gln Gly Thr Pro Gly Arg Met Leu Ala Leu Val
            100                 105                 110

Gly Arg Asp Pro Thr Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Cys Ser Pro Gly
145                 150

<210> SEQ ID NO 29
<211> LENGTH: 456
<212> TYPE: DNA
<213> ORGANISM: Artificial Sequence
<220> FEATURE:
<223> OTHER INFORMATION: lipocalin mutein

<400> SEQUENCE: 29
gcctcagacg aggagattca ggatgtgtca gggacgtggt atctgaaggc catgacggtg      60
gattctgatt gctttggat tgatgatgtg tcagttacgc caatgactct gactacccct     120
gaaggcggca atctggaggc taaggtcacc atggatattt ttggcttttg caggaagtg    180 aaagcagtgt tagagaagac agatgaaccg ggtaaatata cggccgatgg cggcaaacat     240
gttgcctata tcattcgcag ccatgtgaaa gatcattaca tcttttatag cgagggcgaa     300
tgcgctggct atccggttcc aggggtgtgg ctcgtgggca gagacccaa gaacaacctg     360 gaagccttgg aggactttga aaagccgca ggagcccgcg gactcagcac ggagagcatc     420
ctcatcccca ggcagagcga aaccagctct ccaggg                               456

<210> SEQ ID NO 30
<211> LENGTH: 459
<212> TYPE: DNA
<213> ORGANISM: Artificial Sequence
<220> FEATURE:
<223> OTHER INFORMATION: lipocalin mutein

<400> SEQUENCE: 30
acctcagact aggagattca ggatgtgtca gggacgtggt atctgaaggc gatgacggtg      60
gattccgatt gcttttggat tgatgatgtg tcagttacgc caatgactct gactacccct    120
gaaggcggca atctggaggc taaggtcacc atggatattt ttggcttttg caggaagtg    180 gaagcagtgt tagggaagac agatgaaccg ggtaaatata cggccgatgg cggcaaacat     240
gctgcctata tcattcgcag ccatgtgaaa gatcattaca tcttttatag cgagggcgaa     300
tgcgctggct atccggttcc gggggtgtgg ctcgtgggca gagacccaa gaacaacctg     360 gaagccttgg aggacttcga aaagccgca ggagcccgcg gactcagcac ggagagcatc     420
ctcatcccca ggcagagcga aaccagcgct ccagggcca                            459

<210> SEQ ID NO 31
<211> LENGTH: 459
<212> TYPE: DNA
<213> ORGANISM: Artificial Sequence
<220> FEATURE:
<223> OTHER INFORMATION: lipocalin mutein

<400> SEQUENCE: 31

```
acctcagacg aggagattca ggatgtgtca gggacgtggt atctgaaggc gatgacggtg      60
gattctgatt gcttttggat tgatgatgtg tcagttacgc caatgactct gactaccctt     120
gaagacggca atctggaggc taaggtcacc atggatattt ttggcttttg gcaggaagtg     180
gaagcagtgt tagagaagac agatgagccg ggtaaatata cggccgatgg cggcaaacat     240
gctgcctata tcattcgcag ccatgtgaaa gatcattaca tctttttatag cgagggcgaa     300
tgcgctggct atccggttcc gggggtgtgg ctcgtgggca gagaccccaa gaacaacctg     360
gaagccttgg aggactttga gaaagccgca ggagcccgcg gactcagcac ggagagcatc     420
ctcatcccca ggcagggcga aaccagctct ccagggcca                            459
```

<210> SEQ ID NO 32
<211> LENGTH: 459
<212> TYPE: DNA
<213> ORGANISM: Artificial Sequence
<220> FEATURE:
<223> OTHER INFORMATION: lipocalin mutein

<400> SEQUENCE: 32

```
gcctcaggcg aggagattca ggatgtgtca gggacgtggt atctgaaggc gatgacggtg      60
gattctgatt gcttttggat tgatgatgtg tcagttacgc caatgactct gactaccctt     120
gaaggcggca atctggaggc taaggtcacc atggatattt ttggcttttg gcaggaagtg     180
aaagcagtgt tagagaagac agatgaaccg ggtaaatata cggccgatgg cggcaaacat     240
gatgcctata tcattcgcag ccatgtgaaa gatcattaca tctttttatag cgagggcgaa     300
tgcgctggct atccggttcc gggggtgtgg ctcgtgggca gagaccccaa gaacaacctg     360
gaagccttgg aggactttga gaaagccgca ggagcccgcg gactcagcac ggagagcatc     420
ctcatcccct ggcagagcga acccagctct ccagggcca                            459
```

<210> SEQ ID NO 33
<211> LENGTH: 459
<212> TYPE: DNA
<213> ORGANISM: Artificial Sequence
<220> FEATURE:
<223> OTHER INFORMATION: lipocalin mutein

<400> SEQUENCE: 33

```
acctcagacg aggagattca ggatgtgtca gggacgtggt atctgaaggc gatgacggtg      60
gattctgatt gcttttggat tgatgatgtg tcagttacgc caatgactct gactaccctt     120
gaaggcggca atctggaggc taaggccacc atggatattt ttggcttttg gcaggaagtg     180
gaagcagtgt tagagaagac agatgaaccg ggtaaatata cgaccgatgg cggcaaacat     240
gttgcctata tcattcgcag ccatgtgaaa gatcatcaca tctttttatag cgagggcgaa     300
tgcgctggct atccggttcc gggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccagggcca                            459
```

<210> SEQ ID NO 34
<211> LENGTH: 459
<212> TYPE: DNA
<213> ORGANISM: Artificial Sequence
<220> FEATURE:
<223> OTHER INFORMATION: lipocalin mutein

<400> SEQUENCE: 34

| gcctcagacg | aggagattca | ggatgtgtct | gggacgtggt | atctgaaggc | gatgacggtg | 60 |
| gattctgatt | gcttttggat | tgatgatgtg | tcagttacgc | caatgactct | gactacccct | 120 |
| gaaggcggca | atctggaggc | taaggtcacc | atggatattt | ttggcttttg | gcaggatgtg | 180 |
| aaagcagtgt | tagagaagac | agatgaaccg | ggtaagtata | cggccgatgg | cggcaaacat | 240 |
| gatgcctata | tcattagcag | tcatgtgaaa | gataattaca | tcttttatag | cgagggcgaa | 300 |
| tgcgctggct | atccggttcc | ggggggtgtgg | ctcgtgggca | gagaccccaa | gaacaaccag | 360 |
| gaagccttgg | aggactttga | gaaagccgca | ggagcccgcg | gactcagcac | ggagagcatc | 420 |
| ctcatcccca | ggcagagcga | aaccagctct | ccagggcca | | | 459 |

<210> SEQ ID NO 35
<211> LENGTH: 459
<212> TYPE: DNA
<213> ORGANISM: Artificial Sequence
<220> FEATURE:
<223> OTHER INFORMATION: lipocalin mutein

<400> SEQUENCE: 35

| gcctcagacg | aggagattca | ggatgtgtca | gggatgtggt | atctgaaggc | gatgacggtg | 60 |
| gattctgatt | gcttttggat | tgatgatgtg | tcagttacgc | caatgactct | gactacccat | 120 |
| gaaggcggca | atctggaggc | taaggtcacc | atggatattt | ttggcttttg | gcaggaagtg | 180 |
| gaagcagtgt | tagagaagac | agatgaaccg | ggtaaatata | cggccgatgg | cggcaaacat | 240 |
| gtggcctata | tcagtcgcag | ccatgtgaaa | gatcattaca | tcttttatag | cgagggcgaa | 300 |
| tgcgctggct | atccggttcc | ggggggtgtgg | ctcgtgggca | gagaccccaa | gaacaacctg | 360 |
| gaagccttgg | aggactttga | gaaagccgca | ggagcccgcg | gactcagcac | ggagagcatc | 420 |
| ctcatcccca | ggcagagcga | aaccagctct | ccagggcca | | | 459 |

<210> SEQ ID NO 36
<211> LENGTH: 459
<212> TYPE: DNA
<213> ORGANISM: Artificial Sequence
<220> FEATURE:
<223> OTHER INFORMATION: lipocalin mutein

<400> SEQUENCE: 36

| gcctcagacg | aggagattca | ggatgtgtca | gggacgtggt | atctgaaggc | gatgacggtg | 60 |
| gattctgatt | gcttttggat | tgatgatgtg | tcagttacgc | caatgactct | gactacccct | 120 |
| gaaggcggca | atctggaggc | taaggtcacc | atggatattt | ttggcttttg | gcaggatgtg | 180 |
| gaagcagtgt | tagagaagac | agatgaaccg | ggtaaatata | ccgccgatgg | cggcaaacat | 240 |
| gttgcctata | tcattcgcag | ccatgtgaaa | gatcattaca | tcttttatag | cgagggcgaa | 300 |
| tgcgctggct | atccggttcc | ggggggtgtgg | ctcgtgggca | gagaccccaa | gaacaacctg | 360 |
| gaagccttgg | aggactttga | gaaagctgca | ggagcccgcg | gactcagtac | ggagagcatc | 420 |
| ctcatcccca | ggctgagcga | aaccagctct | ccagggcca | | | 459 |

```
<210> SEQ ID NO 37
<211> LENGTH: 459
<212> TYPE: DNA
<213> ORGANISM: Artificial Sequence
<220> FEATURE:
<223> OTHER INFORMATION: lipocalin mutein

<400> SEQUENCE: 37
gcctcagacg aggagattca ggatgtgtca gggacgtggt atctgaaggc gatgacggtg      60
gattctgatt gcttttggat tgatgatgtg tcagttacgc caatgactct gactacccett     120
gaaggcggca atctggaggc taaggtcacc atggatattt ttggcttttg gcaggaagtg     180
gaagcagtgt tagagaggac agatgaaccg ggtaaatata cggccgatgg cggcaaacat     240
gttgcctata tcattcgcag ccatgtgaaa gatcattaca tcttttatag cgagggcgaa     300
tgcgctggct atccggttcc gggggtgtgg ctcgtgggca gacccccaa gaacaacctg      360
gaagccttgg aggactttga gaaagccgca ggagcccgcg gactcagcac ggagagcatc     420
ctcatcccca ggcagagcga aaccagctct ccagggcca                            459

<210> SEQ ID NO 38
<211> LENGTH: 459
<212> TYPE: DNA
<213> ORGANISM: Artificial Sequence
<220> FEATURE:
<223> OTHER INFORMATION: lipocalin mutein

<400> SEQUENCE: 38
acctcagacg aggagattca ggatgtgtca gggacgtggt atctgaaggc gatgacggtg      60
gattctgatt gcttttggat tgatgatgtg tcagttacgc caatgactct gactacccett     120
gaaggcggca atctggaggc taaggtcacc atggatattt ttggcttttg gcaggaagtg     180
gaagcagtgt tagaaaagac agatgaaccg ggtaaatata cggccggtgg cggcaaacat     240
gttgcctata tcaatcgcag ccatgtgaaa gatcattacg tcttttatag cgagggcgaa     300
tgcgctggct atccggttcc gggggtgtgg ctcgtgggca gacccccaa gaacaacctg      360
gaagccttgg aggactttga gaaagccgca ggagcccgcg gactcagcac ggagagtatc     420
ctcatcccca ggcagagcga aaccagctct ccagggcca                            459

<210> SEQ ID NO 39
<211> LENGTH: 459
<212> TYPE: DNA
<213> ORGANISM: Artificial Sequence
<220> FEATURE:
<223> OTHER INFORMATION: lipocalin mutein

<400> SEQUENCE: 39
gcctcagacg aggagtttca ggatgtgtca gggacgtggt atctgaaggc gatgacggtg      60
gattctgatt gcttttggat tgatgatgtg tcagttacgc caatgactct gactacccett     120
gaaggcggca atctggaggc taaggtcacc atggatattt ttggcttttg gcaggaagtg     180
gaagcagtgt tagagaagac agatgcaccg ggtaaatata cagccgatgg aggcaaacat     240
gttgcctata tcaatcgcag ccatgagaaa gatcattaca tcttttatag cgagggcgaa     300
tgcgctggct atccggtacc gggggtgtgg ctcgtgggca gacccccaa gaacaacctg      360
gaagccttgg aggactttga gaaagccgca ggagcccgcg gactcagcac ggagagcatc     420
ctcatcccca ggcagagcga aaccagctct ccagggcca                            459

<210> SEQ ID NO 40
```

<211> LENGTH: 459
<212> TYPE: DNA
<213> ORGANISM: Artificial Sequence
<220> FEATURE:
<223> OTHER INFORMATION: lipocalin mutein

<400> SEQUENCE: 40

```
acctcagacc aggagattca ggatgtgtca gggacgtggt atctgaaggc gatgacggtg    60
gattccgatt gcttttggat tgatgatgtg tcagttacgc aatgactct gactacccctt   120
gaaggcggca atctggaggc taaggtcacc atggatattt ttggcttttg gcaggaagtg   180
gaagcagtgt tagggaagac agatgaaccg ggtaaatata cggccgatgg cggcaaacat   240
gctgcctata tcattcgcag ccatgtgaaa gatcattaca tcttttatag cgagggcgaa   300
tgcgctggct atccggttcc ggggtgtgg ctcgtgggca gagacccaa gaacaacctg     360
gaagccttgg aggacttcga gaaagccgca ggagcccgcg gactcagcac ggagagcatc   420
ctcatcccca ggcagagcga aaccagcgct ccagggcca                          459
```

<210> SEQ ID NO 41
<211> LENGTH: 456
<212> TYPE: DNA
<213> ORGANISM: Artificial Sequence
<220> FEATURE:
<223> OTHER INFORMATION: lipocalin mutein

<400> SEQUENCE: 41

```
gcctcagacg aggagattca ggatgtgcca gggacgtggt atctgaaagc gatgacggtt    60
tcgggggaag atcctgagat gatgctggaa tcagttacgc aatgactct gactacccctt   120
gaaggcggca atctggaggc tcgtgtgacc gttctgattg atggccgctg ccaggaagtg   180
aaaaatgtgc tcgagaagac agatgaaccg ggtaaataca cggaggatgg cggcaaacat   240
gtggattata tcattagatc tcatgtgaaa gatcattaca tcttctactt tgaaggcgaa   300
gggcagggca cgccgggtcg catggtggct ctggtgggca gagacccac caataatctg    360
gaagccttgg aggactttga gaaagccgca ggagcccgcg gactcagcac ggagagcatc   420
ctcatcccca ggcagagcga aacctgctct ccaggg                             456
```

<210> SEQ ID NO 42
<211> LENGTH: 456
<212> TYPE: DNA
<213> ORGANISM: Artificial Sequence
<220> FEATURE:
<223> OTHER INFORMATION: lipocalin mutein

<400> SEQUENCE: 42

```
gcctcagacg aggagattca ggatgtgcca gggacgtggt atctgaaagc gatgacggtt    60
agcgatgaag atccggaaat gaccctggaa tcagttacgc aatgactct gactacccctt   120
gaaggcggca atctggaggc tagggtgacc gttctgattg atggccgctg ccaggaagtg   180
aaaaacgtgc tcgagaagac agatgaaccg ggtaaataca cggaagatgg cggcaaatat   240
gtggattata tcattagatc tcatgtgaaa gatcattaca tcttctactt tgaaggcgaa   300
ggccatggca ccccggggag gatggtggcc ctggtgggca gagacccac caataatctg    360
gaagccttgg aggactttga gaaagccgca ggagcccgcg gactcagcac ggagagcatc   420
ctcatcccca ggcagagcga aacctgctct ccaggg                             456
```

<210> SEQ ID NO 43
<211> LENGTH: 456

<212> TYPE: DNA
<213> ORGANISM: Artificial Sequence
<220> FEATURE:
<223> OTHER INFORMATION: lipocalin mutein

<400> SEQUENCE: 43

```
gcctcagacg aggagattca ggatgtgcca gggacgtggt atctgaaagc gatgacggtt    60
agcgaggaag atccggaatt gaccctggaa tcagttacgc caatgactct gactacccttt   120
gaaggcggca atctggaggc tagggtgacc gttctgattg atggccgctg ccaggaagtg   180
aaaaacgtgc tcgagaagac agatgaaccg ggtaaataca cggaagatgg cggcaaatat   240
gtggattata tcattagatc tcatgtgaaa gatcattaca tcttctactt tgaaggcgaa   300
ggccagggca ccccgggtag gatggtggcc ctggtgggca gagaccccac caataatctg   360
gaagccttgg aggactttga gaaagccgca ggagcccgcg gactcagcac ggagagcatc   420
ctcatcccca ggcagagcga aacctgctct ccaggg                             456
```

<210> SEQ ID NO 44
<211> LENGTH: 456
<212> TYPE: DNA
<213> ORGANISM: Artificial Sequence
<220> FEATURE:
<223> OTHER INFORMATION: lipocalin mutein

<400> SEQUENCE: 44

```
gcctcagacg aggagattca ggatgtgcca gggacgtggt atctgaaagc gatgacggtt    60
agcgaggaag atccggaaat gaccctggaa tcagttacgc caatgactct gactacccttt   120
gaaggcggca atctggaggc tagggtgacc gttctgattg atggccgctg ccaggaagtg   180
aaaaacgtgc tcgagaagac agatgaaccg ggtaaataca cggaagatgg cggcaaatat   240
gtggattata tcattagatc tcatgtgaaa gatcattaca tcttctactt tgaaggcgaa   300
ggcgagggca ccccggggag ggtggtggcc ctggtgggca gagaccccac caataatctg   360
gaagccttgg aggactttga gaaagccgca ggagcccgcg gactcagcac ggagagcatc   420
ctcatcccca ggcagagcga aacctgctct ccaggg                             456
```

<210> SEQ ID NO 45
<211> LENGTH: 456
<212> TYPE: DNA
<213> ORGANISM: Artificial Sequence
<220> FEATURE:
<223> OTHER INFORMATION: lipocalin mutein

<400> SEQUENCE: 45

```
gcctcagacg aggagattca ggatgtgcca gggacgtggt atctgaaagc gatgacggtt    60
agcgatgaag atccggaaat gaccctggaa tcagttacgc caatgactct gactacccttt   120
gaaggcggca atctggaggc tagggtgacc gttctgattg atggccgctg ccaggaagtg   180
aaaaacgtgc tcgagaagac agatgaaccg ggtaaataca cggaagatgg cggcaaatat   240
gtggattata tcattagatc tcatgtgaaa gatcattaca tcttctactt tgaaggcgaa   300
ggccagggca ccccggggag gttggtggcc ctggtgggca gagaccccac caataatctg   360
gaagccttgg aggactttga gaaagccgca ggagcccgcg gactcagcac ggagagcatc   420
ctcatcccca ggcagagcga aacctgctct ccaggg                             456
```

<210> SEQ ID NO 46
<211> LENGTH: 456
<212> TYPE: DNA

<213> ORGANISM: Artificial Sequence
<220> FEATURE:
<223> OTHER INFORMATION: lipocalin mutein

<400> SEQUENCE: 46

```
gcctcagacg aggagattca ggatgtgcca gggacgtggt atctgaaagc gatgacggtt    60
agcagtgaag atccggaaat gaccctggaa tcagttacgc caatgactct gactacccct   120
gaaggcggca atctggaggc tagggtgacc gtgctgattg atggccgctg ccaggaagtg   180
aaaaacgtgc tcgagaagac agatgaaccg ggtaaataca cggaagatgg cggcaaatat   240
gtggattata tcattagatc tcatgtgaaa gatcattaca tcttctactt tgaaggcgaa   300
ggccagggca ccccgggtag gatggttgcc ctggtgggca gagaccccac caataatctg   360
gaagccttgg aggactttga gaaagccgca ggagcccgcg gactcagcac ggagagcatc   420
ctcatcccca ggcagagcga aacctgctct ccaggg                             456
```

<210> SEQ ID NO 47
<211> LENGTH: 456
<212> TYPE: DNA
<213> ORGANISM: Artificial Sequence
<220> FEATURE:
<223> OTHER INFORMATION: lipocalin mutein

<400> SEQUENCE: 47

```
gcctcagacg aggagattca ggatgtgcca gggacgtggt atctgaaagc gatgacggtt    60
agcgctgaag atccggaaat gaccctggaa tcagttacgc caatgactct gactacccct   120
gaaggcggca atctggaggc tagggtgacc gttctgattg atggccgctg ccaggaagtg   180
aaaaacgtgc tcgagaagac agatgaaccg ggtaaataca cggaagatgg cggcaaatat   240
gtggattata tcattagatc tcatgtgaaa gatcattaca tcttctactt tgaaggcgaa   300
ggcaagggca ccccggggag gatggtggcc ctggtgggca gagaccccac caataatctg   360
gaagccttgg aggactttga gaaagccgca ggagcccgcg gactcagcac ggagagcatc   420
ctcatcccca ggcagagcga aacctgctct ccaggg                             456
```

<210> SEQ ID NO 48
<211> LENGTH: 456
<212> TYPE: DNA
<213> ORGANISM: Artificial Sequence
<220> FEATURE:
<223> OTHER INFORMATION: lipocalin mutein

<400> SEQUENCE: 48

```
gcctcagacg aggagattca ggatgtgcca gggacgtggt atctgaaagc gatgacggtt    60
agccgtgaag atccggaaat gaccctggaa tcagttacgc caatgactct gactacccct   120
gaaggcggca atctggaggc tagggtgacc gttctgattg atggccgctg ccaggaagtg   180
aaaaacgtgc tcgagaagac agatgaaccg ggtaaataca cggaagatgg cggcaaacat   240
gtggattata tcattagatc tcatgtgaaa gatcattaca tcttctactt tgaaggcgaa   300
ggccagggca ccccgaatag gatggcggcc ctggtgggca gagaccccac caataatctg   360
gaagccttgg aggactttga gaaagccgca ggagcccgcg gactcagcac ggagagcatc   420
ctcatcccca ggcagagcga aacctgctct ccaggg                             456
```

<210> SEQ ID NO 49
<211> LENGTH: 456
<212> TYPE: DNA
<213> ORGANISM: Artificial Sequence
<220> FEATURE:
<223> OTHER INFORMATION: lipocalin mutein

<400> SEQUENCE: 49

```
gcctcagacg aggagattca ggatgtgcca gggacgtggt atctgaaagc gatgacggtt      60
agcggggaag atccggaatt gaccctggaa tcagttacgc caatgactct gactacccct    120
gaaggcggca atctggaggc tagggtgacc gtgctgattg atggccgctg ccaggaagtg    180
aaaaacgtgc tcgagaagac agatgaaccg ggtaaataca cggaagatgg cggcaaaatat   240
gtggattata tcattagatc tcatgtgaaa gatcattaca tcttctactt tgaaggcgaa    300
ggccctggca ccccgggtag gatggtgccc ctggtgggca gagaccccac caataatctg    360
gaagccttgg aggactttga gaaagccgca ggagcccgcg gactcagcac ggagagcatc    420
ctcatcccca ggcagagcga aacctgctct ccaggg                              456
```

<210> SEQ ID NO 50
<211> LENGTH: 456
<212> TYPE: DNA
<213> ORGANISM: Artificial Sequence
<220> FEATURE:
<223> OTHER INFORMATION: lipocalin mutein

<400> SEQUENCE: 50

```
gcctcagacg aggagattca ggatgtgcca gggacgtggt atctgaaagc gatgacggtt      60
agcgatgaag atccggaaat gaccctggaa tcagttacgc caatgactct gactacccct    120
gaaggcggca atctggaggc tagggtgacc gtgctgattg atggccgctg ccaggaagtg    180
aaaaacgtgc tcgagaagac agatgaaccg ggtaaataca cggaagatgg cggcaaactt    240
gtggattata tcattagatc tcatgtgaaa gatcattaca tcttctactt tgaaggcgaa    300
ggccagggca ccccgggtag gatgctggcc ctggtgggca gagaccccac caataatctg    360
gaagccttgg aggactttga gaaagccgca ggagcccgcg gactcagcac ggagagcatc    420
ctcatcccca ggcagagcga aacctgctct ccaggg                              456
```

<210> SEQ ID NO 51
<211> LENGTH: 4
<212> TYPE: PRT
<213> ORGANISM: Homo sapiens

<400> SEQUENCE: 51

His His Leu Leu
1

<210> SEQ ID NO 52
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 52

Ile Glu Gly Arg
1

<210> SEQ ID NO 53
<211> LENGTH: 10
<212> TYPE: PRT
<213> ORGANISM: Artificial Sequence
<220> FEATURE:
<223> OTHER INFORMATION: SA linker and strep-tag II fusion peptide

```
<400> SEQUENCE: 53

Ser Ala Trp Ser His Pro Gln Phe Glu Lys
1               5                   10

<210> SEQ ID NO 54
<211> LENGTH: 8
<212> TYPE: PRT
<213> ORGANISM: Artificial Sequence
<220> FEATURE:
<223> OTHER INFORMATION: Strep-tag II peptide

<400> SEQUENCE: 54

Trp Ser His Pro Gln Phe Glu Lys
1               5

<210> SEQ ID NO 55
<211> LENGTH: 15
<212> TYPE: PRT
<213> ORGANISM: Artificial Sequence
<220> FEATURE:
<223> OTHER INFORMATION: (G4S)3 Linker

<400> SEQUENCE: 55

Gly Gly Gly Gly Ser Gly Gly Gly Gly Ser Gly Gly Gly Gly Ser
1               5                   10                  15

<210> SEQ ID NO 56
<211> LENGTH: 676
<212> TYPE: PRT
<213> ORGANISM: Artificial Sequence
<220> FEATURE:
<223> OTHER INFORMATION: cynoLAG-3 Fc fusion protein

<400> SEQUENCE: 56

Pro Gln Pro Gly Ala Glu Ile Ser Val Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Pro Ala Pro Gly His Pro Val Pro Gly His Arg Pro
        50                  55                  60

Ala Ala Pro Tyr Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Thr
            115                 120                 125

Val His Leu Arg Asp Arg Ala Leu Ser Cys Arg Leu Arg Leu Arg Val
        130                 135                 140

Gly Gln Ala Ser Met Thr Ala Ser Pro Pro Gly Ser Leu Arg Thr Ser
145                 150                 155                 160

Asp Trp Val Ile Leu Asn Cys Ser Phe Ser Arg Pro Asp Arg Pro Ala
                165                 170                 175

Ser Val His Trp Phe Arg Ser Arg Gly Gln Gly Arg Val Pro Val Gln
                180                 185                 190

Gly Ser Pro His His Leu Ala Glu Ser Phe Leu Phe Leu Pro His
            195                 200                 205
```

-continued

```
Val Gly Pro Met Asp Ser Gly Leu Trp Gly Cys Ile Leu Thr Tyr Arg
    210                 215                 220

Asp Gly Phe Asn Val Ser Ile Met Tyr Asn Leu Thr Val Leu Gly Leu
225                 230                 235                 240

Glu Pro Ala Thr Pro Leu Thr Val Tyr Ala Gly Ala Gly Ser Arg Val
                245                 250                 255

Glu Leu Pro Cys Arg Leu Pro Pro Ala Val Gly Thr Gln Ser Phe Leu
            260                 265                 270

Thr Ala Lys Trp Ala Pro Pro Gly Gly Pro Asp Leu Leu Val Ala
        275                 280                 285

Gly Asp Asn Gly Asp Phe Thr Leu Arg Leu Glu Asp Val Ser Gln Ala
290                 295                 300

Gln Ala Gly Thr Tyr Ile Cys His Ile Arg Leu Gln Gly Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Ala
                340                 345                 350

Ser Gly Gln Glu His Phe Val Trp Ser Pro Leu Asn Thr Pro Ser Gln
            355                 360                 365

Arg Ser Phe Ser Gly Pro Trp Leu Glu Ala Gln Glu Ala Gln Leu Leu
        370                 375                 380

Ser Gln Pro Trp Gln Cys Gln Leu His Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Arg Ala Gly His Leu Ile Glu Gly Arg
                420                 425                 430

Met Asp Gly Gly Gly Gly Ser Gly Gly Gly Ser Gly Gly Gly Gly
            435                 440                 445

Ser Asp Lys Thr His Thr Cys Pro Pro Cys Pro Ala Pro Glu Leu Leu
450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
            515                 520                 525

Tyr Arg Val Val Ser Val Leu Thr Val Leu His Gln Asp Trp Leu Asn
        530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Glu Glu Met Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
610                 615                 620
```

```
Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
            645                 650                 655

Met His Glu Ala Leu His Asn His Tyr Thr Gln Lys Ser Leu Ser Leu
        660                 665                 670

Ser Pro Gly Lys
        675

<210> SEQ ID NO 57
<211> LENGTH: 152
<212> TYPE: PRT
<213> ORGANISM: Artificial Sequence
<220> FEATURE:
<223> OTHER INFORMATION: lipocalin mutein

<400> SEQUENCE: 57

Thr Ser Asp Gln Glu Ile Gln Asp Val Ser Gly Thr Trp Tyr Leu Lys
1               5                   10                  15

Ala Met Thr Val Asp Ser Asp Cys Phe Trp Ile Asp Val Ser Val
            20                  25                  30

Thr Pro Met Thr Leu Thr Thr Leu Arg Gly Gly Asn Leu Glu Ala Lys
        35                  40                  45

Val Thr Met Asp Ile Phe Gly Phe Trp Gln Glu Val Glu Ala Val Leu
50                  55                  60

Gly Lys Thr Asp Arg Pro Gly Lys Tyr Thr Ala Gly Gly Lys His
65                  70                  75                  80

Ala Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ala Pro Gly
145                 150

<210> SEQ ID NO 58
<211> LENGTH: 152
<212> TYPE: PRT
<213> ORGANISM: Artificial Sequence
<220> FEATURE:
<223> OTHER INFORMATION: lipocalin mutein

<400> SEQUENCE: 58

Thr Ser Asn Gln Gln Ile Gln Asn Val Ser Gly Thr Trp Tyr Leu Lys
1               5                   10                  15

Ala Met Thr Val Asp Ser Asp Cys Phe Trp Ile Asp Val Ser Val
            20                  25                  30

Thr Pro Met Thr Leu Thr Thr Leu Arg Gly Gly Asn Leu Glu Ala Lys
        35                  40                  45

Val Thr Met Asp Ile Phe Gly Phe Trp Gln Glu Val Glu Ala Val Leu
50                  55                  60

Gly Lys Thr Asn Arg Pro Gly Lys Tyr Thr Ala Gly Gly Lys His
65                  70                  75                  80

Ala Ala Tyr Ile Ile Arg Ser His Val Lys Asn His Tyr Ile Phe Tyr
                85                  90                  95
```

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ala Pro Gly
145                 150

<210> SEQ ID NO 59
<211> LENGTH: 152
<212> TYPE: PRT
<213> ORGANISM: Artificial Sequence
<220> FEATURE:
<223> OTHER INFORMATION: lipocalin mutein

<400> SEQUENCE: 59

Thr Ser Arg Gln Arg Ile Gln Arg Val Ser Gly Thr Trp Tyr Leu Lys
1               5                   10                  15

Ala Met Thr Val Asp Ser Asp Cys Phe Trp Ile Asp Asp Val Ser Val
            20                  25                  30

Thr Pro Met Thr Leu Thr Thr Leu Arg Gly Gly Asn Leu Glu Ala Lys
        35                  40                  45

Val Thr Met Asp Ile Phe Gly Phe Trp Gln Glu Val Glu Ala Val Leu
    50                  55                  60

Gly Lys Thr Arg Arg Pro Gly Lys Tyr Thr Ala Gly Gly Lys His
65              70                  75                  80

Ala Ala Tyr Ile Ile Arg Ser His Val Lys Arg His Tyr Ile Phe Tyr
            85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ala Pro Gly
145                 150

<210> SEQ ID NO 60
<211> LENGTH: 152
<212> TYPE: PRT
<213> ORGANISM: Artificial Sequence
<220> FEATURE:
<223> OTHER INFORMATION: lipocalin mutein

<400> SEQUENCE: 60

Thr Ser Lys Gln Lys Ile Gln Lys Val Ser Gly Thr Trp Tyr Leu Lys
1               5                   10                  15

Ala Met Thr Val Asp Ser Asp Cys Phe Trp Ile Asp Asp Val Ser Val
            20                  25                  30

Thr Pro Met Thr Leu Thr Thr Leu Arg Gly Gly Asn Leu Glu Ala Lys
        35                  40                  45

Val Thr Met Asp Ile Phe Gly Phe Trp Gln Glu Val Glu Ala Val Leu
    50                  55                  60

Gly Lys Thr Lys Arg Pro Gly Lys Tyr Thr Ala Gly Gly Lys His
65              70                  75                  80

Ala Ala Tyr Ile Ile Arg Ser His Val Lys Lys His Tyr Ile Phe Tyr

```
              85                  90                  95
Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ala Pro Gly
145                 150

<210> SEQ ID NO 61
<211> LENGTH: 152
<212> TYPE: PRT
<213> ORGANISM: Artificial Sequence
<220> FEATURE:
<223> OTHER INFORMATION: lipocalin mutein

<400> SEQUENCE: 61

Thr Ser Asn Gln Gln Ile Gln Asn Val Ser Gly Thr Trp Tyr Leu Lys
1               5                   10                  15

Ala Met Thr Val Asp Ser Asp Cys Phe Trp Ile Asp Asp Val Ser Val
            20                  25                  30

Thr Pro Met Thr Leu Thr Thr Leu Arg Gly Gly Asn Leu Glu Ala Lys
        35                  40                  45

Val Thr Met Asp Ile Phe Gly Phe Trp Gln Glu Val Glu Ala Val Leu
    50                  55                  60

Gly Lys Thr Asp Arg Pro Gly Lys Tyr Thr Ala Gly Gly Lys His
65                  70                  75                  80

Ala Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ala Pro Gly
145                 150

<210> SEQ ID NO 62
<211> LENGTH: 152
<212> TYPE: PRT
<213> ORGANISM: Artificial Sequence
<220> FEATURE:
<223> OTHER INFORMATION: lipocalin mutein

<400> SEQUENCE: 62

Thr Ser Asn Gln Gln Ile Gln Asn Val Ser Gly Thr Trp Tyr Leu Lys
1               5                   10                  15

Ala Met Thr Val Asp Ser Asp Cys Phe Trp Ile Asp Asp Val Ser Val
            20                  25                  30

Thr Pro Met Thr Leu Thr Thr Leu Arg Gly Gly Asn Leu Glu Ala Lys
        35                  40                  45

Val Thr Met Asp Ile Phe Gly Phe Trp Gln Glu Val Glu Ala Val Leu
    50                  55                  60

Gly Lys Thr Asn Arg Pro Gly Lys Tyr Thr Ala Gly Gly Lys His
65                  70                  75                  80
```

```
Ala Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ala Pro Gly
145                 150
```

<210> SEQ ID NO 63
<211> LENGTH: 152
<212> TYPE: PRT
<213> ORGANISM: Artificial Sequence
<220> FEATURE:
<223> OTHER INFORMATION: lipocalin mutein

<400> SEQUENCE: 63

```
Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Val Ser Val
            20                  25                  30

Thr Pro Met Thr Leu Thr Thr Leu Arg Gly Gly Asn Leu Glu Ala Lys
            35                  40                  45

Val Thr Met Asp Ile Phe Gly Phe Trp Gln Glu Val Glu Ala Val Leu
        50                  55                  60

Glu Arg Thr Asp Arg Pro Gly Lys Tyr Thr Ala Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150
```

<210> SEQ ID NO 64
<211> LENGTH: 152
<212> TYPE: PRT
<213> ORGANISM: Artificial Sequence
<220> FEATURE:
<223> OTHER INFORMATION: lipocalin mutein

<400> SEQUENCE: 64

```
Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Val Ser Val
            20                  25                  30

Thr Pro Met Thr Leu Thr Thr Leu Glu Gly Gly Asn Leu Glu Ala Lys
            35                  40                  45

Val Thr Met Asp Ile Phe Gly Phe Cys Gln Glu Val Glu Ala Val Leu
        50                  55                  60

Glu Arg Thr Asp Glu Pro Gly Lys Tyr Thr Ala Asp Gly Gly Lys His
65                  70                  75                  80
```

```
Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Cys Ser Pro Gly
145                 150

<210> SEQ ID NO 65
<211> LENGTH: 152
<212> TYPE: PRT
<213> ORGANISM: Artificial Sequence
<220> FEATURE:
<223> OTHER INFORMATION: lipocalin mutein

<400> SEQUENCE: 65

Thr Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
            20                  25                  30

Thr Pro Met Thr Leu Thr Thr Leu Glu Gly Gly Asn Leu Glu Ala Lys
        35                  40                  45

Val Thr Met Asp Ile Phe Gly Phe Trp Gln Glu Val Glu Ala Val Leu
    50                  55                  60

Glu Arg Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 66
<211> LENGTH: 152
<212> TYPE: PRT
<213> ORGANISM: Artificial Sequence
<220> FEATURE:
<223> OTHER INFORMATION: lipocalin mutein

<400> SEQUENCE: 66

Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
            20                  25                  30

Thr Pro Met Thr Leu Thr Thr Leu Arg Gly Gly Asn Leu Glu Ala Lys
        35                  40                  45

Val Thr Met Asp Ile Phe Gly Phe Trp Gln Asp Val Glu Ala Val Leu
    50                  55                  60

Glu Lys Thr Asp Arg Pro Gly Lys Tyr Thr Ala Gly Gly Gly Lys His
```

```
                65                  70                  75                  80
Val Ala Tyr Ile Ile Arg Ser His Val Lys Asp His Tyr Ile Phe Tyr
                    85                  90                  95

Ser Glu Gly Glu Cys Ala Gly Tyr Pro Val Pro Gly Val Trp Leu Val
                   100                 105                 110

Gly Arg Asp Pro Lys Asn Asn Leu Glu Ala Leu Glu Asp Phe Glu Lys
                   115                 120                 125

Ala Ala Gly Ala Arg Gly Leu Ser Thr Glu Ser Ile Leu Ile Pro Arg
    130                 135                 140

Leu Ser Glu Thr Ser Ser Pro Gly
145                 150

<210> SEQ ID NO 67
<211> LENGTH: 152
<212> TYPE: PRT
<213> ORGANISM: Artificial Sequence
<220> FEATURE:
<223> OTHER INFORMATION: lipocalin mutein

<400> SEQUENCE: 67

Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Cys Gln Asp Val Glu Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                    85                  90                  95

Ser Glu Gly Glu Cys Ala Gly Tyr Pro Val Pro Gly Val Trp Leu Val
                   100                 105                 110

Gly Arg Asp Pro Lys Asn Asn Leu Glu Ala Leu Glu Asp Phe Glu Lys
                   115                 120                 125

Ala Ala Gly Ala Arg Gly Leu Ser Thr Glu Ser Ile Leu Ile Pro Arg
    130                 135                 140

Leu Ser Glu Thr Cys Ser Pro Gly
145                 150

<210> SEQ ID NO 68
<211> LENGTH: 152
<212> TYPE: PRT
<213> ORGANISM: Artificial Sequence
<220> FEATURE:
<223> OTHER INFORMATION: lipocalin mutein

<400> SEQUENCE: 68

Thr Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Asp Val Glu Ala Val Leu
    50                  55                  60
```

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
            130                 135                 140

Leu Ser Glu Thr Ser Ser Pro Gly
145                 150

<210> SEQ ID NO 69
<211> LENGTH: 152
<212> TYPE: PRT
<213> ORGANISM: Artificial Sequence
<220> FEATURE:
<223> OTHER INFORMATION: lipocalin mutein

<400> SEQUENCE: 69

Ala Ser Asp Glu Glu Ile Gln Asn Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Asp Val Glu Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
            130                 135                 140

Leu Ser Glu Thr Ser Ser Pro Gly
145                 150

<210> SEQ ID NO 70
<211> LENGTH: 152
<212> TYPE: PRT
<213> ORGANISM: Artificial Sequence
<220> FEATURE:
<223> OTHER INFORMATION: lipocalin mutein

<400> SEQUENCE: 70

Ala Ser Asp Glu Glu Ile Gln Asn Val Ser Gly Thr Trp Tyr Leu Lys
1               5                   10                  15

Ala Met Thr Val Asp Ser Asp Cys Phe Trp Ile Asp Asp Val Ser Val
                20                  25                  30

Thr Pro Met Thr Leu Thr Thr Leu Glu Gly Gly Asn Leu Glu Ala Lys
            35                  40                  45

Val Thr Met Asp Ile Phe Gly Phe Cys Gln Asp Val Glu Ala Val Leu
    50                  55                  60

Glu Lys Thr Asp Glu Pro Gly Lys Tyr Thr Ala Asp Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Leu Ser Glu Thr Cys Ser Pro Gly
145                 150

<210> SEQ ID NO 71
<211> LENGTH: 456
<212> TYPE: DNA
<213> ORGANISM: Artificial Sequence
<220> FEATURE:
<223> OTHER INFORMATION: lipocalin mutein

<400> SEQUENCE: 71
acctcagacc aggagattca ggatgtgtca gggacgtggt atctgaaggc gatgacggtg      60
gattccgatt gcttttggat tgatgatgtg tcagttacgc caatgactct gactacccttt    120 cgcggcggca atctggaggc taaggtcacc atggatattt ttggcttttg gcaggaagtg    180
gaagcagtgt tagggaagac agatcgcccg ggtaaatata cggccggcgg cggcaaacat    240
gctgcctata tcattcgcag ccatgtgaaa gatcattaca tcttttatag cgagggcgaa    300
tgcgctggct atccggttcc ggggtgtgg ctcgtgggca gagacccaa gaacaacctg     360 gaagccttgg aggacttcga gaagccgca ggagcccgcg gactcagcac ggagagcatc    420
ctcatcccca ggcagagcga aaccagcgct ccaggg                              456

<210> SEQ ID NO 72
<211> LENGTH: 456
<212> TYPE: DNA
<213> ORGANISM: Artificial Sequence
<220> FEATURE:
<223> OTHER INFORMATION: lipocalin mutein

<400> SEQUENCE: 72
acctcaaacc agcagattca gaacgtgtca gggacgtggt atctgaaggc gatgacggtg      60
gattccgatt gcttttggat tgatgatgtg tcagttacgc caatgactct gactacccttt    120 cgcggcggca atctggaggc taaggtcacc atggatattt ttggcttttg gcaggaagtg    180
gaagcagtgt tagggaagac aaaccgcccg ggtaaatata cggccggcgg cggcaaacat    240
gctgcctata tcattcgcag ccatgtgaaa aaccattaca tcttttatag cgagggcgaa    300
tgcgctggct atccggttcc ggggtgtgg ctcgtgggca gagacccaa gaacaacctg     360 gaagccttgg aggacttcga gaagccgca ggagcccgcg gactcagcac ggagagcatc    420
ctcatcccca ggcagagcga aaccagcgct ccaggg                              456

<210> SEQ ID NO 73
<211> LENGTH: 456
<212> TYPE: DNA
<213> ORGANISM: Artificial Sequence
<220> FEATURE:
<223> OTHER INFORMATION: lipocalin mutein -continued

<400> SEQUENCE: 73

| acctcacgtc agcgtattca gcgtgtgtca gggacgtggt atctgaaggc gatgacggtg | 60 |
| gattccgatt gcttttggat tgatgatgtg tcagttacgc caatgactct gactacccatt | 120 |
| cgcggcggca atctggaggc taaggtcacc atggatattt ttggcttttg gcaggaagtg | 180 |
| gaagcagtgt tagggaagac acgtcgcccg ggtaaatata cggccggcgg cggcaaacat | 240 |
| gctgcctata tcattcgcag ccatgtgaaa aaccattaca tcttttatag cgagggcgaa | 300 |
| tgcgctggct atccggttcc ggggggtgtgg ctcgtgggca gagaccccaa gaacaacctg | 360 |
| gaagccttgg aggacttcga gaaagccgca ggagcccgcg gactcagcac ggagagcatc | 420 |
| ctcatccccca ggcagagcga aaccagcgct ccaggg | 456 |

<210> SEQ ID NO 74
<211> LENGTH: 456
<212> TYPE: DNA
<213> ORGANISM: Artificial Sequence
<220> FEATURE:
<223> OTHER INFORMATION: lipocalin mutein

<400> SEQUENCE: 74

| acctcaaaac agaaaattca gaaagtgtca gggacgtggt atctgaaggc gatgacggtg | 60 |
| gattccgatt gcttttggat tgatgatgtg tcagttacgc caatgactct gactacccctt | 120 |
| cgcggcggca atctggaggc taaggtcacc atggatattt ttggcttttg gcaggaagtg | 180 |
| gaagcagtgt tagggaagac aaaacgcccg ggtaaatata cggccggcgg cggcaaacat | 240 |
| gctgcctata tcattcgcag ccatgtgaaa aaccattaca tcttttatag cgagggcgaa | 300 |
| tgcgctggct atccggttcc ggggggtgtgg ctcgtgggca gagaccccaa gaacaacctg | 360 |
| gaagccttgg aggacttcga gaaagccgca ggagcccgcg gactcagcac ggagagcatc | 420 |
| ctcatccccca ggcagagcga aaccagcgct ccaggg | 456 |

<210> SEQ ID NO 75
<211> LENGTH: 456
<212> TYPE: DNA
<213> ORGANISM: Artificial Sequence
<220> FEATURE:
<223> OTHER INFORMATION: lipocalin mutein

<400> SEQUENCE: 75

| acctcagacc aggagattca ggatgtgtca gggacgtggt atctgaaggc gatgacggtg | 60 |
| gattccgatt gcttttggat tgatgatgtg tcagttacgc caatgactct gactacccctt | 120 |
| gaaggcggca atctggaggc taaggtcacc atggatattt ttggcttttg ccaggaagtg | 180 |
| gaagcagtgt tagggaagac agatgaaccg ggtaaatata cggccgatgg cggcaaacat | 240 |
| gctgcctata tcattcgcag ccatgtgaaa gatcattaca tcttttatag cgagggcgaa | 300 |
| tgcgctggct atccggttcc ggggggtgtgg ctcgtgggca gagaccccaa gaacaacctg | 360 |
| gaagccttgg aggacttcga gaaagccgca ggagcccgcg gactcagcac ggagagcatc | 420 |
| ctcatccccca ggcagagcga aacctgcgct ccaggg | 456 |

<210> SEQ ID NO 76
<211> LENGTH: 456
<212> TYPE: DNA
<213> ORGANISM: Artificial Sequence
<220> FEATURE:
<223> OTHER INFORMATION: lipocalin mutein

<400> SEQUENCE: 76

```
acctcagacc aggagattca gaatgtgtca gggacgtggt atctgaaggc gatgacggtg      60
gattccgatt gcttttggat tgatgatgtg tcagttacgc caatgactct gactacccct     120
gaaggcggca atctggaggc taaggtcacc atggatattt ttggcttttg gcaggaagtg     180
gaagcagtgt tagggaagac agatgaaccg gtaaaatata cggccgatgg cggcaaacat     240
gctgcctata tcattcgcag ccatgtgaaa gatcattaca tcttttatag cgagggcgaa     300
tgcgctggct atccggttcc gggggtgtgg ctcgtgggca gagaccccaa gaacaacctg     360
gaagccttgg aggacttcga gaaagccgca ggagcccgcg gactcagcac ggagagcatc     420
ctcatcccca ggcagagcga aaccagcgct ccaggg                              456

<210> SEQ ID NO 77
<211> LENGTH: 456
<212> TYPE: DNA
<213> ORGANISM: Artificial Sequence
<220> FEATURE:
<223> OTHER INFORMATION: lipocalin mutein

<400> SEQUENCE: 77
gcctcagacg aggagattca ggatgtgtca gggacgtggt atctgaaggc gatgacggtg      60
gattctgatt gcttttggat tgatgatgtg tcagttacgc caatgactct gactacccct     120
cgcggcggca atctggaggc taaggtcacc atggatattt ttggcttttg gcaggaagtg     180
gaagcagtgt tagagaggac agatcgcccg gtaaaatata cggccggcgg cggcaaacat     240
gttgcctata tcattcgcag ccatgtgaaa gatcattaca tcttttatag cgagggcgaa     300
tgcgctggct atccggttcc gggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aaccagctct ccaggg                              456

<210> SEQ ID NO 78
<211> LENGTH: 456
<212> TYPE: DNA
<213> ORGANISM: Artificial Sequence
<220> FEATURE:
<223> OTHER INFORMATION: lipocalin mutein

<400> SEQUENCE: 78
gcctcagacg aggagattca ggatgtgtca gggacgtggt atctgaaggc gatgacggtg      60
gattctgatt gcttttggat tgatgatgtg tcagttacgc caatgactct gactacccct     120
gaaggcggca atctggaggc taaggtcacc atggatattt ttggcttttg ccaggaagtg     180
gaagcagtgt tagagaggac agatgaaccg gtaaaatata cggccgatgg cggcaaacat     240
gttgcctata tcattcgcag ccatgtgaaa gatcattaca tcttttatag cgagggcgaa     300
tgcgctggct atccggttcc gggggtgtgg ctcgtgggca gagaccccaa gaacaacctg     360
gaagccttgg aggactttga gaaagccgca ggagcccgcg gactcagcac ggagagcatc     420
ctcatcccca ggcagagcga aacctgctct ccaggg                              456

<210> SEQ ID NO 79
<211> LENGTH: 456
<212> TYPE: DNA
<213> ORGANISM: Artificial Sequence
<220> FEATURE:
<223> OTHER INFORMATION: lipocalin mutein

<400> SEQUENCE: 79
```

```
acctcagacg aggagattca ggatgtgtca gggacgtggt atctgaaggc gatgacggtg      60
gattctgatt gcttttggat tgatgatgtg tcagttacgc caatgactct gactacccct     120
gaaggcggca atctggaggc taaggtcacc atggatattt ttggcttttg gcaggaagtg     180
gaagcagtgt tagagaggac agatgaaccg ggtaaatata cggccgatgg cggcaaacat     240
gttgcctata tcattcgcag ccatgtgaaa gatcattaca tctttatag cgagggcgaa     300 tgcgctggct atccggttcc ggggtgtgg ctcgtgggca gagacccaa gaacaacctg      360 gaagccttgg aggactttga gaaagccgca ggagcccgcg gactcagcac ggagagcatc    420
ctcatcccca ggcagagcga aaccagctct ccaggg                              456

<210> SEQ ID NO 80
<211> LENGTH: 456
<212> TYPE: DNA
<213> ORGANISM: Artificial Sequence
<220> FEATURE:
<223> OTHER INFORMATION: lipocalin mutein

<400> SEQUENCE: 80
gcctcagacg aggagattca ggatgtgtca gggacgtggt atctgaaggc gatgacggtg      60
gattctgatt gcttttggat tgatgatgtg tcagttacgc caatgactct gactacccct     120
cgcggcggca atctggaggc taaggtcacc atggatattt ttggcttttg gcaggatgtg     180
gaagcagtgt tagagaagac agatcgcccg ggtaaatata ccgccggcgg cggcaaacat     240
gttgcctata tcattcgcag ccatgtgaaa gatcattaca tctttatag cgagggcgaa     300 tgcgctggct atccggttcc ggggtgtgg ctcgtgggca gagacccaa gaacaacctg      360 gaagccttgg aggactttga gaaagctgca ggagcccgcg gactcagtac ggagagcatc    420
ctcatcccca ggctgagcga aaccagctct ccaggg                              456

<210> SEQ ID NO 81
<211> LENGTH: 456
<212> TYPE: DNA
<213> ORGANISM: Artificial Sequence
<220> FEATURE:
<223> OTHER INFORMATION: lipocalin mutein

<400> SEQUENCE: 81
gcctcagacg aggagattca ggatgtgtca gggacgtggt atctgaaggc gatgacggtg      60
gattctgatt gcttttggat tgatgatgtg tcagttacgc caatgactct gactacccct     120
gaaggcggca atctggaggc taaggtcacc atggatattt ttggcttttg ccaggatgtg     180
gaagcagtgt tagagaagac agatgaaccg ggtaaatata ccgccgatgg cggcaaacat     240
gttgcctata tcattcgcag ccatgtgaaa gatcattaca tctttatag cgagggcgaa     300 tgcgctggct atccggttcc ggggtgtgg ctcgtgggca gagacccaa gaacaacctg      360 gaagccttgg aggactttga gaaagctgca ggagcccgcg gactcagtac ggagagcatc    420
ctcatcccca ggctgagcga aacctgctct ccaggg                              456

<210> SEQ ID NO 82
<211> LENGTH: 456
<212> TYPE: DNA
<213> ORGANISM: Artificial Sequence
<220> FEATURE:
<223> OTHER INFORMATION: lipocalin mutein

<400> SEQUENCE: 82
acctcagacg aggagattca ggatgtgtca gggacgtggt atctgaaggc gatgacggtg      60
```

```
gattctgatt gcttttggat tgatgatgtg tcagttacgc caatgactct gactaccctt    120
gaaggcggca atctggaggc taaggtcacc atggatattt ttggcttttg gcaggatgtg    180
gaagcagtgt tagagaagac agatgaaccg ggtaaatata ccgccgatgg cggcaaacat    240
gttgcctata tcattcgcag ccatgtgaaa gatcattaca tcttttatag cgagggcgaa    300
tgcgctggct atccggttcc ggggtgtgg ctcgtgggca gagacccaa gaacaacctg       360 gaagccttgg aggactttga aaagctgca ggagcccgcg gactcagtac ggagagcatc      420
ctcatcccca ggctgagcga aaccagctct ccaggg                                456
```

<210> SEQ ID NO 83
<211> LENGTH: 456
<212> TYPE: DNA
<213> ORGANISM: Artificial Sequence
<220> FEATURE:
<223> OTHER INFORMATION: lipocalin mutein

<400> SEQUENCE: 83

```
gcctcagacg aggagattca gaatgtgtca gggacgtggt atctgaaggc gatgacggtg     60
gattctgatt gcttttggat tgatgatgtg tcagttacgc caatgactct gactaccctt    120
gaaggcggca atctggaggc taaggtcacc atggatattt ttggcttttg gcaggatgtg    180
gaagcagtgt tagagaagac agatgaaccg ggtaaatata ccgccgatgg cggcaaacat    240
gttgcctata tcattcgcag ccatgtgaaa gatcattaca tcttttatag cgagggcgaa    300
tgcgctggct atccggttcc ggggtgtgg ctcgtgggca gagacccaa gaacaacctg       360 gaagccttgg aggactttga aaagctgca ggagcccgcg gactcagtac ggagagcatc      420
ctcatcccca ggctgagcga aaccagctct ccaggg                                456
```

<210> SEQ ID NO 84
<211> LENGTH: 456
<212> TYPE: DNA
<213> ORGANISM: Artificial Sequence
<220> FEATURE:
<223> OTHER INFORMATION: lipocalin mutein

<400> SEQUENCE: 84

```
gcctcagacg aggagattca gaatgtgtca gggacgtggt atctgaaggc gatgacggtg     60
gattctgatt gcttttggat tgatgatgtg tcagttacgc caatgactct gactaccctt    120
gaaggcggca atctggaggc taaggtcacc atggatattt ttggcttttg ccaggatgtg    180
gaagcagtgt tagagaagac agatgaaccg ggtaaatata ccgccgatgg cggcaaacat    240
gttgcctata tcattcgcag ccatgtgaaa gatcattaca tcttttatag cgagggcgaa    300
tgcgctggct atccggttcc ggggtgtgg ctcgtgggca gagacccaa gaacaacctg       360 gaagccttgg aggactttga aaagctgca ggagcccgcg gactcagtac ggagagcatc      420
ctcatcccca ggctgagcga aacctgctct ccaggg                                456
```

<210> SEQ ID NO 85
<211> LENGTH: 152
<212> TYPE: PRT
<213> ORGANISM: Artificial Sequence
<220> FEATURE:
<223> OTHER INFORMATION: lipocalin mutein

<400> SEQUENCE: 85

```
Thr Ser Asp Gln Glu Ile Gln Asp Val Ser Gly Thr Trp Tyr Leu Lys
1               5                   10                  15
```

```
Ala Met Thr Val Asp Ser Asp Cys Phe Trp Ile Asp Val Ser Val
            20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Glu Val Glu Ala Val Leu
 50                  55                  60

Gly Lys Thr Asp Glu Pro Gly Lys Tyr Thr Ala Asp Gly Gly Lys His
 65                  70                  75                  80

Ala Ala Tyr Ile Ile Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ala Pro Gly
145                 150
```

<210> SEQ ID NO 86
<211> LENGTH: 152
<212> TYPE: PRT
<213> ORGANISM: Artificial Sequence
<220> FEATURE:
<223> OTHER INFORMATION: lipocalin mutein

<400> SEQUENCE: 86

```
Thr Ser Asp Glu Glu Ile Gln Asp Val Ser Gly Thr Trp Tyr Leu Lys
 1               5                  10                  15

Ala Met Thr Val Asp Ser Asp Cys Phe Trp Ile Asp Val Ser Val
            20                  25                  30

Thr Pro Met Thr Leu Thr Thr Leu Glu Asp Gly Asn Leu Glu Ala Lys
            35                  40                  45

Val Thr Met Asp Ile Phe Gly Phe Trp Gln Glu Val Glu Ala Val Leu
 50                  55                  60

Glu Lys Thr Asp Glu Pro Gly Lys Tyr Thr Ala Asp Gly Gly Lys His
 65                  70                  75                  80

Ala Ala Tyr Ile Ile Arg Ser His Val Lys Asp His Tyr Ile Phe Tyr
                 85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Gly Glu Thr Ser Ser Pro Gly
145                 150
```

<210> SEQ ID NO 87
<211> LENGTH: 152
<212> TYPE: PRT
<213> ORGANISM: Artificial Sequence
<220> FEATURE:
<223> OTHER INFORMATION: lipocalin mutein

<400> SEQUENCE: 87

```
Ala Ser Gly Glu Glu Ile Gln Asp Val Ser Gly Thr Trp Tyr Leu Lys
```

```
                1               5                  10                 15
Ala Met Thr Val Asp Ser Asp Cys Phe Trp Ile Asp Val Ser Val
                20                 25                 30

Thr Pro Met Thr Leu Thr Thr Leu Glu Gly Gly Asn Leu Glu Ala Lys
                35                 40                 45

Val Thr Met Asp Ile Phe Gly Phe Trp Gln Glu Val Lys Ala Val Leu
            50                 55                 60

Glu Lys Thr Asp Glu Pro Gly Lys Tyr Thr Ala Asp Gly Gly Lys His
65                  70                 75                 80

Asp Ala Tyr Ile Ile Arg Ser His Val Lys Asp His Tyr Ile Phe Tyr
                    85                 90                 95

Ser Glu Gly Glu Cys Ala Gly Tyr Pro Val Pro Gly Val Trp Leu Val
                100                105                110

Gly Arg Asp Pro Lys Asn Asn Leu Glu Ala Leu Glu Asp Phe Glu Lys
                115                120                125

Ala Ala Gly Ala Arg Gly Leu Ser Thr Glu Ser Ile Leu Ile Pro Trp
            130                135                140

Gln Ser Glu Pro Ser Ser Pro Gly
145                 150
```

<210> SEQ ID NO 88
<211> LENGTH: 152
<212> TYPE: PRT
<213> ORGANISM: Artificial Sequence
<220> FEATURE:
<223> OTHER INFORMATION: lipocalin mutein

<400> SEQUENCE: 88

```
Thr Ser Asp Glu Glu Ile Gln Asp Val Ser Gly Thr Trp Tyr Leu Lys
1               5                  10                 15

Ala Met Thr Val Asp Ser Asp Cys Phe Trp Ile Asp Val Ser Val
                20                 25                 30

Thr Pro Met Thr Leu Thr Thr Leu Glu Gly Gly Asn Leu Glu Ala Lys
                35                 40                 45

Ala Thr Met Asp Ile Phe Gly Phe Trp Gln Glu Val Glu Ala Val Leu
            50                 55                 60

Glu Lys Thr Asp Glu Pro Gly Lys Tyr Thr Thr Asp Gly Gly Lys His
65                  70                 75                 80

Val Ala Tyr Ile Ile Arg Ser His Val Lys Asp His His Ile Phe Tyr
                    85                 90                 95

Ser Glu Gly Glu Cys Ala Gly Tyr Pro Val Pro Gly Val Trp Leu Val
                100                105                110

Gly Arg Asp Pro Lys Asn Asn Leu Glu Ala Leu Glu Asp Phe Glu Lys
                115                120                125

Ala Ala Gly Ala Arg Gly Leu Ser Thr Glu Ser Ile Leu Ile Pro Arg
            130                135                140

Gln Ser Glu Thr Ser Ser Pro Gly
145                 150
```

<210> SEQ ID NO 89
<211> LENGTH: 152
<212> TYPE: PRT
<213> ORGANISM: Artificial Sequence
<220> FEATURE:
<223> OTHER INFORMATION: lipocalin mutein

<400> SEQUENCE: 89

Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Val Ser Val
            20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Asp Val Lys Ala Val Leu
        50                  55                  60

Glu Lys Thr Asp Glu Pro Gly Lys Tyr Thr Ala Asp Gly Gly Lys His
65                  70                  75                  80

Asp Ala Tyr Ile Ile Ser Ser His Val Lys Asp Asn Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Gln Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 90
<211> LENGTH: 152
<212> TYPE: PRT
<213> ORGANISM: Artificial Sequence
<220> FEATURE:
<223> OTHER INFORMATION: lipocalin mutein

<400> SEQUENCE: 90

Ala Ser Asp Glu Glu Ile Gln Asp Val Ser Gly Met Trp Tyr Leu Lys
1               5                   10                  15

Ala Met Thr Val Asp Ser Asp Cys Phe Trp Ile Asp Asp Val Ser Val
            20                  25                  30

Thr Pro Met Thr Leu Thr Thr His Glu Gly Gly Asn Leu Glu Ala Lys
            35                  40                  45

Val Thr Met Asp Ile Phe Gly Phe Trp Gln Glu Val Glu Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ser Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
        130                 135                 140

Gln Ser Glu Thr Ser Ser Pro Gly
145                 150

<210> SEQ ID NO 91
<211> LENGTH: 152
<212> TYPE: PRT
<213> ORGANISM: Artificial Sequence
<220> FEATURE:
<223> OTHER INFORMATION: lipocalin mutein

<400> SEQUENCE: 91

```
Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Val Ser Val
            20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Asp Val Glu Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Leu Ser Glu Thr Ser Ser Pro Gly
145                 150
```

<210> SEQ ID NO 92
<211> LENGTH: 152
<212> TYPE: PRT
<213> ORGANISM: Artificial Sequence
<220> FEATURE:
<223> OTHER INFORMATION: lipocalin mutein

<400> SEQUENCE: 92

```
Ala Ser Asp Glu Glu Ile Gln Asp Val Ser Gly Thr Trp Tyr Leu Lys
1               5                   10                  15

Ala Met Thr Val Asp Ser Asp Cys Phe Trp Ile Asp Val Ser Val
            20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Glu Val Glu Ala Val Leu
    50                  55                  60

Glu Arg Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150
```

<210> SEQ ID NO 93
<211> LENGTH: 152
<212> TYPE: PRT
<213> ORGANISM: Artificial Sequence
<220> FEATURE:
<223> OTHER INFORMATION: lipocalin mutein -continued

<400> SEQUENCE: 93

```
Thr Ser Asp Glu Glu Ile Gln Asp Val Ser Gly Thr Trp Tyr Leu Lys
1               5                   10                  15
Ala Met Thr Val Asp Ser Asp Cys Phe Trp Ile Asp Asp Val Ser Val
            20                  25                  30
Thr Pro Met Thr Leu Thr Thr Leu Glu Gly Gly Asn Leu Glu Ala Lys
        35                  40                  45
Val Thr Met Asp Ile Phe Gly Phe Trp Gln Glu Val Glu Ala Val Leu
    50                  55                  60
Glu Lys Thr Asp Glu Pro Gly Lys Tyr Thr Ala Gly Gly Lys His
65                  70                  75                  80
Val Ala Tyr Ile Asn Arg Ser His Val Lys Asp His Tyr Val Phe Tyr
                85                  90                  95
Ser Glu Gly Glu Cys Ala Gly Tyr Pro Val Pro Gly Val Trp Leu Val
            100                 105                 110
Gly Arg Asp Pro Lys Asn Asn Leu Glu Ala Leu Glu Asp Phe Glu Lys
        115                 120                 125
Ala Ala Gly Ala Arg Gly Leu Ser Thr Glu Ser Ile Leu Ile Pro Arg
    130                 135                 140
Gln Ser Glu Thr Ser Ser Pro Gly
145                 150
```

<210> SEQ ID NO 94
<211> LENGTH: 152
<212> TYPE: PRT
<213> ORGANISM: Artificial Sequence
<220> FEATURE:
<223> OTHER INFORMATION: lipocalin mutein

<400> SEQUENCE: 94

```
Ala Ser Asp Glu Glu Phe Gln Asp Val Ser Gly Thr Trp Tyr Leu Lys
1               5                   10                  15
Ala Met Thr Val Asp Ser Asp Cys Phe Trp Ile Asp Asp Val Ser Val
            20                  25                  30
Thr Pro Met Thr Leu Thr Thr Leu Glu Gly Gly Asn Leu Glu Ala Lys
        35                  40                  45
Val Thr Met Asp Ile Phe Gly Phe Trp Gln Glu Val Glu Ala Val Leu
    50                  55                  60
Glu Lys Thr Asp Ala Pro Gly Lys Tyr Thr Ala Asp Gly Gly Lys His
65                  70                  75                  80
Val Ala Tyr Ile Asn Arg Ser His Glu Lys Asp His Tyr Ile Phe Tyr
                85                  90                  95
Ser Glu Gly Glu Cys Ala Gly Tyr Pro Val Pro Gly Val Trp Leu Val
            100                 105                 110
Gly Arg Asp Pro Lys Asn Asn Leu Glu Ala Leu Glu Asp Phe Glu Lys
        115                 120                 125
Ala Ala Gly Ala Arg Gly Leu Ser Thr Glu Ser Ile Leu Ile Pro Arg
    130                 135                 140
Gln Ser Glu Thr Ser Ser Pro Gly
145                 150
```

<210> SEQ ID NO 95
<211> LENGTH: 152
<212> TYPE: PRT
<213> ORGANISM: Artificial Sequence
<220> FEATURE:
<223> OTHER INFORMATION: lipocalin mutein

<400> SEQUENCE: 95

| Thr | Ser | Asp | Gln | Glu | Ile | Gln | Asp | Val | Ser | Gly | Thr | Trp | Tyr | Leu | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ala Met Thr Val Asp Ser Asp Cys Phe Trp Ile Asp Asp Val Ser Val
              20                  25                  30

Thr Pro Met Thr Leu Thr Thr Leu Glu Gly Gly Asn Leu Glu Ala Lys
            35                  40                  45

Val Thr Met Asp Ile Phe Gly Phe Trp Gln Glu Glu Ala Val Leu
    50                  55                  60

Gly Lys Thr Asp Glu Pro Gly Lys Tyr Thr Ala Asp Gly Gly Lys His
65              70                  75                  80

Ala Ala Tyr Ile Ile Arg Ser His Val Lys Asp His Tyr Ile Phe Tyr
                85                  90                  95

Ser Glu Gly Glu Cys Ala Gly Tyr Pro Val Pro Gly Val Trp Leu Val
                100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
130                 135                 140

Gln Ser Glu Thr Ser Ala Pro Gly
145                 150

<210> SEQ ID NO 96
<211> LENGTH: 456
<212> TYPE: DNA
<213> ORGANISM: Artificial Sequence
<220> FEATURE:
<223> OTHER INFORMATION: lipocalin mutein

<400> SEQUENCE: 96

```
acctcagact aggagattca ggatgtgtca gggacgtggt atctgaaggc gatgacggtg      60
gattccgatt gcttttggat tgatgatgtg tcagttacgc caatgactct gactacccett    120
gaaggcggca atctggaggc taaggtcacc atggatattt ttggcttttg gcaggaagtg    180
gaagcagtgt tagggaagac agatgaaccg ggtaaatata cggccgatgg cggcaaacat    240
gctgcctata tcattcgcag ccatgtgaaa gatcattaca tcttttatag cgagggcgaa    300
tgcgctggct atccggttcc gggggtgtgg ctcgtgggca gagacccaa gaacaacctg    360
gaagccttgg aggacttcga gaaagccgca ggagcccgcg gactcagcac ggagagcatc    420
ctcatcccca ggcagagcga aaccagcgct ccaggg                              456
```

<210> SEQ ID NO 97
<211> LENGTH: 456
<212> TYPE: DNA
<213> ORGANISM: Artificial Sequence
<220> FEATURE:
<223> OTHER INFORMATION: lipocalin mutein

<400> SEQUENCE: 97

```
acctcagacg aggagattca ggatgtgtca gggacgtggt atctgaaggc gatgacggtg      60
gattctgatt gcttttggat tgatgatgtg tcagttacgc caatgactct gactacccett    120
gaagacggca atctggaggc taaggtcacc atggatattt ttggcttttg gcaggaagtg    180
gaagcagtgt tagagaagac agatgagccg ggtaaatata cggccgatgg cggcaaacat    240
gctgcctata tcattcgcag ccatgtgaaa gatcattaca tcttttatag cgagggcgaa    300
```

| | |
|---|---|
| tgcgctggct atccggttcc gggggtgtgg ctcgtgggca gagaccccaa gaacaacctg | 360 |
| gaagccttgg aggactttga aaagccgca ggagcccgcg gactcagcac ggagagcatc | 420 |
| ctcatcccca ggcagggcga aaccagctct ccaggg | 456 |

<210> SEQ ID NO 98
<211> LENGTH: 456
<212> TYPE: DNA
<213> ORGANISM: Artificial Sequence
<220> FEATURE:
<223> OTHER INFORMATION: lipocalin mutein

<400> SEQUENCE: 98

| | |
|---|---|
| gcctcaggcg aggagattca ggatgtgtca gggacgtggt atctgaaggc gatgacggtg | 60 |
| gattctgatt gcttttggat tgatgatgtg tcagttacgc caatgactct gactacccttt | 120 |
| gaaggcggca atctggaggc taaggtcacc atggatattt ttggcttttg gcaggaagtg | 180 |
| aaagcagtgt tagagaagac agatgaaccg ggtaaatata cggccgatgg cggcaaacat | 240 |
| gatgcctata tcattcgcag ccatgtgaaa gatcattaca tcttttatag cgagggcgaa | 300 |
| tgcgctggct atccggttcc gggggtgtgg ctcgtgggca gagaccccaa gaacaacctg | 360 |
| gaagccttgg aggactttga aaagccgca ggagcccgcg gactcagcac ggagagcatc | 420 |
| ctcatccct ggcagagcga acccagctct ccaggg | 456 |

<210> SEQ ID NO 99
<211> LENGTH: 456
<212> TYPE: DNA
<213> ORGANISM: Artificial Sequence
<220> FEATURE:
<223> OTHER INFORMATION: lipocalin mutein

<400> SEQUENCE: 99

| | |
|---|---|
| acctcagacg aggagattca ggatgtgtca gggacgtggt atctgaaggc gatgacggtg | 60 |
| gattctgatt gcttttggat tgatgatgtg tcagttacgc caatgactct gactacccttt | 120 |
| gaaggcggca atctggaggc taaggccacc atggatattt ttggcttttg gcaggaagtg | 180 |
| gaagcagtgt tagagaagac agatgaaccg ggtaaatata cgaccgatgg cggcaaacat | 240 |
| gttgcctata tcattcgcag ccatgtgaaa gatcatcaca tcttttatag cgagggcgaa | 300 |
| tgcgctggct atccggttcc gggggtgtgg ctcgtgggca gagaccccaa gaacaacctg | 360 |
| gaagccttgg aggactttga aaagccgca ggagcccgcg gactcagcac ggagagcatc | 420 |
| ctcatcccca ggcagagcga aaccagctct ccaggg | 456 |

<210> SEQ ID NO 100
<211> LENGTH: 456
<212> TYPE: DNA
<213> ORGANISM: Artificial Sequence
<220> FEATURE:
<223> OTHER INFORMATION: lipocalin mutein

<400> SEQUENCE: 100

| | |
|---|---|
| gcctcagacg aggagattca ggatgtgtct gggacgtggt atctgaaggc gatgacggtg | 60 |
| gattctgatt gcttttggat tgatgatgtg tcagttacgc caatgactct gactacccttt | 120 |
| gaaggcggca atctggaggc taaggtcacc atggatattt ttggcttttg gcaggatgtg | 180 |
| aaagcagtgt tagagaagac agatgaaccg ggtaagtata cggccgatgg cggcaaacat | 240 |
| gatgcctata tcattagcag tcatgtgaaa gataattaca tcttttatag cgagggcgaa | 300 |
| tgcgctggct atccggttcc gggggtgtgg ctcgtgggca gagaccccaa gaacaaccag | 360 |

```
gaagccttgg aggactttga gaaagccgca ggagcccgcg gactcagcac ggagagcatc      420
ctcatcccca ggcagagcga aaccagctct ccaggg                                456

<210> SEQ ID NO 101
<211> LENGTH: 456
<212> TYPE: DNA
<213> ORGANISM: Artificial Sequence
<220> FEATURE:
<223> OTHER INFORMATION: lipocalin mutein

<400> SEQUENCE: 101
gcctcagacg aggagattca ggatgtgtca gggatgtggt atctgaaggc gatgacggtg       60
gattctgatt gcttttggat tgatgatgtg tcagttacgc caatgactct gactacccat      120
gaaggcggca atctggaggc taaggtcacc atggatattt ttggcttttg gcaggaagtg      180
gaagcagtgt tagagaagac agatgaaccg ggtaaatata cggccgatgg cggcaaacat      240
gtggcctata tcagtcgcag ccatgtgaaa gatcattaca tcttttatag cgagggcgaa      300
tgcgctggct atccggttcc gggggtgtgg ctcgtgggca gagaccccaa gaacaacctg      360
gaagccttgg aggactttga gaaagccgca ggagcccgcg gactcagcac ggagagcatc      420
ctcatcccca ggcagagcga aaccagctct ccaggg                                456

<210> SEQ ID NO 102
<211> LENGTH: 456
<212> TYPE: DNA
<213> ORGANISM: Artificial Sequence
<220> FEATURE:
<223> OTHER INFORMATION: lipocalin mutein

<400> SEQUENCE: 102
gcctcagacg aggagattca ggatgtgtca gggacgtggt atctgaaggc gatgacggtg       60
gattctgatt gcttttggat tgatgatgtg tcagttacgc caatgactct gactacccTT      120
gaaggcggca atctggaggc taaggtcacc atggatattt ttggcttttg gcaggatgtg      180
gaagcagtgt tagagaagac agatgaaccg ggtaaatata ccgccgatgg cggcaaacat      240
gttgcctata tcattcgcag ccatgtgaaa gatcattaca tcttttatag cgagggcgaa      300
tgcgctggct atccggttcc gggggtgtgg ctcgtgggca gagaccccaa gaacaacctg      360
gaagccttgg aggactttga gaaagctgca ggagcccgcg gactcagtac ggagagcatc      420
ctcatcccca ggctgagcga aaccagctct ccaggg                                456

<210> SEQ ID NO 103
<211> LENGTH: 456
<212> TYPE: DNA
<213> ORGANISM: Artificial Sequence
<220> FEATURE:
<223> OTHER INFORMATION: lipocalin mutein

<400> SEQUENCE: 103
gcctcagacg aggagattca ggatgtgtca gggacgtggt atctgaaggc gatgacggtg       60
gattctgatt gcttttggat tgatgatgtg tcagttacgc caatgactct gactacccTT      120
gaaggcggca atctggaggc taaggtcacc atggatattt ttggcttttg gcaggaagtg      180
gaagcagtgt tagagaggac agatgaaccg ggtaaatata cggccgatgg cggcaaacat      240
gttgcctata tcattcgcag ccatgtgaaa gatcattaca tcttttatag cgagggcgaa      300
tgcgctggct atccggttcc gggggtgtgg ctcgtgggca gagaccccaa gaacaacctg      360
```

```
gaagccttgg aggactttga gaaagccgca ggagcccgcg gactcagcac ggagagcatc    420
ctcatcccca ggcagagcga aaccagctct ccaggg                              456
```

<210> SEQ ID NO 104
<211> LENGTH: 456
<212> TYPE: DNA
<213> ORGANISM: Artificial Sequence
<220> FEATURE:
<223> OTHER INFORMATION: lipocalin mutein

<400> SEQUENCE: 104

```
acctcagacg aggagattca ggatgtgtca gggacgtggt atctgaaggc gatgacggtg    60
gattctgatt gcttttggat tgatgatgtg tcagttacgc caatgactct gactacccct   120
gaaggcggca atctggaggc taaggtcacc atggatattt ttggcttttg gcaggaagtg   180
gaagcagtgt tagaaaagac agatgaaccg ggtaaatata cggccggtgg cggcaaacat   240
gttgcctata tcaatcgcag ccatgtgaaa gatcattacg tcttttatag cgagggcgaa   300
tgcgctggct atccggttcc gggggtgtgg ctcgtgggca gagacccaa gaacaacctg    360 gaagccttgg aggactttga gaaagccgca ggagcccgcg gactcagcac ggagagtatc   420
ctcatcccca ggcagagcga aaccagctct ccaggg                              456
```

<210> SEQ ID NO 105
<211> LENGTH: 456
<212> TYPE: DNA
<213> ORGANISM: Artificial Sequence
<220> FEATURE:
<223> OTHER INFORMATION: lipocalin mutein

<400> SEQUENCE: 105

```
gcctcagacg aggagtttca ggatgtgtca gggacgtggt atctgaaggc gatgacggtg   60
gattctgatt gcttttggat tgatgatgtg tcagttacgc caatgactct gactacccct  120
gaaggcggca atctggaggc taaggtcacc atggatattt ttggcttttg gcaggaagtg  180
gaagcagtgt tagagaagac agatgcaccg ggtaaatata cagccgatgg aggcaaacat  240
gttgcctata tcaatcgcag ccatgagaaa gatcattaca tcttttatag cgagggcgaa  300
tgcgctggct atccggtacc gggggtgtgg ctcgtgggca gagacccaa gaacaacctg   360 gaagccttgg aggactttga gaaagccgca ggagcccgcg gactcagcac ggagagcatc  420
ctcatcccca ggcagagcga aaccagctct ccaggg                             456
```

<210> SEQ ID NO 106
<211> LENGTH: 456
<212> TYPE: DNA
<213> ORGANISM: Artificial Sequence
<220> FEATURE:
<223> OTHER INFORMATION: lipocalin mutein

<400> SEQUENCE: 106

```
acctcagacc aggagattca ggatgtgtca gggacgtggt atctgaaggc gatgacggtg    60
gattccgatt gcttttggat tgatgatgtg tcagttacgc caatgactct gactacccct   120
gaaggcggca atctggaggc taaggtcacc atggatattt ttggcttttg gcaggaagtg   180
gaagcagtgt tagggaagac agatgaaccg ggtaaatata cggccgatgg cggcaaacat   240
gctgcctata tcattcgcag ccatgtgaaa gatcattaca tcttttatag cgagggcgaa   300
```

-continued

```
tgcgctggct atccggttcc gggggtgtgg ctcgtgggca gagacccaa gaacaacctg    360 gaagccttgg aggacttcga gaaagccgca ggagcccgcg gactcagcac ggagagcatc    420
ctcatcccca ggcagagcga aaccagcgct ccaggg                              456
```

UNITED STATES PATENT AND TRADEMARK OFFICE
CERTIFICATE OF CORRECTION

PATENT NO. : 11,168,119 B2
APPLICATION NO. : 16/478465
DATED : November 9, 2021
INVENTOR(S) : Christine Rothe et al.

It is certified that error appears in the above-identified patent and that said Letters Patent is hereby corrected as shown below:

In the Claims

Column 143, Line 36, in Claim 7, "Val85 → Ala" should be changed to --Val 85 → Ala--.

Column 144, Line 58, in Claim 15, "Val 9343 Glu" should be changed to --Val 93 → Glu--.

Column 146, Line 20, in Claim 16, "Ser 5 → Phe" should be changed to --Ser 58 → Phe--.

Signed and Sealed this
Fifth Day of July, 2022

Katherine Kelly Vidal
*Director of the United States Patent and Trademark Office*